(12) United States Patent
Funahashi

(10) Patent No.: US 9,296,823 B2
(45) Date of Patent: Mar. 29, 2016

(54) DIAGNOSIS AND TREATMENT OF CANCER USING ANTI-GPR49 ANTIBODY

(71) Applicant: Chugai Seiyaku Kabushiki Kaisha, Tokyo (JP)

(72) Inventor: Shinichi Funahashi, Tokyo (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/173,424

(22) Filed: Feb. 5, 2014

(65) Prior Publication Data

US 2014/0147383 A1 May 29, 2014

Related U.S. Application Data

(62) Division of application No. 12/742,892, filed as application No. PCT/JP2008/070751 on Nov. 14, 2008, now Pat. No. 8,680,243.

(30) Foreign Application Priority Data

Nov. 14, 2007 (JP) .................................. 2007-295341

(51) Int. Cl.
  C07K 16/30 (2006.01)
  C07K 16/00 (2006.01)
  C07K 14/00 (2006.01)
  G01N 33/574 (2006.01)
  A61K 51/10 (2006.01)

(52) U.S. Cl.
  CPC ............. *C07K 16/30* (2013.01); *A61K 51/1045* (2013.01); *G01N 33/574* (2013.01); *G01N 33/57492* (2013.01); *C07K 2317/24* (2013.01); *C07K 2317/34* (2013.01); *C07K 2317/565* (2013.01); *C07K 2317/732* (2013.01); *C07K 2317/734* (2013.01); *C07K 2319/00* (2013.01); *C07K 2319/30* (2013.01); *G01N 2333/726* (2013.01)

(58) Field of Classification Search
  CPC .......... C07K 16/30; C07K 16/00; C07K 14/00
  USPC ............. 530/387.1, 387.9, 388.1, 391.1, 350, 530/391.7
  See application file for complete search history.

(56) References Cited

U.S. PATENT DOCUMENTS

| | | | |
|---|---|---|---|
| 2004/0132101 A1 | 7/2004 | Lazar et al. | |
| 2006/0121032 A1* | 6/2006 | Dahiyat et al. | 424/144.1 |
| 2007/0059308 A1 | 3/2007 | Hua et al. | |
| 2008/0207497 A1* | 8/2008 | Ramakrishna et al. | 514/12 |
| 2009/0191205 A1 | 7/2009 | Gurney | |
| 2009/0215711 A1 | 8/2009 | Morris et al. | |

FOREIGN PATENT DOCUMENTS

| | | |
|---|---|---|
| EP | 1602930 | 12/2005 |
| JP | 2003-274981 | 9/2003 |
| JP | 2006-512407 | 4/2006 |
| WO | WO 99/15660 | 4/1999 |
| WO | WO 99/48921 | 9/1999 |
| WO | WO 00/71710 | 11/2000 |
| WO | WO 03/000928 | 1/2003 |
| WO | WO 2004/005457 | 1/2004 |
| WO | WO 2004/031413 | 4/2004 |
| WO | WO 2004/061423 | 7/2004 |
| WO | WO 2004/074436 | 9/2004 |
| WO | WO 2004/098521 | 11/2004 |
| WO | WO 2005/005601 | 1/2005 |
| WO | WO 2005/040828 | 5/2005 |
| WO | WO 2005/107396 | 11/2005 |
| WO | WO 2006/019447 | 2/2006 |
| WO | WO 2006/104989 | 10/2006 |
| WO | WO 2007/093008 | 8/2007 |
| WO | WO 2009/005809 | 1/2009 |
| WO | WO 2009/022907 | 2/2009 |

OTHER PUBLICATIONS

Harmsen and Haard (Appl Microbiol Biotechnol 2007, 77:13-22).*
Dekaney et al., *Am J Physiol Gastrointest Liver Physiol.* Sep. 2009, 297(3):G461-70.
PCT/JP2008/070751 -Translation of International Preliminary Report on Patentability, Jul. 8, 2010.
Sakamoto, Heisei 18 Nendo Soukatsu Human Kenkyu Houkokusyo, Apr. 24, 2007: 25-8.
McClanahan, et al., Identification of Overexpression of Orphan G Protein-Coupled Receptor GPR49 in Human Colon and Ovarian Primary Tumors, Cancer biology & Therapy, Apr. 2006, vol. 5, pp. 419-426.
Tagliabue, E. et al., Selection of monoclonal antibodies which induce internalization and phosphorylation of p185HER2 and growth inhibition of cells with HER2/NEU gene amplification; Int'l J. of Cancer; 1991; vol. 47; pp. 933-937.
Hsu, et al., Characterization of Two LGR Genes Homologous to Gonadotropin and Thyrotropin Receptors with Extracellular Leucine-Rich Repeats and a G Protein-Coupled, Seven-Transmembrane Region; Molecular Endocrinology; 1998; vol. 12(12); pp. 1830-1845.
Hsueh, A. J. W., et al., Hormonology: a genomic perspective on hormonal research, J. of Endocrinology; 2005; 187; pp. 333-338.

(Continued)

*Primary Examiner* — Yan Xiao
(74) *Attorney, Agent, or Firm* — Cooley LLP

(57) ABSTRACT

Antibodies that bind to a GPR49 protein and have cell proliferation inhibitory activity against cells expressing the GPR49 protein are disclosed. Cell proliferation inhibitory activities are cytotoxic activities such as antibody-dependent cell-mediated cytotoxicity and complement-dependent cytotoxicity. Pharmaceutical compositions, cell-proliferation inhibitors, and anticancer agents containing an antibody of the present invention as an active ingredient are also disclosed. Examples of cancer include gastric cancer, colon cancer, hepatocellular carcinoma, lung cancer, prostate cancer, ovarian cancer, Ewing's sarcoma, and glioma. Furthermore, methods for diagnosing cancer by detecting expression of a GPR49 protein or a gene encoding a GPR49 protein, and diagnostic agents and kits to be used in these methods are also disclosed.

13 Claims, 16 Drawing Sheets

(56) References Cited

OTHER PUBLICATIONS

Kristiansen, Kurt, Molecular mechanisms of ligand binding, signaling, and regulation within the superfamily of G-protein-coupled receptors: molecular modeling and mutagenesis approaches to receptor structure and function, Pharmacology & Therapeutics, 1 03; 2004; pp. 21-80.

Luo, Ching-Wei, et al., Bursicon, the insect cuticle-hardening hormone, is a heterodimeric cystine knot protein that activates G protein-coupled receptor LGR2; PNAS, Feb. 22, 2005; vol. 102, No. 8; pp. 2820-2825.

Morita, H., et al.; Neonatal Lethality of LGR5 Null Mice Is Associated with Ankyloglossia and Gastrointestinal Distension; Mol Cell Biology; Nov. 2004; vol. 24, No. 22; pp. 9736-9743.

Morris, Rebecca J., et al., Capturing and profiling adult hair follicle stem cells; Nature Biotechnology, Apr. 2004, vol. 22, No. 4; pp. 411-417.

Yamamoto, Y., et al., Overexpression of Orphan G-Protein-Coupled Receptor, Gpr49, in Human Hepatocellular Carcinomas with J1-Catenin Mutations; Hepatology; 2003; vol. 37, No. 3; pp. 528-533.

Sasaki, Yuka, et al., Establishment of a novel monoclonal antibody against LGR5; Biochem Biopphys Res Commun.; 2010; 394; pp. 498-502.

Weiguang, M., et al., Early study on LGR5/GPR49 molecule as a potential colon cancer stem cell target for the antibody conjugated drug treatment; Proceedings of the AACR (Annual Meeting); Apr. 2010; vol. 51; pp. 1041, #4289.

Kipps. T .. et al.. Importance of Immunoglobulin Isotype in Human Antibody-Dependent. Cell-Mediated Cytotoxicity Directed by Murine Monoclonal Antibodies; J. Exp. Med.; Jan. 1985; vol. 161; pp. 1-17.

Rot, et al, BMC Cancer. Oct. 6, 2011;11:429.

Greenspan, et al, Nat Biotechnol. Oct. 1999;17(10):936-7.

Bowie, et al, Science. Mar. 16, 1990;247(4948):1306-10.

Stancovski, et al, Proc Natl Acad Sci U S A. Oct. 1, 1991;88(19):8691-5.

\* cited by examiner

DIAGNOSIS AND TREATMENT OF CANCER USING ANTI-GPR49 ANTIBODY

CROSS REFERENCE TO RELATED APPLICATIONS

This application is a divisional application of U.S. patent application Ser. No. 12/742,892, filed May 13, 2010, which is a National Stage Entry Application of PCT Application No. PCT/JP2008/070751, filed Nov. 14, 2008, which claims priority to JP Application No. 2007-295341, filed Nov. 14, 2007. The contents of these aforementioned applications are incorporated herein by reference in their entireties for all purposes.

TECHNICAL FIELD

The present invention relates to methods for diagnosing and treating cancer, and anticancer agents.

BACKGROUND ART

GPR49 molecule is a protein encoded by the ENSG00000139292 gene of human chromosome 12q12, and its amino acid sequence characteristics have revealed that it is a member of the LGR family (Leucine-rich GPCR family, hereinafter referred to as the LGR family), which is a hormone receptor family of G-protein coupled seven-transmembrane proteins (Non-patent Document 1). Members of the LGR family include hormone receptors such as LHR, TSHR, and FSH, as well as LGR7 and LGR8, ligands of which are relaxin, insulin-like peptide 3 (INSL3), and such (Non-patent Document 2). All ligands are known to comprise heterogeneous peptides, and mainly transmit signals via cAMP. The LGR family has a structure comprising a seven-transmembrane protein region and an N-terminal long extracellular region. In the extracellular region, there are 9 to 17 repeats of a leucine-rich region (leucine-rich repeat: LRR) comprising of 25 amino acids or so. GPR49 comprises 17 LRRs (Non-patent Document 1). According to analysis of TSHR and such, G-protein-coupled signal transduction occurs when a ligand binds to this extracellular LRR with high affinity, and also to the second extracellular loop region (Non-patent Document 3; Pharmacology & Therapeutics 103, 21 (2004)). The ligands of GPR49 have not yet been identified, but since ligands of DLGR2, a closely-related LGR of *Drosophila*, were found to be Bursicon comprising Burs and Pburs (partner of Bur) which are molecules of the BMP antagonist family, there are reports that the ligands of LGR4, LGR5 (GPR49), and LGR6 with yet unknown ligands may also be BMP antagonists (Non-patent Document 4 and Non-patent Document 2). As for the functions of these molecules, analyses of knockout mice have suggested that they are involved with ankyloglossia (ankylogenesis) (Non-patent Document 5). Furthermore, from gene expression analyses of hair follicle stem cells, they are speculated to be involved in the proliferation of stem cells (Non-patent Document 6).

With regard to involvement in cancer, Yamamoto et al. have reported that GPR49 is highly expressed in liver cell cancer patients (Non-patent Document 7), and also that expression of GPR49 at the mRNA level is upregulated particularly in patients with mutations in beta-catenin. Furthermore, Ito et al. have mentioned GPR49 as an example of a molecule highly expressed in gastric cancer patients based on Affymetrix Genechip data analyses (Patent Document 1).

It has been reported that expression of GPR49 is upregulated in colon cancer and ovarian cancer, and upregulation of expression at the mRNA level is observed at 64% (25/39) of colon cancer patients and 53% (18/33) of ovarian cancer patients (Non-patent Document 8). Immunostaining using PoAb has revealed that it is expressed in the normal tissues of placenta and skeletal muscles (Non-patent Document 8). As for its involvement with canceration, focus formation assay showed that NIH3T3 subjected to only gene transfer did not show focus formation in four weeks, but cells supplemented with a culture supernatant obtained from a SW620 culture (conditioned medium) showed focus formation within three weeks. Accordingly, GPR49 is assumed to induce ligand-dependent canceration. Accumulation of subG1 cells and apoptosis induction was observed in siRNA experiments. It is suggested that GPR49 may have functions of inhibiting apoptosis induction in colon cancer cells.

However, based on expression of cancer cell lines it has also been reported that although GPR49 expression is upregulated in colon cancer, ovarian cancer, glioma, and melanoma, such an upregulation is not seen in breast cancer and lung cancer (Non-patent Document 8).

[Patent Document 1] WO 2000/071710
[Non-patent Document 1] Mol. Endocrinology 12, 1830 (1998)
[Non-patent Document 2] Journal of Endocrinology 187, 333 (2005)
[Non-patent Document 3] Pharmacology & Therapeutics 103, 21 (2004)
[Non-patent Document 4] PNAS 102, 2820 (2005)
[Non-patent Document 5] Molecular and Cellular Biology, 24, 9736 (2004)
[Non-patent Document 6] Nature Biotechnology 22, 411 (2004)
[Non-patent Document 7] Hepatology 37, 528 (2003)
[Non-patent Document 8] Cancer Biology & Therapy 5, 419 (2006)

DISCLOSURE OF THE INVENTION

Problems to be Solved by the Invention

An objective of the present invention is to provide novel methods for diagnosing and treating cancer, or to provide novel cell proliferation inhibitory agents and anticancer agents.

Means for Solving the Problems

The present inventors discovered that not only the GPR49 gene but also the GPR49 protein are highly expressed in cancer cells such as gastric cancer, colon cancer, hepatocellular carcinoma, lung cancer, ovarian cancer, Ewing's sarcoma, and glioma. Furthermore, the present inventors produced monoclonal antibodies against the GPR49 protein and discovered for the first time that the GPR49 protein having a molecular weight of 100 kDa is cleaved and divided into 60-kDa and 40-kDa fragments. Since the N-terminal 60-kDa fragment is cleaved and is secreted to the outside of the cell, it is useful as a diagnostic marker for cancer. Furthermore, the C-terminal 40-kDa fragment may be useful as a target of therapeutic antibodies.

Furthermore, the present inventors determined the complement-dependent cytotoxicity (CDC) and also the antibody-dependent cell-mediated cytotoxicity (ADCC) of anti-GPR49 antibodies, and discovered that the anti-GPR49 antibodies have CDC activity and ADCC activity against GPR49-expressing cells. Using toxin-bound antibodies, the present inventors also discovered an activity that leads to cell damage of GPR49-expressing cells. From the above-mentioned findings, the present inventors discovered that the anti-GPR49 antibodies are effective for diagnosing, preventing, and treating various types of primary or metastatic cancers, and completed the present invention. More specifically, the present inventors discovered that GPR49 is useful as a tool for treating or diagnosing cancers in which GPR49 expression is upregulated such as gastric cancer, colon cancer, hepatocellular carcinoma, lung cancer, ovarian cancer, Ewing's sarcoma, and glioma, and completed the present invention.

That is, the present invention provides antibodies that bind to a GPR49 protein. Furthermore, the present invention provides antibodies that bind to a GPR49 protein, and have a cytotoxic activity against cells expressing the GPR49 protein. Preferably, the cytotoxic activity is ADCC activity or CDC activity. The present invention also provides antibodies to which a cytotoxic substance is conjugated.

Furthermore, the present invention provides pharmaceutical compositions comprising an antibody that binds to a GPR49 protein as an active ingredient. The present invention also provides cell proliferation inhibitory agents comprising an antibody that binds to a GPR49 protein as an active ingredient. The present invention also provides anticancer agents comprising an antibody that binds to a GPR49 protein as an active ingredient.

Alternatively, the present invention provides pharmaceutical compositions comprising an antibody that binds to a GPR49 protein and pharmaceutically acceptable carriers. More specifically, the present invention provides:

[1] an antibody that binds to a GPR49 protein, and which has cell proliferation inhibitory activity against cells expressing the GPR49 protein;
[2] the antibody of [1], wherein the cell proliferation inhibitory activity is cytotoxic activity;
[3] The antibody of [2], wherein the cytotoxic activity is antibody-dependent cytotoxic activity;
[4] the antibody of [2], wherein the cytotoxic activity is complement-dependent cytotoxic activity;
[5] the antibody of any one of [1] to [4], wherein a cytotoxic substance is bound to the antibody;
[6] the antibody of [5], which has an internalizing activity;
[7] the antibody of any one of [1] to [6], which suppresses cancer cell proliferation;
[8] the antibody of [7], wherein the cancer cell is any one of gastric cancer cells, colon cancer cells, liver cancer cells, lung cancer cells, ovarian cancer cells, Ewing's sarcoma cells, and glioma cells;
[9] the antibody described in any of (1) to (20) below:
(1) an antibody comprising an H chain having the amino acid sequence of SEQ ID NO: 5 as CDR1, the amino acid sequence of SEQ ID NO: 6 as CDR2, and the amino acid sequence of SEQ ID NO: 7 as CDR3;
(2) an antibody comprising an L chain having the amino acid sequence of SEQ ID NO: 10 as CDR1, the amino acid sequence of SEQ ID NO: 11 as CDR2, and the amino acid sequence of SEQ ID NO: 12 as CDR3;
(3) an antibody comprising the H chain of (1) and the L chain of (2);
(4) an antibody comprising an H chain having the amino acid sequence of SEQ ID NO: 15 as CDR1, the amino acid sequence of SEQ ID NO: 16 as CDR2, and the amino acid sequence of SEQ ID NO: 17 as CDR3;
(5) an antibody comprising an L chain having the amino acid sequence of SEQ ID NO: 20 as CDR1, the amino acid sequence of SEQ ID NO: 21 as CDR2, and the amino acid sequence of SEQ ID NO: 22 as CDR3;
(6) an antibody comprising the H chain of (4) and the L chain of (5);
(7) an antibody comprising an H chain having the amino acid sequence of SEQ ID NO: 25 as CDR1, the amino acid sequence of SEQ ID NO: 26 as CDR2, and the amino acid sequence of SEQ ID NO: 27 as CDR3;
(8) an antibody comprising an L chain having the amino acid sequence of SEQ ID NO: 30 as CDR1, the amino acid sequence of SEQ ID NO: 31 as CDR2, and the amino acid sequence of SEQ ID NO: 32 as CDR3;
(9) an antibody comprising the H chain of (7) and the L chain of (8);
(10) an antibody comprising an H chain having the amino acid sequence of SEQ ID NO: 35 as CDR1, the amino acid sequence of SEQ ID NO: 36 as CDR2, and the amino acid sequence of SEQ ID NO: 37 as CDR3;
(11) an antibody comprising an L chain having the amino acid sequence of SEQ ID NO: 40 as CDR1, the amino acid sequence of SEQ ID NO: 41 as CDR2, and the amino acid sequence of SEQ ID NO: 42 as CDR3;
(12) an antibody comprising the H chain of (10) and the L chain of (11);
(13) an antibody comprising an H chain having the amino acid sequence of SEQ ID NO: 45 as CDR1, the amino acid sequence of SEQ ID NO: 46 as CDR2, and the amino acid sequence of SEQ ID NO: 47 as CDR3;
(14) an antibody comprising an L chain having the amino acid sequence of SEQ ID NO: 50 as CDR1, the amino acid sequence of SEQ ID NO: 51 as CDR2, and the amino acid sequence of SEQ ID NO: 52 as CDR3;
(15) an antibody comprising the H chain of (13) and the L chain of (14);
(16) an antibody comprising an H chain having the amino acid sequence of SEQ ID NO: 66 as CDR1, the amino acid sequence of SEQ ID NO: 67 as CDR2, and the amino acid sequence of SEQ ID NO: 68 as CDR3;
(17) an antibody comprising an L chain having the amino acid sequence of SEQ ID NO: 71 as CDR1, the amino acid sequence of SEQ ID NO: 72 as CDR2, and the amino acid sequence of SEQ ID NO: 73 as CDR3;
(18) an antibody comprising the H chain of (16) and the L chain of (17);
(19) an antibody having one or more amino acid substitutions, deletions, additions, and/or insertions in the antibody of any of (1) to (18), which has equivalent activity as the antibody of any of (1) to (18);
(20) an antibody that binds to the same epitope as the GPR49 protein epitope bound by the antibody of any of (1) to (18);
[10] the antibody of any one of [1] to [9], comprising a human constant region;
[11] the antibody of [10], which is a chimeric antibody, humanized antibody, or human antibody;
[12] a pharmaceutical composition comprising the antibody of any one of [1] to [11] as an active ingredient;
[13] a cell proliferation-suppressing agent comprising the antibody of any one of [1] to [11] as an active ingredient;
[14] an anticancer agent comprising the antibody of any one of [1] to [11] as an active ingredient;
[15] the anticancer agent of [14], wherein the cancer is any cancer selected from the group consisting of gastric cancer, colon cancer, hepatocellular carcinoma, lung cancer, ovarian cancer, Ewing's sarcoma, and glioma;
[16] a method for diagnosing cancer, comprising detecting a GPR49 protein or a gene encoding a GPR49 protein;
[17] the diagnostic method of [16], comprising detecting a GPR49 protein;
[18] the diagnostic method of [17], wherein the GPR49 protein detection is performed using an antibody that binds to a GPR49 protein;

[19] a method for diagnosing cancer, comprising the steps of:
(a) providing a sample collected from a subject; and
(b) detecting a GPR49 protein contained in the sample of (a) using an antibody that binds to the GPR49 protein;
[20] a method for diagnosing cancer, comprising the steps of:
(a) administering to a subject a radioisotope-labeled antibody comprising an activity to bind to a GPR49 protein; and
(b) detecting accumulation of the radioisotope; and
[21] the diagnostic method of any one of [16] to [20], wherein the cancer is any cancer selected from the group consisting of gastric cancer, colon cancer, hepatocellular carcinoma, lung cancer, ovarian cancer, Ewing's sarcoma, and glioma.

The present invention also provides:
[22] a method for suppressing cell proliferation using the antibody of any one of [1] to [11];
[23] a method for treating or preventing cancer, which comprises the step of administering the antibody of any one of [1] to [11]; and
[24] use of the antibody of any one of [1] to [11] in the manufacture of a cell proliferation-suppressing agent or an anticancer agent.

Effects of the Invention

Since the anti-GPR49 antibodies of the present invention have complement-dependent cytotoxicity as well as antibody-dependent cell-mediated cytotoxicity against GPR49-expressing cells, and when a toxin is conjugated to them, they have activities of leading to cell damage in GPR49-expressing cells, these antibodies are effective for diagnosing, preventing, and treating various types of primary or metastatic cancers.

BRIEF DESCRIPTION OF THE DRAWINGS

FIG. 13 also depicts sequence comparison of GPR49 (partial of SEQ ID NO: 1), del-494W (SEQ ID NO: 80), del-537H (SEQ ID NO: 81), sGPR49Fc (SEQ ID NO: 82), GST-495-537 (SEQ ID NO: 83), GST-496-516 (SEQ ID NO: 84), GST-510-529 (SEQ ID NO: 85), and GST-517-537 (SEQ ID NO: 86).

BEST MODE FOR CARRYING OUT THE INVENTION

GPR49

Figure 1:
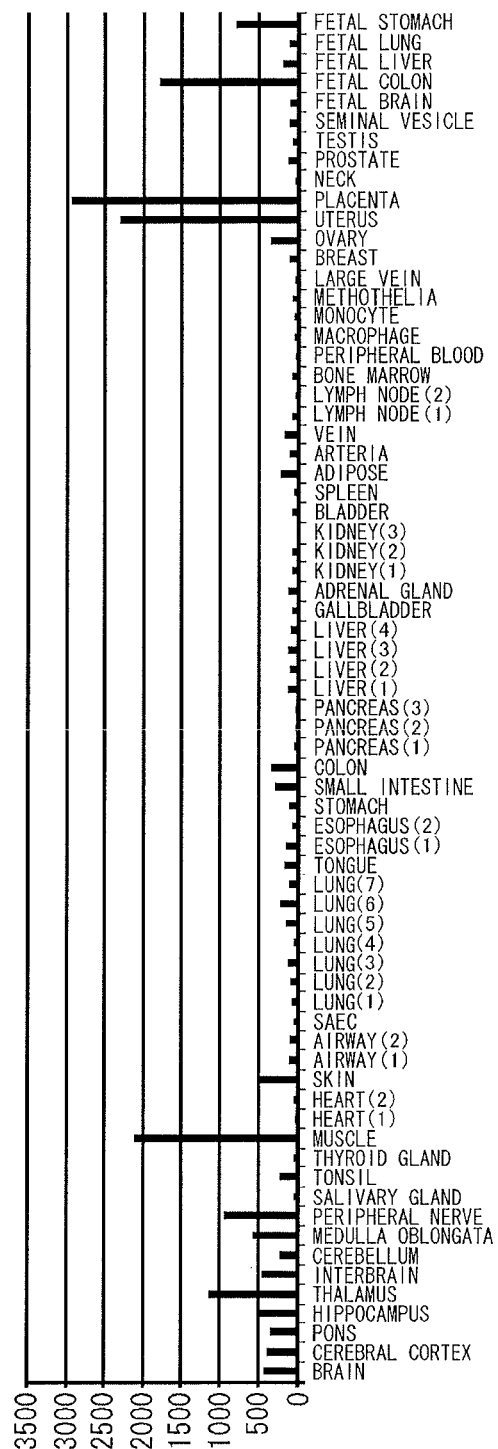
FIG. 1 shows the expression profile of human GPR49 in normal tissues. The values were obtained from Exon Array analysis, and higher the value, higher the mRNA expression level.

GPR49 is a seven-transmembrane protein which is a member of the LGR family. An amino acid sequence of human GPR49 and a gene sequence encoding it are disclosed in NCBI Accession Nos. NP_003658.1 (SEQ ID NO: 1) and NM_003667.2 (SEQ ID NO: 2), respectively. In the present invention, a "GPR49 protein" refers to both the full-length protein and fragments thereof. "Fragments" refers to polypeptides comprising any region of the GPR49 protein, and they may not have the function of the naturally-occurring GPR49 protein. Examples of the fragments include fragments comprising the extracellular regions of the GPR49 protein. Positions 1 to 556, 615 to 637, 704 to 722, and 792 to 800 in the amino acid sequence of SEQ ID NO: 1 correspond to the extracellular regions of the GPR49 protein. Positions 557 to 579, 592 to 614, 638 to 660, 681 to 703, 723 to 745, 769 to 791, and 801 to 823 in the amino acid sequence of SEQ ID NO: 1 correspond to the transmembrane regions.

Preparation of Anti-GPR49 Antibodies

The anti-GPR49 antibodies used in the present invention may be of any origin, and may be of any type and in any form, as long as they bind to a GPR49 protein. Specifically, known antibodies such as non-human animal antibodies (for example, mouse antibodies, rat antibodies, and camel antibodies), human antibodies, chimeric antibodies, and humanized antibodies can be used. In the present invention, the antibodies may be monoclonal or polyclonal antibodies, but monoclonal antibodies are preferred. Binding of antibodies to the GPR49 protein is preferably a specific binding.

Anti-GPR49 antibodies to be used in the present invention can be obtained as polyclonal or monoclonal antibodies using well-known techniques. In particular, monoclonal antibodies derived from a mammal are preferable as the anti-GPR49 antibodies for use in the present invention. The monoclonal antibodies derived from a mammal include antibodies produced by hybridoma, and antibodies produced by a host transformed by genetic engineering techniques with an expression vector containing an antibody gene.

A monoclonal antibody-producing hybridoma can be prepared, essentially by using the following known technique. First, Animals are immunized using the GPR49 protein as a sensitizing antigen according to a general immunization method. Immunocytes that are obtained from the immunized animals are then fused to known parental cells by a general cell fusion method to obtain hybridomas. Furthermore, hybridomas that produce an anti-GPR49 antibody can be selected from these hybridomas by screening for cells that produce the antibodies of interest using a general screening method.

Specifically, monoclonal antibodies are prepared, for example, as follows. First, the GPR49 protein for use as the sensitizing antigen for acquiring the antibodies can be obtained by expressing a GPR49 gene. The nucleotide sequence of a GPR49 gene is disclosed in NCBI Accession No. NM_003667.2 (SEQ ID NO: 2) and such. Specifically, after a suitable host cell is transformed with a known expression vector in which the gene sequence encoding GPR49 is inserted, the desired human GPR49 protein can be purified by a known method from the host cell or its culture supernatant. Alternatively, a purified naturally-derived GPR49 protein may be similarly used. Furthermore, as used in the present invention, a fusion protein prepared by fusing a desired partial polypeptide of a GPR49 protein with another polypeptide may be used as an immunogen. For example, Fc fragments of antibodies, peptide tags, or such can be used to produce a fusion protein for use as an immunogen. A vector that expresses the fusion protein can be prepared by fusing the desired genes encoding two or more kinds of polypeptide fragments in frame, and inserting the fused genes into an expression vector. Methods for producing fusion proteins are described in Molecular Cloning 2nd ed. (Sambrook, J. et al., Molecular Cloning 2nd ed., 9.47-9.58, Cold Spring Harbor Lab. press, 1989).

The GPR49 protein purified as described above can be used as a sensitizing antigen for immunization of mammals. A partial peptide of GPR49 can also be used as a sensitizing antigen. For example, the following peptides can be used as a sensitizing antigen:
peptides obtained by chemical synthesis based on the amino acid sequence of human GPR49;
peptides obtained by incorporating a portion of the GPR49 gene into an expression vector and expressing it; and
peptides obtained by degrading the GPR49 protein with proteases.

The region and size of GPR49 used as partial peptides are not limited. Preferred regions can be selected from the amino acid sequences constituting the extracellular domains of GPR49 (positions 1 to 556, 615 to 637, 704 to 722, and 792 to 800 in the amino acid sequence of SEQ ID NO: 1). The number of amino acids constituting a peptide to be used as the sensitizing antigen is at least three or more, for example five or more, or preferably six or more. More specifically, peptides having 8 to 50 residues, or preferably 10 to 30 residues can be used as sensitizing antigens.

Mammals immunized by these sensitizing antigens are not particularly limited. To obtain monoclonal antibodies by the cell fusion method, the animal to be immunized is preferably selected considering its compatibility with the parental cells used for cell fusion. Generally, a rodent is preferred as the animals for immunization. Specifically, mice, rats, hamsters, or rabbits can be used as animals for immunization. Alternatively, monkeys or such may be used as animals for immunization.

The above-described animals can be immunized with a sensitizing antigen according to a known method. For example, as a general method, mammals can be immunized by injecting a sensitizing antigen intraperitoneally or subcutaneously. Specifically, the sensitizing antigen is administered to mammals several times every 4 to 21 days. The sensitizing antigen is diluted at an appropriate dilution ratio with Phosphate-Buffered Saline (PBS), physiological saline, or such, and then used for immunization. Furthermore, the sensitizing antigen may be administered together with an adjuvant. For example, the sensitizing antigen can be prepared by mixing with a Freund's complete adjuvant for emulsification. Furthermore, an appropriate carrier can be used for immunizing with the sensitizing antigen. Particularly when a partial peptide with a small molecular weight is used as a sensitizing antigen, the sensitizing antigen peptide is desirably conjugated to a carrier protein such as albumin or keyhole limpet hemocyanin, and then used for immunization.

Meanwhile, monoclonal antibodies can be obtained by DNA immunization. DNA immunization is a method for immunostimulating by administering to an animal to be immunized a vector DNA constructed so that a gene encoding an antigenic protein can be expressed in the immunized animal, and allowing the immunogen to express in vivo. Compared to conventional immunization methods in which a protein antigen is administered, the following advantages can be expected from DNA immunization.

Immunostimulation can be provided while maintaining the structure of a membrane protein such as GPR49.

There is no need to purify an immunogen.

On the other hand, it is difficult to combine DNA immunization with means for immunostimulation such as adjuvants. Since GPR49 has the structural feature of being a seven transmembrane conformation, it was expected that induction of an immune response while maintaining the naturally-occurring structure in vivo would be difficult. From such structural characteristics, actually obtaining by DNA immunization monoclonal antibodies that bind to GPR49, which is a protein belonging to the LGR family for which antibodies had been difficult to obtain, was an unexpected achievement.

To obtain monoclonal antibodies of the present invention by DNA immunization, first, a DNA that expresses a GPR49 protein is administered to an animal to be immunized. A DNA encoding GPR49 can be synthesized by known methods such as PCR. The obtained DNA is inserted into a suitable expression vector, and then administered to an animal to be immunized. Commercially available expression vectors such as pcDNA3.1 may be used as an expression vector. Conventional methods can be used to administer a vector to an organism. For example, gold particles adsorbed with an expression vector are shot into cells using a gene gun for DNA immunization.

According to the findings of the present inventors, hybridomas that produce GPR49-binding antibodies could not be obtained efficiently from mice immunized by intraperitoneal administration of cells forcedly expressing GPR49. On the other hand, hybridomas that produce GPR49-binding antibodies could be obtained efficiently from mice immunized using DNA immunization. In particular, the hybridomas of interest could be readily obtained from mice to which cells forcedly expressing GPR49 were administered after DNA immunization. That is, in a preferred method for obtaining the monoclonal antibodies of the present invention, a booster using GPR49-expressing cells is performed after DNA immunization.

Mammals are immunized as described above. After confirming the desired increase in the amount of antibody in the serum, immunocytes are collected from the mammals, and then subjected to cell fusion. In particular, splenocytes can be used as the preferred immunocytes.

A mammalian myeloma cell is used as a cell to be fused with the above-mentioned immunocyte. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine, respectively. Normal cells are killed since they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provides resistance to 2-deoxystreptamine antibiotics (gentamycin analogs) from the neomycin-resistant gene. Various types of myeloma cells that are suitable for cell fusion are known. For example, myeloma cells including the following cells can be used to produce the monoclonal antibodies of the present invention:

P3 (P3x63Ag8.653) (J. Immunol. (1979) 123, 1548-1550);
P3x63Ag8U.1 (Current Topics in Microbiology and immunology (1978) 81, 1-7);
NS-1 (Kohler, G. and Milstein, C. Eur. J. Immunol. (1976) 6, 511-519);
MPC-11 (Margulies, D. H. et al., Cell (1976) 8, 405-415);
SP2/0 (Shulman, M. et al., Nature (1978) 276, 269-270);
FO (de St. Groth, S. F. et al., J. Immunol. Methods (1980) 35, 1-21);
S194 (Trowbridge, I. S. J. Exp. Med. (1978) 148, 313-323);
R210 (Galfre, G. et al., Nature (1979) 277, 131-133), etc.

Cell fusions between the immunocytes and the myeloma cells are essentially carried out using known methods, for example, a method by Kohler and Milstein et al. (Kohler, G. and Milstein, C., Methods Enzymol. (1981) 73: 3-46).

More specifically, cell fusions can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide may also be added to improve fusion efficiency.

The ratio of immunocytes to myeloma cells may be determined at one's own discretion, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may also be added to the culture medium.

Cell fusion is carried out as follows. Predetermined amounts of immunocytes and myeloma cells are mixed well in the culture medium. PEG solution pre-heated to around 37° C. is mixed to produce fused cells (hybridomas). In the cell fusion method, for example, mean molecular weight of about 1,000 to 6,000 PEG is usually added at a concentration of 30% to 60% (w/v). Then, an appropriate culture medium described above is successively added to the mixture, and the sample is centrifuged to remove supernatant. This treatment is repeated several times to remove the unwanted cell fusion-promoting agent and others that are unfavorable to hybridoma growth.

Hybridomas thus obtained can be selected using a selection medium appropriate for the selection markers carried by myelomas used for cell fusion. For example, cells with HGPRT and TK deficiencies can be selected by culturing them in a HAT medium (a medium containing hypoxanthine, aminopterin, and thymidine). More specifically, when HAT-sensitive myeloma cells are used for cell fusion, cells that successfully fuse with normal cells can selectively grow in the HAT medium. Culture using the above-mentioned HAT medium is maintained for a sufficient time to kill cells other than the hybridoma of interest (non-fused cells). More specifically, the hybridoma of interest can be selected, usually by culturing for several days to several weeks. Hybridomas that produce the desired antibody can then be screened and singly-cloned by conducting a standard limiting dilution method.

Alternatively, a GPR49-recognizing antibody can be prepared using the method described in International Patent Publication No. WO 03/104453.

A desired antibody can be suitably screened and singly-cloned by a screening method based on a known antigen-antibody reaction. For example, the antigen is conjugated to a carrier such as polystyrene beads or the like, or a commercially available 96-well microtiter plate, followed by reaction with the culture supernatant of the hybridomas. Then, after the carrier is washed, it is reacted with an enzyme-labeled secondary antibody or the like. If the desired antibody that reacts with the sensitizing antigen is present in the culture supernatant, the secondary antibody will bind to the carrier via the antibody. Finally, the presence of the desired antibody in the culture supernatant can be determined by detecting secondary antibodies bound to the carrier. Hybridomas producing desired antibodies with an ability to bind to the antigen can be cloned by the limiting dilution method or the like. Antigens used for immunization as well as a substantially identical GPR49 protein can be suitably used in this case. For example, a GPR49-expressing cell line, an extracellular domain of GPR49, or an oligopeptide comprising a partial amino acid sequence constituting this region may be used as the antigen.

In addition to the above-mentioned method where hybridomas are obtained by immunizing non-human animals with an antigen, a desired antibody can be obtained by antigen sensitization of human lymphocytes. More specifically, first, human lymphocytes are sensitized with the GPR49 protein in vitro. Then, immunosensitized lymphocytes are fused with a suitable fusion partner. For example, human-derived myeloma cells that have infinite division potential can be used as a fusion partner (see Japanese Patent Application Kokoku Publication No. (JP-B) H01-59878 (examined, approved Japanese patent application published for opposition)). Anti-GPR49 antibodies obtained by this method are human antibodies that have binding activity to a GPR49 protein.

Alternatively, anti-GPR49 human antibodies can also be obtained by administering a GPR49 protein that serves as an antigen to a transgenic animal having a complete human antibody gene repertoire, or by immunizing such an animal with a DNA constructed to express GPR49 in the animal. Antibody-producing cells of the immunized animal can be immortalized by treatment such as cell fusion with a suitable fusion partner or Epstein-Barr virus infection. Human antibodies against the GPR49 protein can be isolated from the immortalized cells obtained in this manner (see International Patent Publication Nos. WO 94/25585, WO 93/12227, WO 92/03918, and WO 94/02602). Furthermore, cells that produce an antibody having the desired reaction specificity can be cloned by cloning the immortalized cells. When a transgenic animal is used as the animal to be immunized, the immune system of this animal recognizes human GPR49 as a foreign substance. Therefore, human antibodies against human GPR49 can be readily obtained.

The monoclonal antibody-producing hybridomas produced in this manner can be subcultured in a standard medium. Alternatively, the hybridomas can be stored for long periods in liquid nitrogen.

The hybridomas can be cultured according to a standard method, and the desired monoclonal antibody can be obtained from the culture supernatants. Alternatively, the hybridomas can be grown by administering them to a compatible mammal, and monoclonal antibodies can be obtained as its ascites. The former method is suitable for obtaining highly-pure antibodies.

In the present invention, an antibody encoded by an antibody gene cloned from antibody-producing cells can be used. The cloned antibody gene can be incorporated into a suitable vector and then transfected into a host to express the antibody. Methods for isolating an antibody gene, introducing the gene into a vector, and transforming host cells have been established (see for example, Vandamme, A. M. et al., Eur. J. Biochem. (1990) 192, 767-775).

For example, a cDNA encoding the variable region (V region) of an anti-GPR49 antibody can be obtained from hybridoma producing the anti-GPR49 antibody. Generally in order to obtain the cDNA, first, total RNA is extracted from the hybridoma. For example, the following methods can be used as methods for extracting mRNA from cells:
the guanidine ultracentrifugation method (Chirgwin, J. M. et al., Biochemistry (1979) 18, 5294-5299); and the AGPC method (Chomczynski, P. et al., Anal. Biochem. (1987) 162, 156-159).

The extracted mRNA can be purified using an mRNA Purification Kit (GE Healthcare Bio-Sciences) or the like. Alternatively, kits for directly extracting total mRNA from cells such as the QuickPrep mRNA Purification Kit (GE Healthcare Bio-Sciences) are also commercially available. Total mRNA can be obtained from the hybridoma by using such kits. A cDNA encoding the antibody V region can be synthesized from the obtained mRNA using reverse transcriptase. Any of the 15- to 30-nucleotide sequences selected from sequences common among mouse antibody genes can be used as primers. Specifically, a cDNA encoding the antibody V region can be obtained by using primers comprising the DNA sequences shown in SEQ ID NOs: 61 to 63. cDNAs can be synthesized using the AMV Reverse Transcriptase First-strand cDNA Synthesis Kit (SEIKAGAKU CORPORATION) or the like. To synthesize and amplify cDNAs, the 5'-Ampli FINDER RACE Kit (manufactured by Clontech) and the 5'-RACE method using PCR (Frohman, M. A. et al., Proc. Natl. Acad. Sci. USA (1988) 85, 8998-9002; Belyaysky, A. et al., Nucleic Acids Res. (1989) 17, 2919-2932) can be used. Furthermore, in the process of such cDNA synthesis, appropriate restriction enzyme sites, which will be described later, can be introduced into both ends of the cDNA.

The cDNA fragment of interest is purified from the obtained PCR product, and then ligated to a vector DNA. The recombinant vector is prepared in this manner and transformed into *Escherichia coli* or the like, and after colonies are selected, the desired recombinant vector can be prepared from the *E. coli* that formed the colonies. The nucleotide sequence of the cDNA can be confirmed by a known method, such as the dideoxynucleotide chain termination method.

Alternatively, in order to obtain genes encoding the antibody variable regions, a cDNA library can be used. First, a cDNA library is obtained by synthesizing cDNAs from the mRNAs extracted from the antibody-producing cells as templates. It is convenient to use a commercially available kit for cDNA library synthesis. In practice, since the amount of mRNA obtainable from only a small number of cells is extremely minute, the yield of such mRNA from direct purification is low. Therefore, purification is usually performed after adding a carrier RNA that clearly does not contain an antibody gene. Alternatively, when a certain amount of RNA can be extracted, efficient extraction can be accomplished by using the RNA of antibody-producing cells alone. For example, addition of carrier RNA may not be required when RNA is extracted from ten or more, 30 or more, or preferably 50 or more antibody-producing cells.

The antibody genes are amplified by the PCR method using the obtained cDNA library as a template. The primers used for amplification of the antibody genes by the PCR method are known. For example, primers for human antibody gene amplification can be designed based on the disclosure of an article (J. Mol. Biol. (1991) 222, 581-597) and the like. The nucleotide sequences of these primers vary depending on the immunoglobulin subclass. Therefore, when a cDNA library of an unknown subclass is used as the template, the PCR method is performed considering all possibilities.

More specifically, for example, for obtaining genes encoding human IgG, one may use primers capable of amplifying genes encoding γ1 to γ5 for the heavy chain, and genes encoding the κ chain and λ chain for the light chain. To amplify genes of the IgG variable region, generally, a primer that anneals to the portion corresponding to the hinge region is used as the 3'-end primer. Meanwhile, a primer corresponding to each subclass can be used as the 5'-end primer.

PCR products obtained by the primers for gene amplification of the heavy chain and light chain subclasses are made into independent libraries. Using the libraries synthesized in this manner, immunoglobulins comprising a combination of heavy and light chains can be reconstituted. The antibodies of interest can be screened by using the GPR49-binding activity of the reconstituted immunoglobulins as an index.

For example, for obtaining antibodies against GPR49, it is more preferable that the binding of the antibodies to GPR49 is specific. For instance, it is possible to screen for antibodies that bind to GPR49 according to the following steps of:
(1) contacting GPR49 with an antibody comprising a V region encoded by an obtained cDNA;
(2) detecting the binding between GPR49 and the antibody; and
(3) selecting the antibody that binds to GPR49.

Methods for detecting the binding between an antibody and GPR49 are known. Specifically, a test antibody is reacted with carrier-immobilized GPR49, and then this is reacted with a labeled antibody that recognizes the test antibody. If the labeled antibody on the carrier is detected after washing, binding of the test antibody to GPR49 is proved. For labeling, enzymatically active proteins such as peroxidase or β-galactosidase or fluorescent substances such as FITC can be used. In order to evaluate the binding activity of the antibody, fixed samples of GPR49-expressing cells can be used.

For an antibody screening method that uses the binding activity as an index, a phage vector-based panning method may also be used. When the antibody genes are obtained as libraries of the heavy-chain and light-chain subclasses as described above, phage vector-based screening methods are advantageous. Genes encoding variable regions of the heavy and light chains can be made into a single-chain Fv (scFv) gene by linking the genes via suitable linker sequences. Phages expressing an scFv on their surface can be obtained by inserting a gene encoding the scFv into a phage vector. DNA encoding an scFv having the desired binding activity can be collected by contacting the phage with the antigen and then collecting antigen-bound phage. scFv having the desired binding activity can be concentrated by repeating this operation as necessary.

A polynucleotide encoding an antibody of the present invention may encode a full-length antibody or a portion of the antibody. "A portion of an antibody" refers to any portion of an antibody molecule. Hereinafter, the term "antibody fragment" may be used to refer to a portion of an antibody. A preferred antibody fragment of the present invention comprises the complementarity determination region (CDR) of an antibody. More preferably, an antibody fragment of the present invention comprises all of the three CDRs that constitute a variable region.

Once a cDNA encoding a V region of an objective anti-GPR49 antibody is obtained, this cDNA is digested with restriction enzymes that recognize the restriction enzyme sites inserted to both ends of the cDNA. A preferred restriction enzyme is an enzyme that recognizes and digests a nucleotide sequence that is less likely to appear in the nucleotide sequence constituting the antibody gene. Furthermore, to insert a single copy of the digested fragment into a vector in a correct direction, a restriction enzyme that provides sticky ends is preferred. A cDNA encoding the anti-GPR49 antibody V region, which has been digested as described above, is inserted into a suitable expression vector to obtain the antibody expression vector. In this step, a chimeric antibody can be obtained by fusing a gene encoding the antibody constant region (C region) with the above-mentioned gene encoding the V region in frame. Herein, "chimeric antibody" refers to an antibody whose constant and variable regions are derived from different origins. Therefore, in addition to heterogeneous chimeric antibodies such as mouse-human chimeric antibodies, human-human homogeneous chimeric antibodies are also included in the chimeric antibodies of the present invention. A chimeric antibody expression vector can also be constructed by inserting the V region gene into an expression vector into which a DNA encoding a constant region has been incorporated in advance.

More specifically, for example, a restriction enzyme recognition sequence for a restriction enzyme that digests the V-region gene can be placed at the 5' end of an expression vector carrying a DNA encoding a desired antibody constant region (C region). The chimeric antibody expression vector is constructed by digesting both genes using the same combination of restriction enzymes, and fusing them in frame.

To produce an anti-GPR49 antibody for use in the present invention, the antibody gene can be incorporated into an expression vector so that it is expressed under the control of an expression regulatory region. The expression regulatory region for antibody expression includes, for example, an enhancer or a promoter. Then, by transforming suitable host cells with this expression vector, recombinant cells that express the DNA encoding the anti-GPR49 antibody can be obtained.

To express an antibody gene, a DNA encoding the antibody heavy chain (H chain) and a DNA encoding the antibody light chain (L chain) can be incorporated into different expression vectors. An antibody molecule comprising the H chain and L chain can be expressed by co-transfecting the vectors incorporating the H chain and L chain into the same host cell. Alternatively, DNAs encoding the H chain and L chain can be incorporated into a single expression vector to transform a host cell with the vector (see International Patent Publication No. WO 94/11523).

Many combinations of hosts and expression vectors for transfecting an isolated antibody gene into an appropriate host to prepare the antibody are known. Any of these expression systems can be applied to the present invention. For using eukaryotic cells as a host, animal cells, plant cells, or fungal cells can be used. More specifically, animal cells that may be used in the present invention are, for example, the following cells:
(1) mammalian cells: CHO, COS, myeloma, baby hamster kidney (BHK), HeLa, Vero, HEK293, Ba/F3, HL-60, Jurkat, SK-HEP1 cells, or such;
(2) amphibian cells: Xenopus oocytes, or such; and
(3) insect cells: sf9, sf21, Tn5, or such.

In addition, as a plant cell, an antibody gene expression system using cells derived from the *Nicotiana* genus such as *Nicotiana tabacum* is known. Callus cultured cells can be used to transform plant cells.

Furthermore, the following cells can be used as fungal cells:
yeasts: the *Saccharomyces* genus such as *Saccharomyces cerevisiae*, and the *Pichia* genus such as *Pichia pastoris*; and filamentous fungi: the *Aspergillus* genus such as *Aspergillus niger*.

Alternatively, antibody gene expression systems that utilize prokaryotic cells are also known. For example, when using bacterial cells, *E. coli* cells, *Bacillus subtilis* cells, and such may be utilized in the present invention.

In the case of mammalian cells, the antibody genes can be expressed by operably linking the antibody gene to be expressed with an effective commonly used promoter, and a polyA signal on the 3' downstream side of the antibody gene. An example of the promoter/enhancer includes human cytomegalovirus immediate early promoter/enhancer.

Other promoters/enhancers that can be used for antibody expression include viral promoters/enhancers, or mammalian cell-derived promoters/enhancers such as human elongation factor 1α (HEF1α). Specific examples of viruses whose promoters/enhancers may be used include retrovirus, polyoma virus, adenovirus, and simian virus 40 (SV40).

When an SV40 promoter/enhancer is used, the method of Mulligan et al. (Nature (1979) 277, 108) may be utilized. An HEF1α promoter/enhancer can be readily used for expressing a gene of interest by the method of Mizushima et al. (Nucleic Acids Res. (1990) 18, 5322).

When *E. coli* is used, the antibody genes can be expressed by operably linking the gene to be expressed to a conventional useful promoter and a signal sequence for antibody secretion. Such promoters include, for example, the lacZ promoter and the araB promoter. When the lacZ promoter is used, it is possible to use the method of Ward et al. (Nature (1989) 341: 544-546; FASEB J. (1992) 6: 2422-2427). Alternatively, when the araB promoter is used to express the gene, it is possible to use the method of Better et al. (Science (1988) 240: 1041-1043).

When the antibodies are produced into the periplasm of *E. coli*, the pelB signal sequence (Lei S. P. et al., J. Bacteriol. (1987) 169: 4379) may be used as a signal sequence for antibody secretion. After the antibody produced in the periplasm is isolated, the antibody structure is refolded by using a protein denaturant like urea or guanidine hydrochloride so that the antibody will have the desired binding activity.

When the antibody is produced using animal cells, it is desirable to use an antibody heavy-chain gene or light-chain gene signal sequence as the signal sequence necessary for secreting antibody outside the cell. Alternatively the signal sequence carried by a secretory protein such as IL-3 and IL-6 can be used.

The replication origin inserted into the expression vector includes, for example, those derived from SV40, polyoma virus, adenovirus, or bovine papilloma virus (BPV). Furthermore, in order to amplify the gene copy number in the host cell system, a selection marker can be inserted into the expression vector. Specifically, the following selection markers can be used:
aminoglycoside transferase (APH) gene;
thymidine kinase (TK) gene;
*E. coli* xanthine guanine phosphoribosyltransferase (Ecogpt) gene;
dihydrofolate reductase (dhfr) gene, etc.

These expression vectors are transfected into host cells, and then, the transformed host cells are cultured in vitro or in vivo to induce production of the desired antibody. The host cells are cultured according to known methods. For example, DMEM, MEM, RPMI1640, or IMDM can be used as the culture medium. A serum supplement solution such as fetal calf serum (FCS) can also be used in combination.

Antibodies expressed and produced as described above can be purified by using a single known method or a suitable combination of known methods generally used for purifying proteins. Antibodies can be isolated and purified by, for example, appropriately selecting and combining affinity columns such as protein A column, chromatography column, filtration, ultrafiltration, salt precipitation, dialysis, and such (Antibodies A Laboratory Manual. Ed Harlow, David Lane, Cold Spring Harbor Laboratory, 1988).

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat β-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be used on the transgenic goat as necessary (Ebert, K. M. et all, Bio/Technology (1994) 12, 699-702).

Non-human animal antibody-derived C regions can be used for the C regions of a recombinant antibody of the present invention. For example, Cγ1, Cγ2a, Cγ2b, Cγ3, Cµ, Cδ, Cα1, Cα2, and Cε can be used for the mouse antibody H chain C region, and Cκ and Cλ can be used for the L chain C region. In addition to mouse antibodies, antibodies of rats, rabbits, goats, sheep, camels, monkeys, and such can be used as animal antibodies. Their sequences are known. Furthermore, the C region can be modified to improve the stability of the antibodies or their production.

In the present invention, when antibodies are administered to humans, recombinant antibodies that have been artificially modified for the purpose of reducing xenoantigenicity against humans, or the like can be used. Examples of the recombinant antibodies include chimeric antibodies and humanized antibodies. These modified antibodies can be produced using known methods.

A chimeric antibody is an antibody whose variable regions and constant regions of different origins are linked. For example, an antibody comprising the heavy chain and light chain variable regions of a mouse antibody and the heavy chain and light chain constant regions of a human antibody is a mouse-human heterogeneous chimeric antibody. A recombinant vector expressing a chimeric antibody can be prepared by linking a DNA encoding a mouse antibody variable region to a DNA encoding a human antibody constant region, and then inserting it into an expression vector. The recombinant cells that have been transformed with the vector are cultured, and the integrated DNA is expressed to obtain the chimeric antibody produced in the culture. Human antibody C regions are used for the C regions of chimeric antibodies and humanized antibodies.

For example, Cγ1, Cγ2, Cγ3, Cγ4, Cμ, Cδ, Cα1, Cα2, and Cε can be used as an H chain C region. Cκ and Cλ, can be used as an L chain C region. The amino acid sequences of these C regions and the nucleotide sequences encoding them are known. Furthermore, the human antibody C regions can be modified to improve the stability of an antibody itself or production thereof.

Generally, a chimeric antibody is composed of V regions of an antibody derived from a non-human animal and C regions derived from a human antibody. On the other hand, a humanized antibody consists of the complementarity determining region (CDR) of an antibody derived from a non-human animal, and the framework region (FR) and C region derived from a human antibody. Since the antigenicity of a humanized antibody in human body is reduced, a humanized antibody is useful as an active ingredient for therapeutic agents of the present invention.

The antibody variable region is generally composed of three complementarity determining regions (CDRs) separated by four framework regions (FRs). CDR is a region that substantially determines the binding specificity of an antibody. The amino acid sequences of CDRs are highly diverse. On the other hand, the FR-constituting amino acid sequences are often highly homologous even among antibodies with different binding specificities. Therefore, generally, the binding specificity of a certain antibody can be introduced to another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known.

Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that is highly homologous to a mouse FR is advantageous for maintaining the CDR function. That is, it is generally preferable to use a human FR comprising an amino acid sequence highly homologous to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 96/02576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Sato, K. et al., Cancer Res. (1993) 53: 851-856).

Methods for obtaining human antibodies are also known. For example, human lymphocytes are sensitized in vitro with a desired antigen or cells expressing a desired antigen. Then, by fusing the sensitized lymphocytes with human myeloma cells, desired human antibodies having the antigen-binding activity can be obtained (see JP-B H01-59878). U266 or such can be used as the fusion partner human myeloma cell.

Alternatively, a desired human antibody can be obtained by using a desired antigen to immunize a transgenic animal that includes the entire repertoire of human antibody genes (see International Patent Publication Nos. WO 93/12227, WO 92/03918, WO 94/02602, WO 94/25585, WO 96/34096, and WO 96/33735). Furthermore, techniques to obtain human antibodies by panning a human antibody library are also known. For example, the human antibody V region is expressed as a single-chain antibody (scFv) on the surface of a phage using a phage display method, and phages that bind to the antigen can be selected. By analyzing the genes of selected phages, the DNA sequences encoding the human antibody V regions that bind to the antigen can be determined. After determining the DNA sequences of scFvs that bind to the antigen, the V region sequence is fused in frame with the desired human antibody C region sequence, and this is inserted into a suitable expression vector to produce an expression vector. This expression vector can be transfected into suitable expression cells such as those described above, and the gene encoding the human antibody can be expressed to obtain the human antibodies. Such methods are already known (International Patent Publication Nos. WO 92/01047, WO 92/20791, WO 93/06213, WO 93/11236, WO 93/19172, WO 95/01438, and WO 95/15388).

Therefore, an example of preferred embodiments of the antibody used in the present invention is an antibody comprising a human constant region.

The antibodies of the present invention are not limited to bivalent antibodies represented by IgG, but include monovalent antibodies and multivalent antibodies represented by IgM, as long as it binds to the GPR49 protein. The multivalent antibodies of the present invention include multivalent antibodies that have the same antigen binding sites, and multivalent antibodies that have partially or completely different antigen binding sites. The antibodies of the present invention are not limited to whole antibody molecules, but include minibodies and modified products thereof, as long as they bind to the GPR49 protein.

The minibodies comprise antibody fragments lacking portions of the whole antibody (for example, whole IgG). The minibodies may lack portions of antibody molecules as long as they have binding activity to GPR49 antigens. Antibody fragments of the present invention preferably contain either heavy chain variable regions (VH) or light chain variable regions (VL), or both, and preferably contain CDRs. The amino acid sequences of VH or VL may contain substitutions, deletions, additions and/or insertions. Furthermore, the antibody fragment may also lack portions of either VH or VL, or both, as long as it has binding ability to GPR49 antigen. In addition, the variable regions may be chimerized or humanized. Such antibody fragments include, for example, Fab, Fab', F(ab')$_2$, and Fv. An example of a minibody includes Fab, Fab', F(ab')$_2$, Fv, scFv (single-chain Fv), diabody, and sc(Fv)$_2$ (single-chain (Fv)$_2$), scFv-Fc. Multimers of these antibodies (for example, dimers, trimers, tetramers, and polymers) are also included in the minibodies of the present invention.

Antibody fragments can be obtained by treating an antibody with enzymes to produce antibody fragments. Known enzymes that produce antibody fragments are, for example, papain, pepsin, and plasmin. Alternatively, genes encoding these antibody fragments can be constructed and introduced into expression vectors to express them in appropriate host cells (see, for example, Co, M. S. et al., J. Immunol. (1994) 152, 2968-2976; Better, M. and Horwitz, A. H., Methods in Enzymology (1989) 178, 476-496; Plueckthun, A. and Skerra, A., Methods in Enzymology (1989) 178, 476-496; Lamoyi, E., Methods in Enzymology (1989) 121, 652-663; Rousseaux, J. et al., Methods in Enzymology (1989) 121, 663-669; and Bird, R. E. et al., TIBTECH (1991) 9, 132-137).

Digestive enzymes cleave specific sites of an antibody fragment, and yield antibody fragments with the following specific structures. When genetic engineering techniques are used on such enzymatically obtained antibody fragments, any portion of the antibody can be deleted.

Papain digestion: F(ab)$_2$ or Fab
Pepsin digestion: F(ab')$_2$ or Fab'
Plasmin digestion: Facb Therefore, minibodies of the present invention may be antibody fragments lacking any region, as long as they have binding affinity to GPR49. Furthermore, according to the present invention, the antibodies desirably maintain their effector activity, particularly in the treatment of cell proliferative diseases such as cancer. More specifically, preferred minibodies of the present invention have both binding affinity to GPR49 and effector function. The effector function of antibodies includes ADCC activity and CDC activity. Particularly preferably, therapeutic antibodies of the present invention have either ADCC activity or CDC activity, or both, as effector function.

The term "diabody" refers to a bivalent antibody fragment constructed by gene fusion (Holliger P et al., 1993, Proc. Natl. Acad. Sci. USA 90: 6444-6448; EP 404,097; WO 93/11161 and others). Diabodies are dimers comprising two polypeptide chains, where each polypeptide chain consisting dimer comprises a VL and a VH connected with a linker. The linker of diabody is short enough to prevent interaction of these two domains. Specifically, amino acid residues comprising a linker is, for example, about five residues. Therefore, the VL and VH encoded on the same polypeptide chain cannot form a single-chain variable region fragment, and will form a dimer with other single-chain variable region fragment. As a result, the diabody has two antigen binding sites.

scFv can be obtained by ligating the H chain V region and L chain V region of an antibody. In scFv, the H chain V region and L chain V region are ligated via a linker, preferably a peptide linker (Huston, J. S. et al., Proc. Natl. Acad. Sci. U.S.A., 1988, 85, 5879-5883). The H chain V region and L chain V region of scFv may be derived from any of the antibodies described herein. The peptide linker for ligating the V regions is not particularly limited. For example, any single-chain peptide consisting of 3 to 25 residues or so can be used as the linker. More specifically, for example, peptide linkers described below or such can be used.

PCR methods such as those described above can be used for ligating the V regions from both chains. For ligation of the V regions by PCR methods, first, a whole DNA or a DNA encoding a desired partial amino acid sequence selected from the following DNAs can be used as a template:

a DNA sequence encoding the H chain or the H chain V region of the antibody; and a DNA sequence encoding the L chain or the L chain V region of the antibody.

DNAs encoding the H chain and L chain V regions are individually amplified by PCR methods using a pair of primers that have sequences corresponding to the sequences of both ends of the DNAs to be amplified. Then, a DNA encoding the peptide linker portion is prepared. The DNA encoding the peptide linker can also be synthesized using PCR. To the 5' end of the primers used, nucleotide sequences that can be ligated to each of the individually synthesized V region amplification products are added. Next, PCR reaction is carried out using each of the [H-chain V region DNA], [peptide linker DNA], and [L-chain V region DNA], and the primers for assembly PCR.

The primers for assembly PCR consist of a combination of a primer that anneals to the 5' end of the [H chain V region DNA] and a primer that anneals to the 3' end of the [L chain V region DNA]. That is, the primers for assembly PCR are a primer set that can amplify a DNA encoding the full-length sequence of scFv to be synthesized. On the other hand, nucleotide sequences that can be ligated to each V-region DNA are added to the [peptide linker DNA]. These DNAs are then ligated, and the full-length scFv is finally produced as an amplification product using the primers for assembly PCR. Once the scFv-encoding DNA is constructed, expression vectors containing the DNA, and recombinant cells transformed with these expression vectors can be obtained according to conventional methods. Furthermore, the scFvs can be obtained by culturing the resulting recombinant cells and expressing the DNA encoding scFv.

scFv-Fc is a minibody prepared by connecting an Fc region with an scFv comprising the H chain V region and L chain V region of an antibody (Cellular & Molecular Immunology 2006; 3: 439-443). The origin of the scFv used in scFv-Fc is not particularly limited, and for example, IgM-derived scFv may be used. Furthermore, the origin of Fc is not particularly limited, and for example, mouse IgG2 (mouse IgG2a or such), and human IgG (human IgG1 or such) may be used. Therefore, examples of preferred embodiments of scFv-Fc include scFv-Fc produced by ligating the IgM antibody scFv fragment and the mouse IgG2a CH2 (for example Cγ2) and CH3 (for example Cγ3) using the mouse IgG2a hinge region (Hγ), and scFv-Fc produced by ligating the IgM antibody scFv fragment and the human IgG1 CH2 and CH3 using the human IgG1 hinge region.

sc(Fv)$_2$ is a single-chain minibody produced by linking two units of VH and two units of VL with linkers and such (Hudson et al., 1999, J Immunol. Methods 231:177-189). sc(Fv)2 can be produced, for example, by linking two scFv molecules.

In a preferable antibody, the two VH units and two VL units are arranged in the order of VH, VL, VH, and VL ([VH]- linker-[VL]-linker-[VH]-linker-[VL]) beginning from the N terminus of a single-chain polypeptide.

The order of the two VH units and two VL units is not limited to the above arrangement, and they may be arranged in any order. Examples of the arrangements are listed below.
[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

The linkers to be used for linking the variable regions of an antibody comprise arbitrary peptide linkers that can be introduced by genetic engineering, synthetic linkers, and linkers disclosed in, for example, Protein Engineering, 9(3), 299-305, 1996. Peptide linkers are preferred in the present invention. There are no limitations as to the length of the peptide linkers. The length can be selected accordingly by those skilled in the art depending on the purpose, and amino acid residues comprising peptide linker is typically 1 to 100 amino acids, preferably 3 to 50 amino acids, more preferably 5 to 30 amino acids, and even more preferably 12 to 18 amino acids (for example, 15 amino acids).

Amino acid sequences of the peptide linkers comprise arbitrary sequences as long as they do not inhibit the scFv binding ability. For example, such peptide linkers include:

```
Ser

Gly-Ser

Gly-Gly-Ser

Ser-Gly-Gly

Gly-Gly-Gly-Ser              (SEQ ID NO: 53)

Ser-Gly-Gly-Gly              (SEQ ID NO: 54)

Gly-Gly-Gly-Gly-Ser          (SEQ ID NO: 55)

Ser-Gly-Gly-Gly-Gly          (SEQ ID NO: 56)

Gly-Gly-Gly-Gly-Gly-Ser      (SEQ ID NO: 57)

Ser-Gly-Gly-Gly-Gly-Gly      (SEQ ID NO: 58)

Gly-Gly-Gly-Gly-Gly-Gly-Ser  (SEQ ID NO: 59)

Ser-Gly-Gly-Gly-Gly-Gly-Gly  (SEQ ID NO: 60)

(Gly-Gly-Gly-Gly-Ser         (SEQ ID NO: 53))n (Ser-Gly-Gly-Gly-Gly         (SEQ ID NO: 54))n
``` where n is an integer of 1 or larger.

The amino acid sequences of peptide linkers can be selected accordingly by those skilled in the art depending on the purpose. For example, "n", which determines the length of peptide linker described above, is typically 1 to 5, preferably 1 to 3, or more preferably 1 or 2.

In an embodiment of the present invention, a particularly preferable sc(Fv)2 includes, for example, the sc(Fv)2 below.
[VH]-peptide linker (15 amino acids)-[VL]-peptide linker (15 amino acids)-[VH]-peptide linker (15 amino acids)-[VL]

Alternatively, V regions can be crosslinked using synthetic linkers (chemical crosslinking agents). Crosslinking agents routinely used to crosslink peptide compounds can be used in the present invention. For example, chemical crosslinking agents such as the following is known. These crosslinking agents are commercially available.

N-hydroxy succinimide (NHS),
disuccinimidyl suberate (DSS),
bis(sulfosuccinimidyl) suberate ($BS^3$),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl]sulfone (BSOCOES),
and bis[2-(sulfosuccinimidoxycarbonyloxy)ethyl]sulfone (sulfo-BSOCOES).

In general, three linkers are required to link four antibody variable regions together. The linkers to be used may be of the same type or different types. In the present invention, a preferable minibody is a diabody or an sc(Fv)$_2$. Such a minibody can be prepared by treating an antibody with an enzyme, for example, papain or pepsin, to generate antibody fragments, or by constructing DNAs encoding those antibody fragments and introducing them into expression vectors, followed by expression in an appropriate host cell (see, for example, Co, M. S. et al., 1994, J. Immunol. 152, 2968-2976; Better, M. and Horwitz, A. H., 1989, Methods Enzymol. 178, 476-496; Pluckthun, A. and Skerra, A., 1989, Methods Enzymol. 178, 497-515; Lamoyi, E., 1986, Methods Enzymol. 121, 652-663; Rousseaux, J. et al., 1986, Methods Enzymol. 121, 663-669; Bird, R. E. and Walker, B. W., 1991, Trends Biotechnol. 9, 132-137).

Furthermore, the antibodies of the present invention include not only monovalent antibodies but also multivalent antibodies. Multivalent antibodies of the present invention include multivalent antibodies whose antigen binding sites are all the same and multivalent antibodies whose antigen binding sites are partially or completely different.

Antibodies conjugated to various types of molecules such as polyethylene glycol (PEG) can also be used as modified antibodies. Moreover, cytotoxic substances such as chemotherapeutic agents, toxic peptides, or radioactive chemical substances can be conjugated to the antibodies. Such modified antibodies (hereinafter referred to as antibody conjugates) can be obtained by chemically-modifying the obtained antibodies. Methods for modifying antibodies are already established in this field. Furthermore, as described below, such antibodies can also be obtained in the molecular form of a bispecific antibody designed using genetic engineering techniques to recognize not only GPR49 proteins, but also cytotoxic substances such as chemotherapeutic agents, toxic peptides, and radioactive chemical substances. These antibodies are also included in the "antibodies" of the present invention.

Chemotherapeutic agents that are linked to anti-GPR49 antibodies to exert an cytotoxic activity include the following: azaribine, anastrozole, azacytidine, bleomycin, bortezomib, bryostatin-1, busulfan, camptothecin, 10-hydroxycamptothecin, carmustine, CELEBREX™, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, Ifosfamide, leucovorin, lomustine, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, TAXOL™, testosterone propionate, thalidomide, thioguanine, THIOTEPA™, teniposide, topotecan, uracil mustard, vinblastine, vinorelbine, and vincristine.

In the present invention, preferred chemotherapeutic agents are low-molecular-weight chemotherapeutic agents. Low-molecular-weight chemotherapeutic agents are unlikely to interfere with antibody function even after binding to antibodies. In the present invention, low-molecular-weight chemotherapeutic agents usually have a molecular weight of 100 to 2,000, preferably 200 to 1,000. The chemotherapeutic agents exemplified herein are all low-molecular-weight chemotherapeutic agents. The chemotherapeutic agents of the present invention include prodrugs that are converted to active chemotherapeutic agents in vivo. Prodrug activations may be enzymatic conversion or non-enzymatic conversion.

Furthermore, the antibodies can be modified using toxic peptides. Examples of toxic peptides include the following: Diphtheria toxin A Chain (Langone J. J., et al., Methods in Enzymology, 93, 307-308, 1983), *Pseudomonas* Exotoxin (Nature Medicine, 2, 350-353, 1996), Ricin A Chain (Fulton R. J., et al., J. Biol. Chem., 261, 5314-5319, 1986; Sivam G., et al., Cancer Res., 47, 3169-3173, 1987; Cumber A. J. et al., J. Immunol. Methods, 135, 15-24, 1990; Wawrzynczak E. J., et al., Cancer Res., 50, 7519-7562, 1990; Gheeite V., et al., J. Immunol. Methods, 142, 223-230, 1991), Deglicosylated Ricin A Chain (Thorpe P. E., et al., Cancer Res., 47, 5924-5931, 1987), Abrin A Chain (Wawrzynczak E. J., et al., Br. J. Cancer, 66, 361-366, 1992; Wawrzynczak E. J., et al., Cancer Res., 50, 7519-7562, 1990; Sivam G., et al., Cancer Res., 47, 3169-3173, 1987; Thorpe P. E., et al., Cancer Res., 47, 5924-5931, 1987), Gelonin (Sivam G., et al., Cancer Res., 47, 3169-3173, 1987; Cumber A. J. et al., J. Immunol. Methods, 135, 15-24, 1990; Wawrzynczak E. J., et al., Cancer Res., 50, 7519-7562, 1990; Bolognesi A., et al., Clin. exp. Immunol., 89, 341-346, 1992), PAP-s; Pokeweed anti-viral protein from seeds (Bolognesi A., et al., Clin. exp. Immunol., 89, 341-346, 1992), Briodin (Bolognesi A., et al., Clin. exp. Immunol., 89, 341-346, 1992), Saporin (Bolognesi A., et al., Clin. exp. Immunol., 89, 341-346, 1992), Momordin (Cumber A. J., et al., J. Immunol. Methods, 135, 15-24, 1990; Wawrzynczak E. J., et al., Cancer Res., 50, 7519-7562, 1990; Bolognesi A., et al., Clin. exp. Immunol., 89, 341-346, 1992), Momorcochin (Bolognesi A., et al., Clin. exp. Immunol., 89, 341-346, 1992), Dianthin 32 (Bolognesi A., et al., Clin. exp. Immunol., 89, 341-346, 1992), Dianthin 30 (Stirpe F., Barbieri L., FEBS letter 195, 1-8, 1986), Modeccin (Stirpe F., Barbieri L., FEBS letter 195, 1-8, 1986), Viscumin (Stirpe F., Barbieri L., FEBS letter 195, 1-8, 1986), Volkesin (Stirpe F., Barbieri L., FEBS letter 195, 1-8, 1986), Dodecandrin (Stirpe F., Barbieri L., FEBS letter 195, 1-8, 1986), Tritin (Stirpe F., Barbieri L., FEBS letter 195, 1-8, 1986), Luffin (Stirpe F., Barbieri L., FEBS letter 195, 1-8, 1986), or Trichokirin (Casellas P., et al., Eur. J. Biochem. 176, 581-588, 1988; Bolognesi A., et al., Clin. exp. Immunol., 89, 341-346, 1992).

A radioactive chemical substance in the present invention refers to a chemical substance comprising a radioisotope. The radioisotope is not particularly limited, and any radioisotope may be used, but for example, $^{32}P$, $^{14}C$, $^{125}I$, $^{3}H$, $^{131}I$, $^{186}Re$, $^{188}Re$, and such may be used. In another embodiment one, two, or more of the low-molecular-weight chemotherapeutic agents and toxic peptides can be combined and used for antibody modification. The bonding between an anti-GPR49 antibody and the above-mentioned low-molecular-weight chemotherapeutic agent may be covalent bonding or non-covalent bonding. Methods for producing antibodies bound to these chemotherapeutic agents are known.

Furthermore, proteinaceous pharmaceutical agents or toxins can be bound to antibodies by genetic engineering techniques. Specifically, for example, it is possible to construct a recombinant vector by fusing a DNA encoding the above-mentioned toxic peptide with a DNA encoding an anti-GPR49 antibody in frame, and inserting this into an expression vector. This vector is transfected into suitable host cells, the obtained transformed cells are cultured, and the incorporated DNA is expressed. Thus an anti-GPR49 antibody conjugated to the toxic peptide can be obtained as a fusion protein. When obtaining an antibody as a fusion protein, the proteinaceous pharmaceutical agent or toxin is generally positioned at the C-terminus of the antibody. A peptide linker can be positioned between the antibody and the proteinaceous pharmaceutical agent or toxin.

Furthermore, the antibody of the present invention may be a bispecific antibody. A bispecific antibody refers to an antibody that carries variable regions that recognize different epitopes within the same antibody molecule. In the present invention, the bispecific antibody may have antigen-binding sites that recognize different epitopes on a GPR49 molecule. Two molecules of such a bispecific antibody can bind to one molecule of GPR49. As a result, stronger cytotoxic action can be expected.

Alternatively, the bispecific antibody may be an antibody in which one antigen-binding site recognizes GPR49, and the other antigen-binding site recognizes a cytotoxic substance. Specifically, cytotoxic substances include chemotherapeutic agents, toxic peptides, and radioactive chemical substances. Such a bispecific antibody binds to GPR49-expressing cells, and at the same time, captures cytotoxic substances. This enables the cytotoxic substances to directly act on GPR49-expressing cells. Therefore, bispecific antibodies that recognize cytotoxic substance can specifically injure tumor cells and suppress tumor cell proliferation.

Furthermore, in the present invention, bispecific antibodies that recognize antigens other than GPR49 may be combined. For example, it is possible to combine bispecific antibodies that recognize non-GPR49 specifically expressed on the surface of target cancer cells like GPR49.

Methods for producing bispecific antibodies are known. For example, two types of antibodies recognizing different antigens may be linked to prepare a bispecific antibody. The antibodies to be linked may be half molecules each having an H chain or an L chain, or may be quarter molecules consisting of only an H chain. Alternatively, bispecific antibody-producing fused cells can be prepared by fusing hybridomas producing different monoclonal antibodies. Bispecific antibodies can also be prepared by genetic engineering techniques.

Known means can be used to measure the antigen-binding activity of the antibodies (Antibodies A Laboratory Manual. Ed Harlow, David Lane, Cold Spring Harbor Laboratory, 1988). For example, an enzyme linked immunosorbent assay (ELISA), an enzyme immunoassay (EIA), a radioimmunoassay (RIA), or a fluoroimmunoassay can be used.

The antibodies of the present invention may be antibodies with modified sugar chains. It is known that the cytotoxic activity of an antibody can be increased by modifying its sugar chain. Known antibodies having modified sugar chains include the following:
glycosylated antibodies (for example, WO 99/54342);
antibodies with defucosylated sugar chains (for example, WO 00/61739 and WO 02/31140);
antibodies having a sugar chain with bisecting GlcNAc (for example, WO 02/79255); etc.

Whether or not an antibody has cell proliferation-inhibiting activity against cells that express GPR49 proteins can be measured by a method known to those skilled in the art. For example, cell proliferation-inhibiting activity can be measured by culturing cells that expresses GRP49 proteins in the presence or absence (or in the presence of a negative control antibody) of a target antibody, and then counting the number of viable cells. As long as cell proliferation is inhibited, the inhibition ratio is not particularly limited, but preferred examples include the number of viable cells in the presence of the target antibody which is 90% or less, 70% or less, 50% or less, or such compared to the number of viable cells in its absence. Cells that express GRP49 proteins are not particularly limited, but include cells transformed with a gene encoding a GPR49 protein and cells of gastric cancer, colon cancer, hepatocellular carcinoma, lung cancer, ovarian cancer, and glioma.

When using antibodies of the present invention for therapeutic purposes, the antibodies are preferably antibodies having cytotoxic activity.

In the present invention, the cytotoxic activity includes, for example, antibody-dependent cell-mediated cytotoxicity (ADCC) activity and complement-dependent cytotoxicity (CDC) activity. In the present invention, CDC activity refers to complement system-mediated cytotoxic activity. Meanwhile, ADCC activity refers to the activity of damaging a target cell when a specific antibody attaches to its cell surface antigen. An Fcγ receptor-retaining cell (immunocyte or such) binds to the Fc portion of the antibody via the Fcγ receptor and the target cell is damaged.

Whether or not an anti-GPR49 antibody has ADCC activity or CDC activity can be determined by known methods (for example, Current protocols in Immunology, Chapter 7. Immunologic studies in humans, Editor, John E, Coligan et al., John Wiley & Sons, Inc., (1993), etc.).

Specifically, first, effector cells, complement solution, and target cells are prepared.

(1) Preparation of Effector Cells

Spleen is removed from a CBA/N mouse or the like, and spleen cells are isolated in RPMI1640 medium (manufactured by Invitrogen). After washing with the same medium containing 10% fetal bovine serum (FBS, manufactured by HyClone), effector cells with a cell concentration adjusted to $5 \times 10^6$ cells/mL were prepared.

(2) Preparation of Complement Solution

Baby Rabbit Complement (manufactured by CEDARLANE) is diluted 10-fold with a culture medium (manufactured by Invitrogen) containing 10% FBS to prepare a complement solution.

(3) Preparation of Target Cells

GPR49 protein-expressing cells can be radioactively labeled by incubating the target cells with 0.2 mCi of sodium chromate-$^{51}$Cr (manufactured by GE Healthcare Bio-Sciences) in a DMEM medium containing 10% FBS for one hour at 37° C. For GPR49 protein-expressing cells, one may use cells transformed with a gene encoding the GPR49 protein, cells from stomach cancer, colon cancer, liver cell cancer, lung cancer, or ovary cancer, glioma cells, or such. After radioactive labeling, cells are washed three times with RPMI1640 medium containing 10% FBS, and the target cells can be prepared by adjusting the cell concentration to $2 \times 10^5$ cells/mL.

ADCC activity and CDC activity can be measured by the method described below. In the case of ADCC activity measurement, 50 µL of the target cells and 50 µL of the anti-GPR49 antibody are each added to a 96-well U-bottom plate (manufactured by Becton Dickinson), and reacted for 15 minutes on ice. Thereafter, 100 µL of effector cells are added and incubated in a carbon dioxide incubator for four hours. The final concentration of the antibody is adjusted to 0 or 10 µg/mL. After incubation, 100 µL of the supernatant is collected, and radioactivity is measured with a gamma counter (COBRAII AUTO-GAMMA, MODEL D5005, manufactured by Packard Instrument Company). The cytotoxic activity (%) can be calculated using values obtained from the equation $(A-C)/(B-C) \times 100$. A represents the radioactivity (cpm) in each sample, B represents the radioactivity (cpm) in a sample where 1% NP-40 (manufactured by Nacalai Tesque) has been added, and C represents the radioactivity (cpm) of a sample containing the target cells alone.

Meanwhile, in the case of CDC activity measurement, 50 µL of target cell and 50 µL of an anti-GPR49 antibody are added to a 96-well flat-bottom plate (manufactured by Becton Dickinson), and reacted for 15 minutes on ice. Thereafter, 100 µL of the complement solution is added, and incubated in a carbon dioxide incubator for four hours. The final concentration of the antibody is adjusted to 0 or 3 µg/mL. After incubation, 100 µL of supernatant is collected, and the radioactivity is measured with a gamma counter. The cytotoxic activity can be calculated in the same way as in the ADCC activity determination.

On the other hand, in the case of measuring the cytotoxic activity of an antibody conjugate, 50 µL of target cell and 50 µL of an anti-GPR49 antibody conjugate are added to a 96-well flat-bottom plate (manufactured by Becton Dickinson), and reacted for 15 minutes on ice. This is then incubated in a carbon dioxide incubator for one to four hours. The final concentration of the antibody is adjusted to 0 or 3 µg/mL. After incubation, 100 µL of supernatant is collected, and the radioactivity is measured with a gamma counter. The cytotoxic activity can be calculated in the same way as in the ADCC activity determination. An example of other embodiments of an antibody used in the present invention is an antibody having an internalizing activity. In the present invention, "antibody having an internalizing activity" denotes antibody that is transported into a cell (into a cytoplasm, vesicles, other organelles, and such) upon binding to a cell surface GPR49.

Whether or not an antibody has an internalizing activity can be confirmed using methods known to those skilled in the art. For example, the internalizing activity can be confirmed by the method of contacting a label-conjugated anti-GPR49 antibody with GPR49-expressing cells and confirming whether or not the labeled substance was incorporated into the cells, or by the method of contacting a cytotoxic substance-conjugated anti-GPR49 antibody with GPR49-expressing cells and confirming whether or not cell death has been induced in the GPR49-expressing cells. More specifically, whether or not an antibody has an internalizing activity can be confirmed by the method described in the examples provided below.

For example, antibodies having an internalizing activity can be used as pharmaceutical compositions for anticancer agents and such by conjugating them with the above-mentioned cytotoxic substances.

Any GPR49-recognizing antibody can be used as the antibody of the present invention. For example, preferred antibodies include the antibodies of (1) to (20) below. These antibodies may be, for example, full-length antibodies, minibodies, animal antibodies, chimeric antibodies, humanized antibodies, or human antibodies:

(1) an antibody comprising an H chain having the amino acid sequence of SEQ ID NO: 5 as CDR1, the amino acid sequence of SEQ ID NO: 6 as CDR2, and the amino acid sequence of SEQ ID NO: 7 as CDR3;
(2) an antibody comprising an L chain having the amino acid sequence of SEQ ID NO: 10 as CDR1, the amino acid sequence of SEQ ID NO: 11 as CDR2, and the amino acid sequence of SEQ ID NO: 12 as CDR3;
(3) an antibody comprising the H chain of (1) and the L chain of (2);
(4) an antibody comprising an H chain having the amino acid sequence of SEQ ID NO: 15 as CDR1, the amino acid sequence of SEQ ID NO: 16 as CDR2, and the amino acid sequence of SEQ ID NO: 17 as CDR3;
(5) an antibody comprising an L chain having the amino acid sequence of SEQ ID NO: 20 as CDR1, the amino acid sequence of SEQ ID NO: 21 as CDR2, and the amino acid sequence of SEQ ID NO: 22 as CDR3;
(6) an antibody comprising the H chain of (4) and the L chain of (5);
(7) an antibody comprising an H chain having the amino acid sequence of SEQ ID NO: 25 as CDR1, the amino acid sequence of SEQ ID NO: 26 as CDR2, and the amino acid sequence of SEQ ID NO: 27 as CDR3;
(8) an antibody comprising an L chain having the amino acid sequence of SEQ ID NO: 30 as CDR1, the amino acid sequence of SEQ ID NO: 31 as CDR2, and the amino acid sequence of SEQ ID NO: 32 as CDR3;
(9) an antibody comprising the H chain of (7) and the L chain of (8);
(10) an antibody comprising an H chain having the amino acid sequence of SEQ ID NO: 35 as CDR1, the amino acid sequence of SEQ ID NO: 36 as CDR2, and the amino acid sequence of SEQ ID NO: 37 as CDR3;
(11) an antibody comprising an L chain having the amino acid sequence of SEQ ID NO: 40 as CDR1, the amino acid sequence of SEQ ID NO: 41 as CDR2, and the amino acid sequence of SEQ ID NO: 42 as CDR3;
(12) an antibody comprising the H chain of (10) and the L chain of (11);
(13) an antibody comprising an H chain having the amino acid sequence of SEQ ID NO: 45 as CDR1, the amino acid sequence of SEQ ID NO: 46 as CDR2, and the amino acid sequence of SEQ ID NO: 47 as CDR3;
(14) an antibody comprising an L chain having the amino acid sequence of SEQ ID NO: 50 as CDR1, the amino acid sequence of SEQ ID NO: 51 as CDR2, and the amino acid sequence of SEQ ID NO: 52 as CDR3;
(15) an antibody comprising the H chain of (13) and the L chain of (14);
(16) an antibody comprising an H chain having the amino acid sequence of SEQ ID NO: 66 as CDR1, the amino acid sequence of SEQ ID NO: 67 as CDR2, and the amino acid sequence of SEQ ID NO: 68 as CDR3;
(17) an antibody comprising an L chain having the amino acid sequence of SEQ ID NO: 71 as CDR1, the amino acid sequence of SEQ ID NO: 72 as CDR2, and the amino acid sequence of SEQ ID NO: 73 as CDR3;
(18) an antibody comprising the H chain of (16) and the L chain of (17);
(19) an antibody having one or more amino acid substitutions, deletions, additions, and/or insertions in the antibody of any of (1) to (18), which has equivalent activity as the antibody of any of (1) to (18);
(20) an antibody that binds to the same epitope as the GPR49 protein epitope bound by the antibody of any of (1) to (18).

In the present invention, "have equivalent activity to an antibody" of the present invention means having equivalent binding activity to GPR49 and/or having equivalent cytotoxic activity to GPR49-expressing cells.

Methods for preparing polypeptides functionally equivalent to a certain polypeptide are well known to those skilled in the art, and include methods of introducing mutations into polypeptides. For example, those skilled in the art can prepare an antibody functionally equivalent to the antibodies of the present invention by introducing appropriate mutations into the antibody using site-directed mutagenesis (Hashimoto-Gotoh, T. et al., Gene (1995) 152: 271-275; Zoller, M J, and Smith, M. Methods Enzymol. (1983) 100: 468-500; Kramer, W. et al., Nucleic Acids Res. (1984) 12: 9441-9456; Kramer, W. and Fritz H J, Methods Enzymol. (1987) 154: 350-367; Kunkel, T A, Proc. Natl. Acad. Sci. USA. (1985) 82: 488-492; Kunkel, Methods Enzymol. (1988) 85: 2763-2766), or such. Amino acid mutations may occur naturally. Thus, the present invention also comprises antibodies functionally equivalent to the antibodies of the present invention and comprising the amino acid sequences of these antibodies, in which one or more amino acids is mutated.

Generally, the number of amino acids that are mutated in such a mutant is 50 amino acids or less, preferably 30 or less, more preferably 10 or less (for example, five amino acids or less).

Amino acid residues having similar side chain properties are preferably mutated. For example, the following classification is established based on amino acid side chain properties:
hydrophobic amino acids (A, I, L, M, F, P, W, Y, and V);
hydrophilic amino acids (R, D, N, C, E, Q, G, H, K, S, and T);
amino acids comprising the following side chains: aliphatic side chains (G, A, L, I, and P);
hydroxyl-containing side chains (S, T, and Y);
sulfur-containing side chains (C and M);
carboxylic acid- and amide-containing side chains (D, N, E, and Q);
basic side chains (R, K, and H);
aromatic ring-containing side chains (H, F, Y, and W)
(amino acids are represented by one-letter codes in parentheses).

A polypeptide comprising a modified amino acid sequence, in which one or more amino acid residues is deleted, added, and/or replaced with other amino acids, is known to retain its original biological activity (Mark, D. F. et al., Proc. Natl. Acad. Sci. USA 81, 5662-5666 (1984); Zoller, M. J. & Smith, M., Nucleic Acids Research 10, 6487-6500 (1982); Wang, A. et al., Science 224, 1431-1433; Dalbadie-McFarland, G. et al., Proc. Natl. Acad. Sci. USA 79, 6409-6413 (1982)). That is, generally in an amino acid sequence constituting a certain polypeptide, the activity of the polypeptide is highly likely to be maintained when amino acids classified into the same group are mutually substituted. In the present invention, the above-mentioned substitution between amino acids within the same amino acid group is referred to as conservative substitution.

The present invention also provides antibodies that bind to the same epitope as the anti-GPR49 antibodies disclosed in the present invention bind. More specifically, the present invention relates to antibodies that recognize the same epitope recognized by 2J18, 2L13, 2L36, 2U1E, and 2U2E, and uses of those antibodies. Such antibodies can be obtained, for example, by the following method.

Whether a test antibody shares an epitope of a certain antibody can be confirmed by checking whether the two antibodies compete for the same epitope. Competition between antibodies can be detected by a cross-blocking assay and such. For example, competitive ELISA is a preferred cross-blocking assay.

Specifically, in a cross-blocking assay, the microtiter plate wells coated with the GPR49 protein are pre-incubated with or without a candidate competitive antibody, and an anti-GPR49 antibody of the present invention is then added. The amount of the anti-GPR49 antibody of the present invention bound to the GPR49 protein in the wells indirectly correlates with the binding ability of the candidate competitive antibody (test antibody) that competes for the same epitope binding. More specifically, the greater the affinity the test antibody has for the same epitope, the lower the amount of the anti-GPR49 antibody of the present invention binding to the GPR49 protein-coated wells, and at the same time, the higher the amount of the test antibody binding to the GPR49 protein-coated wells.

The amount of antibody that binds to the wells can be measured easily by labeling the antibody in advance. For example, a biotin-labeled antibody can be measured using an avidin-peroxidase conjugate and suitable substrate. Cross-blocking assays using enzyme labels such as peroxidase are called competitive ELISA assay, in particular. The antibody can be labeled with other detectable or measurable labeling substances. More specifically, radiolabels or fluorescent labels are known.

Furthermore, when the test antibody comprises a constant region derived from a species different from that of the anti-GPR49 antibody of the present invention, either one of antibodies bound to the wells can be measured using a labeled antibody that recognizes any one of the constant regions. Alternatively, if the antibodies are derived from the same species but belong to different classes, the antibodies bound to the wells can be measured using antibodies that distinguish individual classes.

If a candidate competitive antibody can block binding of the anti-GPR49 antibody by at least 20%, preferably by at least 30%, and more preferably by at least 50%, as compared to the binding activity obtained in a control experiment performed in the absence of the candidate competitive antibody, the candidate competitive antibody is either an antibody that binds substantially to the same epitope or one that competes for binding to the same epitope as an anti-GPR49 antibody of the present invention.

An example of an epitope recognized by the antibody of any of the above-mentioned (4) to (6) includes the region from amino acid position 517 to amino acid position 537 in the human GPR49 protein (SEQ ID NO: 1). On the other hand, an example of an epitope recognized by the antibody of any of the above-mentioned (16) to (18) includes the region from amino acid position 510 to amino acid position 529 in the human GPR49 protein (SEQ ID NO: 1).

Pharmaceutical Compositions

In another aspect, the present invention provides pharmaceutical compositions comprising an antibody that binds to a GPR49 protein as an active ingredient. In addition, the present invention relates to a cell-growth inhibitor, in particular an anticancer agent, comprising an antibody that binds to a GPR49 protein as an active ingredient. Cell-growth inhibitors and anticancer agents of the present invention are preferably administered to a subject affected by cancer, or to a subject who is likely to be affected by cancer. Since GPR49 expression level is very low in normal cells other than brain, but at the same time upregulated in cancer cells, it is considered that administration of an anti-GPR49 antibody can yield cancer cell-specific cytotoxic activity.

The anti-GPR49 antibodies used in the pharmaceutical composition of the present invention (for example, anticancer agent) are not particularly limited and may be any anti-GPR49 antibodies, and examples include the above-described anti-GPR49 antibodies.

GPR49 protein has been found to be cleaved and divided into 60-kDa and 40-kDa fragments, and the N-terminal side 60-kDa fragment has been found to be secreted to the outside of the cells after cleavage. Therefore, the anti-GPR49 antibodies used in the pharmaceutical composition of the present invention are not particularly limited, but preferably recognize the C-terminal side 40-kDa fragment. Examples of the C-terminal side 40-kDa fragment include fragments comprising the amino acid sequence from amino acid position 510 to 907 in SEQ ID NO: 1, and such.

Within the amino acid sequence from amino acid position 510 to 907 in SEQ ID NO: 1, the extracellular regions are the region from amino acid position 510 to 556, the region from amino acid position 615 to 637, the region from amino acid position 704 to 722, and the region from amino acid position 792 to 800. Therefore, without particular limitation, antibodies recognizing these regions are particularly useful as pharmaceutical compositions.

In the present invention, the phrase "comprising an antibody that binds to GPR49 as an active ingredient" means comprising an anti-GPR49 antibody as the main active ingredient, and does not limit the anti-GPR49 antibody content rate.

When cancer is a target disease of the pharmaceutical composition of the present invention, the target cancer is not particularly limited, but is preferably gastric cancer, colon cancer, hepatocellular carcinoma, lung cancer, prostate cancer, ovarian cancer, Ewing's sarcoma, and glioma (for example glioblastoma), and is particularly preferably gastric cancer. The cancers may be primary lesion or metastatic foci.

The pharmaceutical compositions of the present invention can be administered orally or parenterally to a patient. Preferably, the administration is parenteral administration. Specifically, the administration method is, for example, administration by injection, transnasal administration, transpulmonary administration, or transdermal administration. Examples of administration by injection include systemic and local administrations of a pharmaceutical composition of the present invention by intravenous injection, intramuscular injection, intraperitoneal injection, subcutaneous injection, or such. A suitable administration method may be selected according to the age of the patient and symptoms. The dosage may be selected, for example, within the range of 0.0001 mg to 1,000 mg per kg body weight in each administration. Alternatively, for example, the dosage for each patient may be selected within the range of 0.001 to 100,000 mg/body. However, the pharmaceutical composition of the present invention is not limited to these doses.

The pharmaceutical compositions of the present invention can be formulated according to conventional methods (for example, Remington's Pharmaceutical Science, latest edition, Mark Publishing Company, Easton, U.S.A.), and may also contain pharmaceutically acceptable carriers and additives. Examples include, but are not limited to, surfactants, excipients, coloring agents, flavoring agents, preservatives, stabilizers, buffers, suspension agents, isotonic agents, binders, disintegrants, lubricants, fluidity promoting agents, and corrigents, and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such.

The present invention also provides methods for inducing damages in GPR49-expressing cells and methods for suppressing cell proliferation by contacting GPR49-expressing cells with antibodies that bind to the GPR49 protein.

Antibodies used in the methods of the present invention are not particularly limited, but for example, the antibodies described above may be used. Cells that are bound by the anti-GPR49 antibodies are not particularly limited as long as the cells are expressing GPR49. Preferred GPR49-expressing cells of the present invention are cancer cells. More preferably, the cells are gastric cancer cells, colon cancer cells, liver cancer cells, lung cancer cells, prostate cancer cells, or ovarian cancer cells, Ewing's sarcoma, or glioma cells (for example, glioblastoma cells). Methods of the present invention can be applied to both primary lesion and metastatic foci of these cancers. More preferred cancer cells are primary gastric cancer and metastatic gastric cancer.

In the present invention "contacting" is accomplished, for example, by adding antibodies to a culture solution of GPR49-expressing cells cultured in vitro. Furthermore, "contacting" in the present invention is also carried out by administering to a non-human animal to which a GPR49-expressing cell has been transplanted into the body, or to an animal carrying cancer cells which endogenously express GPR49.

The following method is preferably used as a method for evaluating or measuring cell damage induced on GPR49-expressing cells by contacting the cells with an anti-GPR49 antibody. A method for evaluating or measuring the cytotoxic activity in vitro include methods for measuring the abovementioned antibody-dependent cell-mediated cytotoxicity (ADCC) activity, complement-dependent cytotoxicity (CDC) activity, and such. Whether or not an anti-GPR49 antibody has ADCC activity or CDC activity can be measured by known methods (for example, Current protocols in Immunology, Chapter 7. Immunologic studies in humans, Editor, John E. Coligan et al., John Wiley & Sons, Inc., (1993) and the like). For activity measurements, a binding antibody having the same isotype as anti-GPR49 antibody but not having the cytotoxic activities can be used as a control antibody in the same manner as the anti-GPR49 antibody, and activity can be confirmed when the anti-GPR49 antibody shows a stronger cytotoxic activity than the control antibody.

An antibody isotype is defined by the amino acid sequence of H chain constant region in the antibody. The isotype of an antibody is ultimately determined in vivo by class switching that arises from genetic recombinations in chromosomes which occur during maturation of antibody-producing B-cells. Difference in isotype is reflected in the difference of physiological and pathological functions of antibodies. Specifically, for example, the intensity of cytotoxic activity is known to be influenced by antibody isotype as well as the expression level of the antigen. Therefore, when measuring the above-described cytotoxic activity, an antibody of the same isotype as the test antibody is preferably used as the control.

Furthermore, to evaluate or measure cytotoxic activity in vivo, for example, GPR49-expressing cancer cells are intradermally or subcutaneously transplanted to a non-human animal subject, and then a test antibody is intravenously or intraperitoneally administered daily or at intervals of few days, starting from the day of transplantation or the following day. Cytotoxic activity can be determined by daily measurement of tumor size. In a manner similar to the evaluation in vitro, cytotoxic activity can be determined by administering a control antibody having the same isotype, and observing that the tumor size in the anti-GPR49 antibody-administered group is significantly smaller than that of control antibody-administered group. When mouse is used as the non-human animal subject, it is preferable to use a nude (nu/nu) mouse whose thymus has been made genetically defective so that its T lymphocyte function is lost. The use of such a mouse can eliminate the involvement of T lymphocytes in the test animals when evaluating or measuring the cytotoxic activity of the administered antibody.

Furthermore, the present invention provides methods for diagnosing cancer comprising detecting a GPR49 protein or a gene encoding a GPR49 protein. Upregulation of GPR49 expression was confirmed significantly in various cancer tissues or cancer cell lines, whereas GPR49 expression in normal cells is very low in organs other than the brain. Therefore, GPR49 is useful as a specific marker for detecting cancer.

In an embodiment of the methods of the present invention, cancer is diagnosed by detecting a GPR49 protein in a sample. Preferably, an extracellular region of a GPR49 protein is detected. Detection of a GPR49 protein is preferably carried out using an antibody that recognizes a GPR49 protein.

A specific example of the methods of diagnosis of the present invention is a method of cancer diagnosis comprising the steps of:
(a) providing a sample collected from a subject; and
(b) detecting a GPR49 protein contained in the collected sample using an antibody that binds to the GPR49 protein.

In the present invention, detection includes quantitative and qualitative detection. Examples of the qualitative detection include the following:
simple detection of the presence or absence of the GPR49 protein;
determination of whether or not the GPR49 protein is present above a certain amount; and comparison of the amount of the GPR49 protein with that of other samples (for example, a control sample).

On the other hand, examples of quantitative detection include measurement of the GPR49 protein concentration and measurement of the amount of the GPR49 protein.

Test samples of the present invention are not particularly limited as long as they are samples that may contain a GPR49 protein. Specifically, samples collected from the body of an organism such as mammal are preferred. Samples collected from humans are more preferred. Specific examples of the test samples include blood, interstitial fluid, plasma, extravascular fluid, cerebrospinal fluid, synovial fluid, pleural fluid, serum, lymphatic fluid, saliva, urine, tissue, ascites, and intraperitoneal lavage. Preferred samples are those obtained from test samples such as immobilized specimens of tissue or cells collected from the body of an organism, or cell culture solution.

GPR49 protein is cleaved and divided into an N-terminal peptide of approximately 60 kDa and a C-terminal peptide of approximately 40 kDa, and the N-terminal peptide is secreted into blood. Therefore, in the diagnostic method of the present invention, the cleaved N-terminal peptide or the C-terminal peptide may be detected. For example, the secreted N-terminal peptide included in a sample such as blood or serum may be detected.

The cancers that are diagnosed by the present invention are not particularly limited and may be any cancer. Specific examples include hepatocellular carcinoma, lung cancer, prostate cancer, ovarian cancer, Ewing's sarcoma, and glioma cells (for example, glioblastoma). In the present invention, both primary lesions and metastatic foci of these cancers can be diagnosed. Primary gastric cancer and metastatic gastric cancer are particularly preferable in the present invention.

In the present invention, when the protein is detected in a test sample, subject is diagnosed as having cancer using the protein level as an indicator. More specifically, if the amount of the GPR49 protein detected in a test sample is higher than that in a negative control or a healthy subject, it is determined that the subject has cancer or is likely to get cancer in the future. That is, the present invention relates to methods for diagnosing cancer which comprise the steps of:
(1) detecting a GPR49 expression level in a biological sample collected from a subject; and
(2) indicating that the subject has cancer if the GPR49 expression level detected in step (1) is higher than that of a control.

In the present invention, "control" refers to samples serving as a standard for comparison, and include negative controls and biological samples from healthy subjects. Negative control can be obtained by collecting biological samples from healthy subjects and mixing them as necessary. The GPR49 expression level in a control can be detected in parallel with the GPR49 expression level in the biological sample of a subject. Alternatively, by detecting the GPR49 expression level in biological samples of many healthy subjects in advance, a standard expression level in healthy subjects can be determined statistically. Specifically, for example, the mean value±2× standard deviation (S. D.), or mean value±3× standard deviation (S. D.) may be used as the standard value. Statistically, 80% of the healthy subjects are within ±2× standard deviation (S. D.) from the mean value, and 90% of the healthy subjects are within ±3× standard deviation (S. D.) from the mean value.

Alternatively, the GPR49 expression level in control can be determined using a receiver operating characteristic (ROC) curve. An ROC curve is a graph showing detection sensitivity on the vertical axis, and false positive rate (i.e., "1-specificity") on the horizontal axis. In the present invention, an ROC curve can be obtained by plotting the changes of sensitivity to false positive rate by continuously varying the standard values for determining the GPR49 expression level in a biological sample.

The "standard value" for obtaining an ROC curve is a numerical value temporarily used for statistical analysis. In general, "standard values" for obtaining an ROC curve are continuously varied within a range that covers all selectable standard values. For example, the standard values can be varied between the minimum and maximum values of GPR49 measured in the population analyzed.

Based on the ROC curve obtained, standard values that are expected to yield a desired detection sensitivity and accuracy can be selected. Standard values that are statistically determined by an ROC curve or such are also called "cut-off values". In methods for detecting cancer based on cut-off values, the GPR49 expression level detected in step (1) is compared to the cut-off value in step (2) described above. Then, cancer is detected in a subject if the GPR49 expression level in step (1) is higher than the cut-off value.

In the present invention, the GPR49 expression level can be determined by any method. More specifically, the GPR49 expression level can be determined by evaluating the amount of GPR49 mRNA, the amount of GPR49 protein, and the biological activity of GPR49 protein. The amount of GPR49 mRNA and GPR49 protein can be determined by the methods described herein.

Subjects in the present invention may be any animal species that express a GPR49 protein. For example, many non-human mammals such as chimpanzees (*Pan troglodytes*) (ENSPTRG00000005223 (XR_021586.1)), rhesus monkeys (*Macaca mulatta*) (ENSMMUG00000020942), mice (*Mus musculus*) (ENSMUSG00000020140), rats (*Rattus norvegicus*) (ENSRNOG00000004221 (LOC687868)), guinea pigs (*Cavia porcellus*) (ENSCPOG00000009492), dogs (*Canis familiaris*) (ENSCAFG00000000451), cats (*Felis catus*) (ENSFCAG00000008064), and chickens (*Gallus gallus*) (ENSGALG00000010163) are known to express the GPR49 protein. Therefore, these animals are included in the subjects of the present invention. Particularly preferred subjects are humans. As a matter of course, it goes without saying that when a non-human animal is used as a subject, the GPR49 protein for the animal species is detected.

Methods for detecting the GPR49 protein contained in a test sample are not particularly limited. An immunological method using an anti-GPR49 antibody for detection such as the following is preferred:
radioimmunoassay (RIA);
enzyme immunoassay (EIA);
fluorescence immunoassay (FIA);
luminescence immunoassay (LIA);
immunoprecipitation (IP);
turbidimetric immunoassay (TIA);
Western blotting (WB);
immunohistochemical (IHC) method; and
single radial immunodiffusion (SRID).

Of the above techniques, immunohistochemical (IHC) method is a preferred immunological assay for methods for diagnosing cancer that comprise the step of detecting a GPR49 protein on a section of immobilized tissue or cells obtained from a patient affected with cancer. The above-mentioned immunological methods such as immunohistochemical (IBC) method are methods known to those skilled in the art.

That is, GPR49 is a membrane protein whose expression is specifically elevated in cancer cells. Therefore, cancer cells or cancer tissues can be detected by anti-GPR49 antibodies. Cancer cells contained in cells or tissues collected from a living body are detected by the above-mentioned immunohistochemical analysis.

In another preferred embodiment, cancer tissues in a living body can be detected with anti-GPR49 antibodies. More specifically, the present invention relates to methods for detecting cancer which comprise the steps of: (1) administering to a subject a GPR49 protein-binding antibody labeled with a labeling substance such as radioisotopes; and (2) detecting accumulation of the labeling substance. In order to trace the antibody administered into a living body, the antibody may be labeled to enable detection. For example, the behavior of antibodies labeled with a fluorescent substance, luminescent substance, or radioisotope can be traced in vivo. Antibodies labeled with a fluorescent substance or a luminescent substance can be observed using an endoscope or a laparoscope. When using a radioisotope, the localization of an antibody can be imaged by tracing the radioactivity of the radioisotope. In the present invention, the localization of anti-GPR49 antibodies in vivo demonstrates the presence of cancer cells.

A positron-emitting radionuclide can be used as a radioisotope for antibody labeling for detecting cancer in vivo. For example, antibodies can be labeled with positron-emitting radionuclides such as $^{18}F$, $^{55}Co$, $^{64}Cu$, $^{66}Ga$, $^{68}Ga$, $^{76}Br$, $^{89}Zr$, and $^{124}I$. Anti-GPR49 antibodies can be labeled with these positron-emitting radionuclides by using known methods (Acta Oncol. 32, 825-830, 1993).

After administering anti-GPR49 antibodies labeled with a positron-emitting radionuclide to humans or animals, radiation emitted by the radionuclides is measured from outside the body using positron emission tomography scanner (PET), and then converted into an image by computed tomography methods. PET is an instrument for non-invasively obtaining data relating in vivo behavior of drugs and such. Radiation intensity can be quantitatively converted into an image as signal intensity using PET. By using PET as described above, antigenic molecules that are highly expressed in a particular cancer can be detected without collecting samples from patients. In addition to the above-mentioned nuclides, anti-GPR49 antibodies can be radiolabeled with short-lived nuclides using positron-emitting radionuclides such as $^{11}$C, $^{13}$N, $^{15}$O, $^{18}$F, and $^{45}$Ti.

Production of short-lived nuclides with the above-mentioned nuclides using medical cyclotron, techniques for producing short-lived radiolabeled compounds, and such, are currently under research and development. Anti-GPR49 antibodies can be labeled with various radioisotopes using such techniques. Anti-GPR49 antibodies administered to patients accumulate at primary lesions and metastatic foci according to the specificity of the anti-GPR49 antibodies at each site of the pathological tissue. If the anti-GPR49 antibodies are labeled with positron-emitting radionuclides, the presence of primary lesions and metastatic foci can be detected from the localization of their radioactivity by detecting the radioactivity. For use in such diagnostic purpose, emission activity values of 25 to 4,000 keV gamma particles or positrons can be suitably used. Furthermore, therapeutic effects can be expected by selecting a suitable nuclide and giving in high dose. To obtain anticancer effect by radiation, nuclides that provide emission values of 70 to 700 keV gamma particles or positrons can be used.

In another embodiment of the methods of the present invention, the expression of GPR49 gene is detected. The gene detected in the present invention is not particularly limited, but mRNA is preferred. In the present invention, detection includes quantitative and qualitative detection. Examples of qualitative detection include the following operations:
simple detection of the presence or absence of GPR49 mRNA;
determination of whether or not the GPR49 mRNA is present above a certain amount; and
comparison of the amount of GPR49 mRNA to that of other samples (for example, a control sample).

On the other hand, quantitative detection includes, for example, measurement of the GPR49 mRNA concentration, and measurement of the amount of GPR49 mRNAs.

Any sample that may contain GPR49 mRNAs may be used as a test sample of the present invention. Samples collected from the body of an organism such as mammals are preferred, and samples collected from humans are more preferred. Specific examples of the test samples include blood, interstitial fluid, plasma, extravascular fluid, cerebrospinal fluid, synovial fluid, pleural fluid, serum, lymphatic fluid, saliva, urine, tissue, ascites, and intraperitoneal lavage. Preferred samples are those obtained from test samples such as immobilized specimens of tissue or cells collected from the body of an organism and cell culture solution, and they are included in the test samples of the present invention.

When samples are obtained from test samples such as cell culture solutions or specimens of immobilized tissues or cells collected from the body of all organism, in situ hybridization method is preferably used. In situ hybridization method has been developed as a method for examining the presence/absence and distribution of a specific DNA or RNA in cells or tissues and the intensity of their expression. The principle behind this method is that the method utilizes the nature of a nucleic acid probe having a nucleotide sequence complementary to a specific nucleotide sequence in cells to specifically form a complex. When such probes are labeled with radioisotopes (RIs), antigenic substances (haptens), or such in advance, hybridization spot becomes discriminable through detection of these labels; therefore, in situ hybridization method is used for detection and such of DNA, RNA, or the like in cells. RIs have been favorably used for labeling probes. More favorable examples include use of fluorescent labeling utilizing non-radioactive substances, for example, haptens such as biotin or digoxigenin. Particularly favorable examples include use of detection methods utilizing fluorescence in situ hybridization called FISH.

The cancer to be diagnosed is not particularly limited. Specific examples include gastric cancer, colon cancer, hepatocellular carcinoma, lung cancer, prostate cancer, ovarian cancer, and glioma (for example glioblastoma). In the present invention, both primary lesions and metastatic foci of these cancers can be diagnosed.

Subjects in the present invention may be any animal species that expresses the GPR49 protein. For example, many non-human mammals such as mice, rats, rhesus monkeys, and chimpanzees are known to express GPR49. Particularly suitable subjects are humans. When a non-human animal species is used as a subject, the GPR49 mRNA of the animal species is detected.

Specific embodiments of the detection method are described below. First, a sample is prepared from a subject. Next, GPR49 mRNAs included in the sample are detected. In the present invention, cDNAs synthesized from mRNAs can also be detected. In the present invention, when GPR49 mRNAs or cDNAs encoding GPR49 is detected in a test sample, it is determined that the subjects are likely to have cancer. For example, if a higher amount of GPR49 mRNAs or cDNAs encoding GPR49 is detected in the test sample than in a negative control or healthy subjects, it is determined that the subject has cancer or is likely to become affected by cancer in the future.

Methods for detecting mRNA are known. Specifically, for example, Northern blotting method, RT-PCR method, DNA array method, and such may be used in the present invention.

The detection methods of the present invention described above can be automated using various automatic testing devices. Through automation, large quantities of samples can be examined in a short period of time.

The present invention also provides diagnostic agents or kits for diagnosing cancer which comprise reagents for detecting the GPR49 protein in a test sample. The diagnostic agents of the present invention comprise at least an anti-GPR49 antibody.

Kits for diagnosing cancer can be produced by combining the agents for diagnosing cancer of the present invention with another element used for detecting GPR49. More specifically, the present invention relates to kits for diagnosing cancer which comprise an antibody that binds to GPR49 and a reagent for detecting binding between the antibody and GPR49, and further may comprise a control sample comprising a biological sample containing GPR49. In addition, instructions that describe the measurement operation can be attached to the kits of the present invention.

All prior art references cited herein are incorporated by reference into this description.

EXAMPLES

Herein below, the present invention will be specifically described with reference to the Examples, but it is not to be construed as being limited thereto.

Example 1

Analysis of the Human GPR49 mRNA Expression Using Human Exon 1.0 ST Array

To elucidate the expression distribution of human GPR49 mRNA in clinical cancer, cancer cell lines, and various normal organs, expression analysis was carried out using Human Exon 1.0 ST Array (Affymetrix) which was originally developed for analyzing splice variants. The advantage of performing expression analysis using Human Exon 1.0 ST Array is that in contrast to the former expression array of Affymetrix which basically only had one probe set on the 3' side for each gene, Human Exon 1.0 ST Array has at least one probe set installed for every gene exon, and therefore, when a gene-by-gene expression analysis is performed using this array, expression data of multiple probe sets can be obtained for each gene, and the reliability of the expression data for every gene will increase.

In this expression analysis, the total RNAs used were derived from the tumor sites of 22 isolated lung adenocarcinoma tissues, 13 isolated gastric cancer tissues, five Ewing's sarcoma tissues, and 20 isolated ovarian cancer tissues, 19 types of lung adenocarcinoma cell lines, four types of small cell lung cancer cell lines, 16 types of gastric cancer cell lines, 20 types of ovarian cancer cell lines, and 71 types of normal tissues (purchased from Clontech, Ambion, STRATAGENE, Cell APPLICATIONS, Panomics, CHEMICON, and BioChain Institute).

Total RNA was extracted using Trizol (Invitrogen) according to the manufacturer's protocol on tumor sites and normal sites of all isolated clinical cancer tissues (with prior informed consent), and cancer cell lines (purchased from ATCC, JCRB, and RIKEN BIOSOURCE CENTER CELL BANK).

Gene expression analysis experiments were performed following the GeneChip Whole Transcript (WT) Sense Target Labeling Assay Manual (Affymetrix) using 1 m of above-mentioned total RNAs, and the Human Exon 1.0 ST Array Data was digitized using the ExACT (Exon Array Computational Tool) software provided by Affymetrix.

There were 21 Core Probe Sets for the human GPR49 in Human Exon 1.0 ST Array, and those probe set IDs are: 3422146, 3422162, 3422166, 3422167, 3422175, 3422177, 3422179, 3422180, 3422181, 3422182, 3422189, 3422191, 3422194, 3422195, 3422197, 3422198, 3422199, 3422200, and 3422201.

Figure 2:
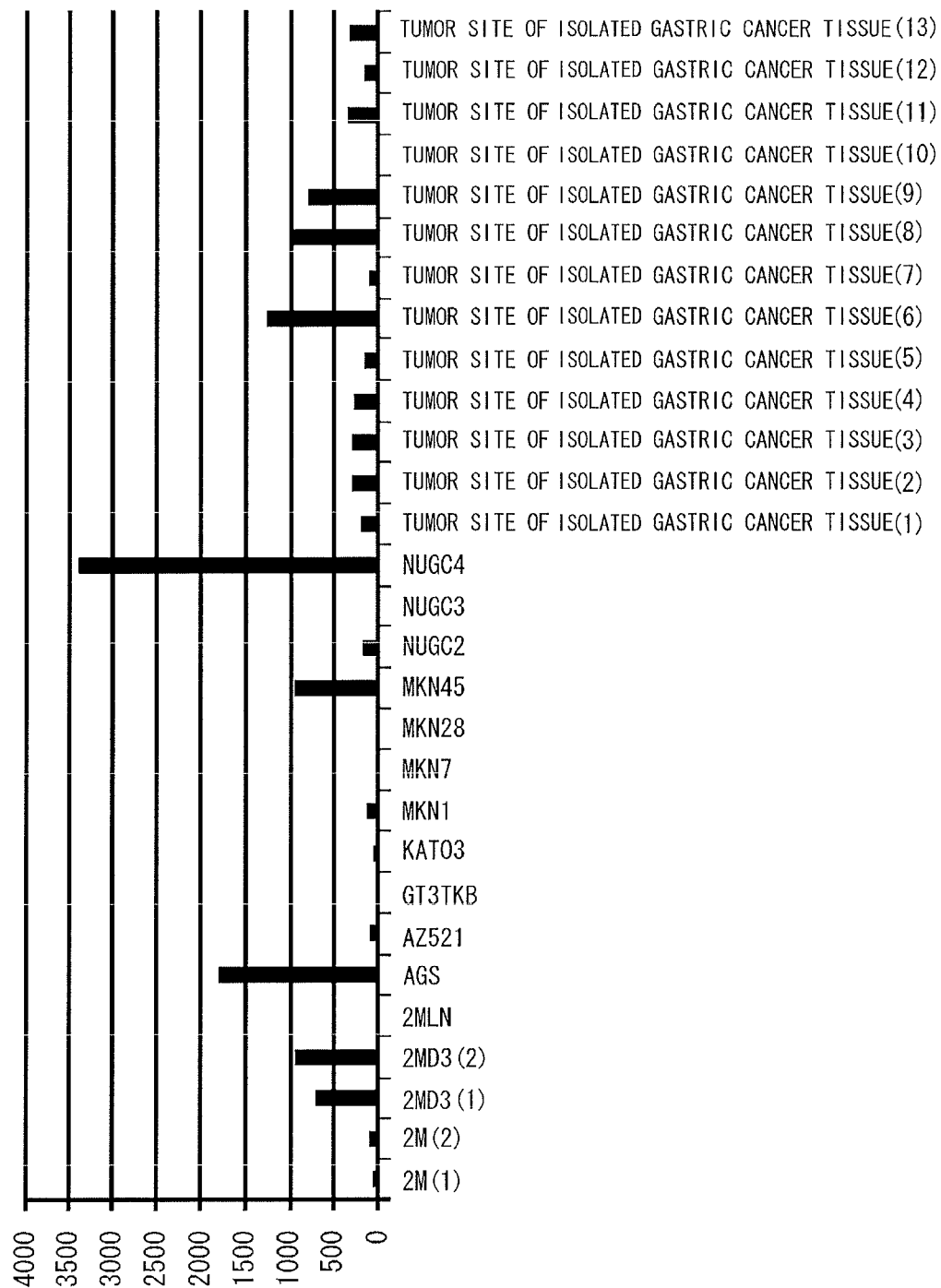
FIG. 2 shows the expression profile of human GPR49 in gastric cancer cell lines and in tumor sites of removed gastric cancer tissues. The values were obtained from Exon Array analysis, and higher the value, higher the mRNA expression level.
Figure 3:
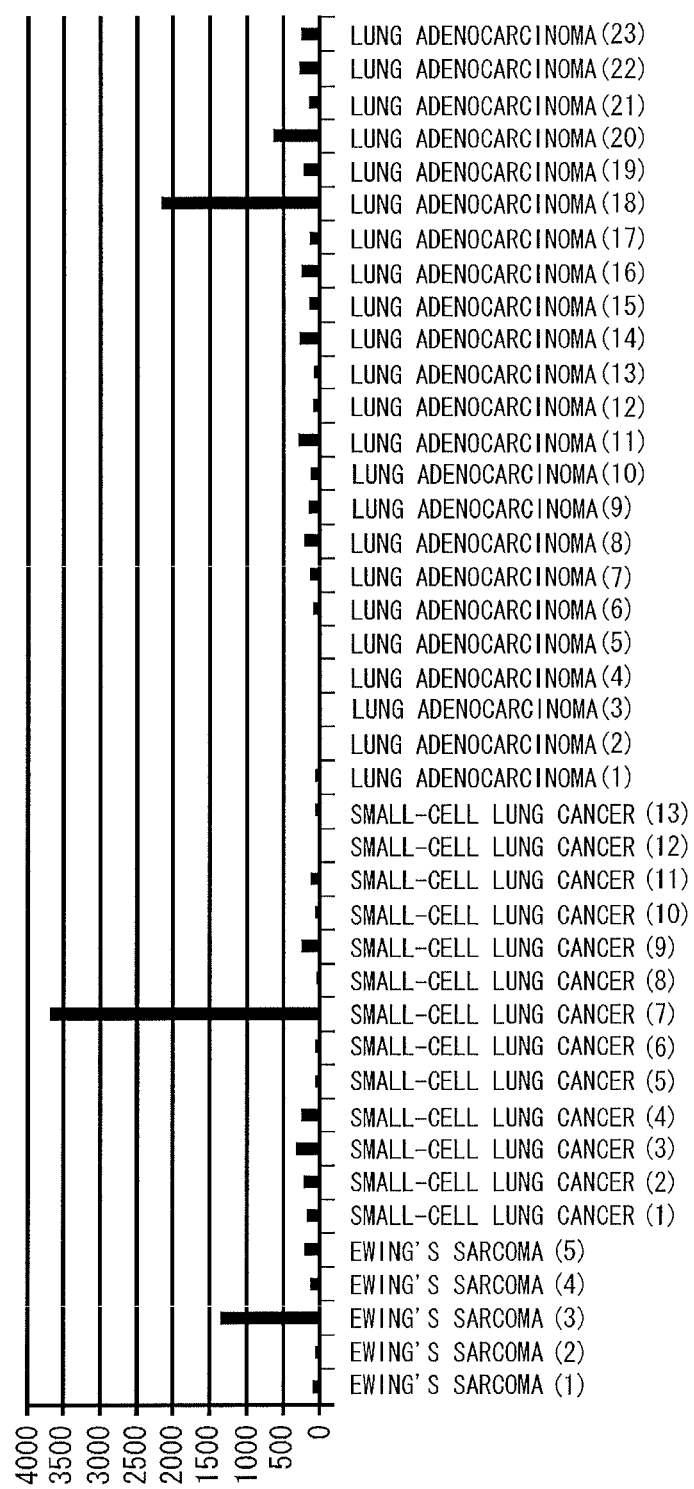
FIG. 3 shows the expression profile of human GPR49 in tumor sites of removed Ewing's sarcoma, small cell lung cancer, and lung adenocarcinoma tissues. The values were obtained from Exon Array analysis, and higher the value, higher the mRNA expression level.
Figure 4:
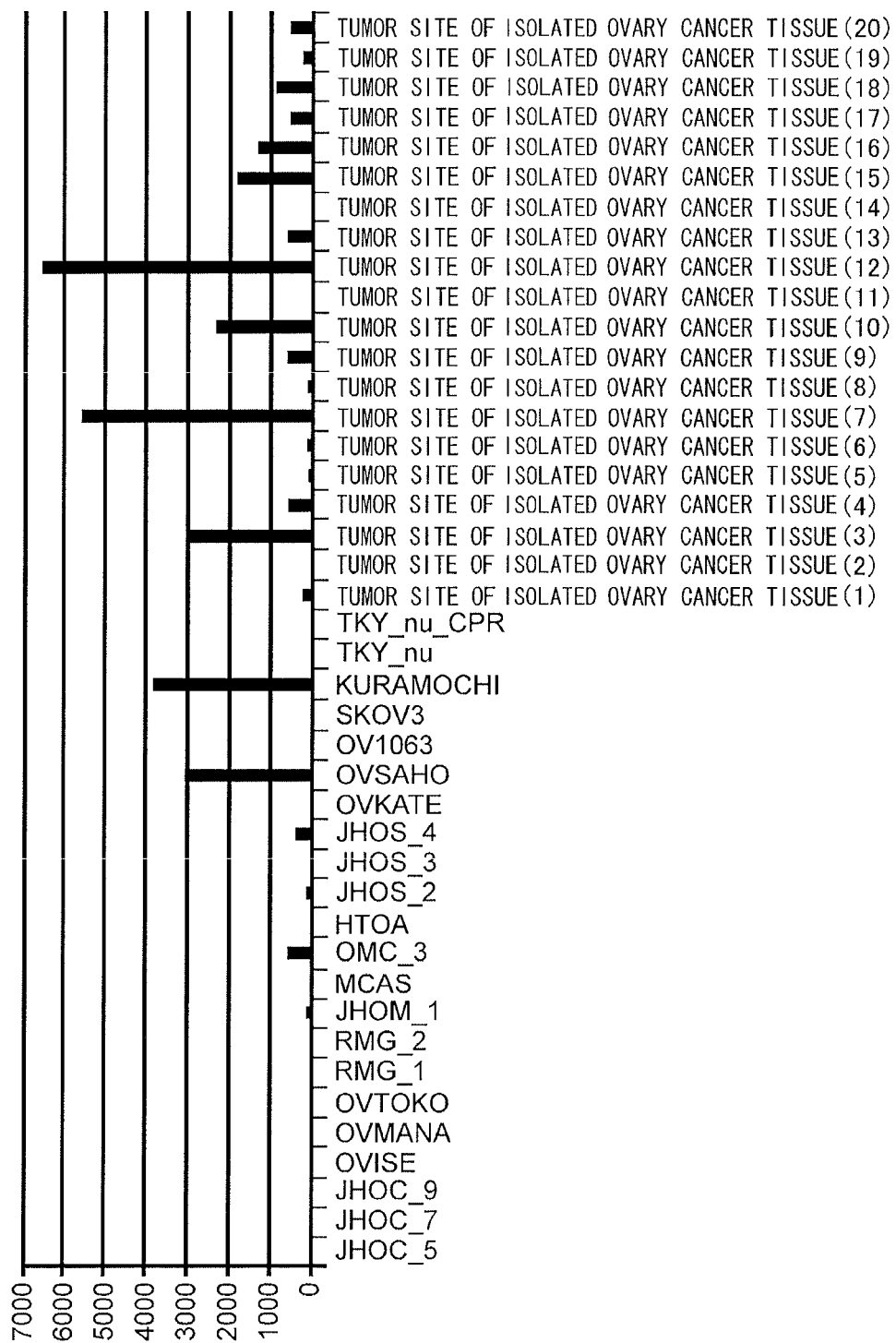
FIG. 4 shows the expression profile of human GPR49 in ovarian cancer cell lines and in tumor sites of removed ovarian cancer tissues. The values were obtained from Exon Array analysis, and higher the value, higher the mRNA expression level.

Expression data for probe set ID 3422201 for normal tissues; gastric cancer cell line and tumor sites of isolated gastric cancer tissues; tumor sites of tissues isolated from Ewing's sarcoma, small cell lung cancer, and lung adenocarcinoma; and ovarian cancer cell lines and tumor sites of isolated ovarian cancer tissues are shown in FIG. 1; FIG. 2; FIG. 3; and FIG. 4, respectively.

As will be noted from FIGS. 1 to 4, expression of the human GPR49 transcript in normal tissues is limited to the diencephalon, medulla oblongata, peripheral nerve, skeletal muscle, uterus, placenta, fetal colon, and such. On the other hand, the expression is low in the lung, kidney, liver, bone marrow, and peripheral blood which are organs in which drug toxicity is of concern, and therefore it is expected that side effects may be kept low. Among cancer tissues, high expression levels were observed in gastric cancer, Ewing's sarcoma, small cell lung cancer, lung adenocarcinoma, and ovarian cancer, and anti-tumor agents targeting human GPR49 are expected to be effective against these types of cancer.

Example 2

Establishment of Cells Expressing the Full-Length Human GPR49

The full-length human GPR49 cDNA was isolated by the PCR method based on NCBI Accession Nos. NP_003658.1 (SEQ ID NO: 1 (amino acid sequence)) and NM_003667.2 (SEQ ID NO: 2 (nucleotide sequence)) respectively, and then cloned into a mammalian cell expression vector (pcDNA5/FRT/TO) (Invitrogen). pcDNA5/FRT/TO enables inducible expression of a inserted gene under the control of a hybrid human CMV/TetO$_2$ promoter, and is a vector into which a neomycin resistance gene has been inserted as a drug resistance marker. Additionally, using the FlpIn expression system (Invitrogen) which enables inducible expression only in the presence of tetracycline or doxycycline, the full-length human GPR49 cDNA was transfected into 293FlpIn T-Rex cells. Fugene6 (Roche) was used for transfecting the expression vector into the 293FlpIn T-Rex cells cultured in DMEM (high glucose)/10% FBS/100 µg/mL Zeocin™ (Invitrogen)/15 µg/mL blasticidin (Invitrogen). pcDNA5/FRT/GPR49 vector together with the pOG44 vector that expresses Flp recombinase were transfected following the instruction manual, and full-length human GPR49-transfected cell lines B2 and B4 with inducible expression of human GPR49 were established by 50 µg/mL hygromycin B (Invitrogen) selection. For an HA-tag was inserted at the N-terminus of the GPR49 gene inserted into the expression vector, selected cells were detected by an anti-HA antibody (Sigma).

The vector was transfected into DG44 cell line, which is derived from Chinese hamster ovary, using a BioRad Gene Pulser to obtain HA-GPR49-expressing cell line 2B10.

Furthermore, a vector introduced with the GPR49 gene was constructed for DNA immunization. The expression vector pMCN enables induction and expression of a transferred gene under the control of a mouse CMV promoter (ACCESSION No. U68299), and is a vector into which a neomycin resistance gene has been incorporated as a drug resistance marker. A GPR49 expression vector pMCN-GPR49 was prepared by cloning the GPR49 gene into pMCN using a conventional method.

Example 3

Production of Anti-GPR49 Monoclonal Antibodies by DNA Immunization

DNA immunization by gene transfer to mice was carried out by the GeneGun Particle method. The procedure was performed according to the BioRad manual. The bullets for DNA immunization were prepared by mixing 1 mm Gold particles (BioRad) and pMCN-GPR49 DNA, and coating the interior of a tube with them. Gene was transferred by shooting the bullets coated with pMCN-GPR49 DNA into the abdominal skin of a 6-week-old female MRL/lpr mouse using a Helios Gene Gun (BioRad) at a pressure of 200 to 300 psi. The gene transferred to the keratinocytes, Langerhans cells, and dermal dendritic cells in the skin is thought to evoke immunity because these cells become antigen-presenting cells (APC) by expressing the GPR49 protein (Methods 31, 232-242 (2003); Immunization with DNA through the skin). DNA immunization was carried out six times at one week intervals. As the final immunization, 1,000,000 GPR49-expressing DG44 cell lines 2B10 were diluted with PBS and administered into the tail vein. Measurement of the antibody titer was performed by FACS analysis using 2B10 cells. A comparison was made of the reactivity of sera from the immunized mice to GPR49 protein expressed on surface membranes of 2B10 cells. Mouse showing the highest response was subjected to final immunization and then cell fusion. The spleen cells were resected three days after the final immunization and mixed with P3-X63Ag8U1 mouse myeloma cells (P3U1, purchased from ATCC) at a 2:1 ratio. Cell fusion was carried out by gradually adding PEG1500 (Roche Diagnostics), and hybridomas were prepared. After the PEG1500 concentration was diluted by carefully adding RPMI 1640 medium (Gibco BRL), the PEG1500 was removed by a centrifugation procedure. Then, the hybridomas were suspended in RPMI 1640 medium containing 10% FBS, 1×HAT media supplement (SIGMA), and 0.5×BM-Condimed H1 Hybridoma cloning supplement (Roche Diagnostics) (hereinafter, HAT medium), and seeded into a 96-well culture plate to a total volume of 200 μL/well. The cell density at the time of seeding was diluted depending on the number of P3U1 cells used, and the hybridomas were cultured for about one week in HAT medium in the 96-well culture plate at 37° C. and 5% $CO_2$. Screening for hybridomas that secreted antibodies into the culture supernatant was performed by flow cytometry.

Example 4

Preparation of sGPR49Fc

The fragment comprising the amino acids of positions 1-555 in the GPR49 protein was amplified by PCR, and a vector was constructed such that it will be expressed as a fusion protein with Fc protein of mouse IgG2a. The vector was transfected into DG44 cells, and a cell that can express the sGPR49Fc fusion protein was selected as the neomycin-resistant cell line. The obtained cell line, 2D3, was mass cultured, the culture supernatant was collected, and the sGPR49Fc protein was purified. The sGPR49Fc protein affinity-purified as an Fc fusion protein using a Protein A column served as an antigen for protein immunization or an antigen for screening hybridomas.

Example 5

Preparation of Anti-GPR49 Antibody by sGPR49Fc Protein Immunization

50 μg of the affinity-purified sGPR49Fc protein was mixed with Freund's complete adjuvant for immunization, and 50 μg of the affinity-purified sGPR49Fc protein mixed with Freund's incomplete adjuvant was used for subcutaneous immunization of mice twice to induce antibodies. To the mouse showing the highest reactivity to the GPR49 protein, 25 μg of the sGPR49Fc protein was injected into the tail vein, cell fusion was conducted three days later, and then hybridomas were prepared as described above.

Example 6

Evaluation of Binding Activity by Flow Cytometry (FACS)

The binding to the human GPR49/DG44 cells (2B10) was evaluated by flow cytometry using the obtained hybridomas. The cell lines expressing human GPR49 suspended in FACS buffer (2% FBS/PBS/0.05% $NaN_3$) were diluted to $1×10^6$ cells/mL with FACS buffer, and then aliquoted at 50 μL/well into a Falcon 353910 round-bottom 96-well plate. Hybridoma culture supernatant diluted to a suitable concentration was added to the wells containing the cells and reacted for 60 minutes on ice. Then, the cells were washed once with FACS buffer. Goat F(ab')$_2$ fragment anti-mouse IgG(H+L)-FITC (Beckman Coulter) was added to the wells containing the cells as a secondary antibody, and reacted for 30 minutes on ice. After reaction, the supernatant was removed by centrifugation, and then the cells suspended in 100 μL of FACS buffer were subjected to flow cytometry. A FACS Calibur (Becton Dickinson) was used for flow cytometry. The viable cell population was gated with a forward scatter-side scatter dot blot, an FL1 histogram was made of the cells contained in the population, and binding activity thereof was evaluated.

When the hybridoma supernatants were reacted with 2B10 in which GPR49 is induced and expressed in DG44 cells and with the parental cell line DG44 respectively, hybridomas that specifically reacted with GPR49-expressing cells were obtained. The hybridomas from these wells were made into single clones by the limiting dilution method. The isotype of each antibody was analyzed using an IsoStrip™ mouse monoclonal antibody isotyping kit (Roche Diagnostics). As a result, 2J18-1N and 2J18-3 were IgM, and 2L7-8, 2L9-3, 2L10-19, 2L13-3, 2L15-12, 2L16-15, 2L18-15, 2L33-6, 2L34-5, 2L36-12, 2T4E-6, 2T9E1#14, 2T15E-2, 2T42E-4, 2T54-2, 2T65-3, 2T37-16, 2U1E-1, 2U2E-2, and 2U4E-11 were IgG1. Culturing of the hybridomas made into single clones was scaled up, and then the antibodies were purified from the culture supernatant using a protein G column in accordance with the manual. The IgM antibodies were purified using a protein L column in accordance with the manual. The purified antibodies were quantified by DC Protein Assay or such.

Example 7

Cloning of Antigen Genes

The antibody variable region gene sequences of the six hybridomas, 2J18-1N, 2U1E-1, 2U2E-2, 2L13-3, 2L36-12, and 2T15E-2 that showed ADCC activity and CDC activity were determined. The antibody genes were amplified by RT-PCR method using total RNAs extracted from the respective hybridomas producing the anti-GPR49 antibodies, 2J18-1N, 2U1E-1, 2U2E-2, 2L13-3, 2L36-12, and 2T15E-2. Hereinafter, the gene names for the respective antibodies, 2J18-1N, 2U1E-1, 2U2E-2, 2L13-3, 2L36-12, and 2T15E-2, will be abbreviated as 2J18, 2U1E, 2U2E, 2L13, 2L36, and 2T15E genes. The total RNA was extracted from $1×10^7$ hybridomas using RNeasy Plant Mini Kits (QIAGEN). A RACE library was constructed from 1 μg of total RNA using a SMART RACE cDNA Amplification Kit (CLONTECH). 5' end gene fragments of the gene encoding the antibody produced in the hybridoma were amplified using a synthetic oligonucleotide MHC-IgM (SEQ ID NO: 61; CCACCAGATTCTTATCA-GACAGG) which is complementary to the murine IgM constant region sequence for IgM antibody 2J18-1N, using the synthetic oligonucleotide MHC-IgG1 (SEQ ID NO: 62; GGGCCAGTGGATAGACAGATG) which is complementary to the murine IgG1 constant region sequence for other antibody genes, or using the synthetic oligonucleotide kappa (SEQ ID NO: 63; GCTCACTGGATGGTGGGAAGATG) which is complementary to the murine K-chain constant region nucleotide sequence. Reverse transcription reaction was carried out at 42° C. for 1.5 hours. 50 μL of a PCR solution contained 5 μL of 10× Advantage 2 PCR Buffer, 5 μL of 10× Universal Primer A Mix, 0.2 mM dNTPs (dATP, dGTP, dCTP, dTTP), 1 µL of Advantage 2 Polymerase Mix (all manufactured by CLONTECH), 2.5 µL of reverse transcription reaction product, and 10 pmol of the synthetic oligonucleotide MHC-IgM, MHC-IgG1, or kappa. The PCR reaction was carried out as follows: reaction at initial temperature of 94° C. for 30 seconds, 5 cycles with 5 seconds at 94° C., and 3 minutes at 72° C.; next 5 cycles with 5 seconds at 94° C., 10 seconds at 70° C., and 3 minutes at 72° C.; and then 25 cycles with 5 seconds at 94° C., 10 seconds at 68° C., and 3 minutes at 72° C. Finally, the reaction product was heated for 7 minutes at 72° C. Each PCR product was purified from agarose gel using a QIAquick Gel Extraction Kit (QIAGEN). Then the PCR product was cloned into a pGEM-T Easy vector (manufactured by Promega) and the nucleotide sequence was determined.

For 2J18, SEQ ID NO: 3 shows the nucleotide sequence and SEQ ID NO: 4 shows the amino acid sequence of the H chain variable region; and SEQ ID NO: 8 shows the nucleotide sequence and SEQ ID NO: 9 shows the amino acid sequence of the L chain variable region. In addition, for 2J18, SEQ ID NO: 5 shows the amino acid sequence of heavy chain CDR1, SEQ ID NO: 6 shows the amino acid sequence of heavy chain CDR2, SEQ ID NO: 7 shows the amino acid sequence of heavy chain CDR3, SEQ ID NO: 10 shows the amino acid sequence of light chain CDR1, SEQ ID NO: 11 shows the amino acid sequence of light chain CDR2, and SEQ ID NO: 12 shows the amino acid sequence of light chain CDR3.

For 2U1E, SEQ ID NO: 13 shows the nucleotide sequence and SEQ ID NO: 14 shows the amino acid sequence of the H chain variable region; and SEQ ID NO: 18 shows the nucleotide sequence and SEQ ID NO: 19 shows the amino acid sequence of the L chain variable region. In addition, for 2U1E, SEQ ID NO: 15 shows the amino acid sequence of heavy chain CDR1, SEQ ID NO: 16 shows the amino acid sequence of heavy chain CDR2, SEQ ID NO: 17 shows the amino acid sequence of heavy chain CDR3, SEQ ID NO: 20 shows the amino acid sequence of light chain CDR1, SEQ ID NO: 21 shows the amino acid sequence of light chain CDR2, and SEQ ID NO: 22 shows the amino acid sequence of light chain CDR3.

For 2U2E, SEQ ID NO: 23 shows the nucleotide sequence and SEQ ID NO: 24 shows the amino acid sequence of the H chain variable region; and SEQ ID NO: 28 shows the nucleotide sequence and SEQ ID NO: 29 shows the amino acid sequence of the L chain variable region. In addition, for 2U2E, SEQ ID NO: 25 shows the amino acid sequence of heavy chain CDR1, SEQ ID NO: 26 shows the amino acid sequence of heavy chain CDR2, SEQ ID NO: 27 shows the amino acid sequence of heavy chain CDR3, SEQ ID NO: 30 shows the amino acid sequence of light chain CDR1, SEQ ID NO: 31 shows the amino acid sequence of light chain CDR2, and SEQ ID NO: 32 shows the amino acid sequence of light chain CDR3.

For 2L13, SEQ ID NO: 33 shows the nucleotide sequence and SEQ ID NO: 34 shows the amino acid sequence of the H chain variable region; and SEQ ID NO: 38 shows the nucleotide sequence and SEQ ID NO: 39 shows the amino acid sequence of the L chain variable region. In addition, for 2L13, SEQ ID NO: 35 shows the amino acid sequence of heavy chain CDR1, SEQ ID NO: 36 shows the amino acid sequence of heavy chain CDR2, SEQ ID NO: 37 shows the amino acid sequence of heavy chain CDR3, SEQ ID NO: 40 shows the amino acid sequence of light chain CDR1, SEQ ID NO: 41 shows the amino acid sequence of light chain CDR2, and SEQ ID NO: 42 shows the amino acid sequence of light chain CDR3.

For 2L36, SEQ ID NO: 43 shows the nucleotide sequence and SEQ ID NO: 44 shows the amino acid sequence of the H chain variable region; and SEQ ID NO: 48 shows the nucleotide sequence and SEQ ID NO: 49 shows the amino acid sequence of the L chain variable region. In addition, for 2L36, SEQ ID NO: 45 shows the amino acid sequence of heavy chain CDR1, SEQ ID NO: 46 shows the amino acid sequence of heavy chain CDR2, SEQ ID NO: 47 shows the amino acid sequence of heavy chain CDR3, SEQ ID NO: 50 shows the amino acid sequence of light chain CDR1, SEQ ID NO: 51 shows the amino acid sequence of light chain CDR2, and SEQ ID NO: 52 shows the amino acid sequence of light chain CDR3.

For 2T15E, SEQ ID NO: 64 shows the nucleotide sequence and SEQ ID NO: 65 shows the amino acid sequence of the H chain variable region; and SEQ ID NO: 69 shows the nucleotide sequence and SEQ ID NO: 70 shows the amino acid sequence of the L chain variable region. In addition, for 2T15E, SEQ ID NO: 66 shows the amino acid sequence of heavy chain CDR1, SEQ ID NO: 67 shows the amino acid sequence of heavy chain CDR2, SEQ ID NO: 68 shows the amino acid sequence of heavy chain CDR3, SEQ ID NO: 71 shows the amino acid sequence of light chain CDR1, SEQ ID NO: 72 shows the amino acid sequence of light chain CDR2, and SEQ ID NO: 73 shows the amino acid sequence of light chain CDR3.

Example 8

Western Blotting Using the Cell Lysates from Cell Line with Forced Expression

Figure 5:
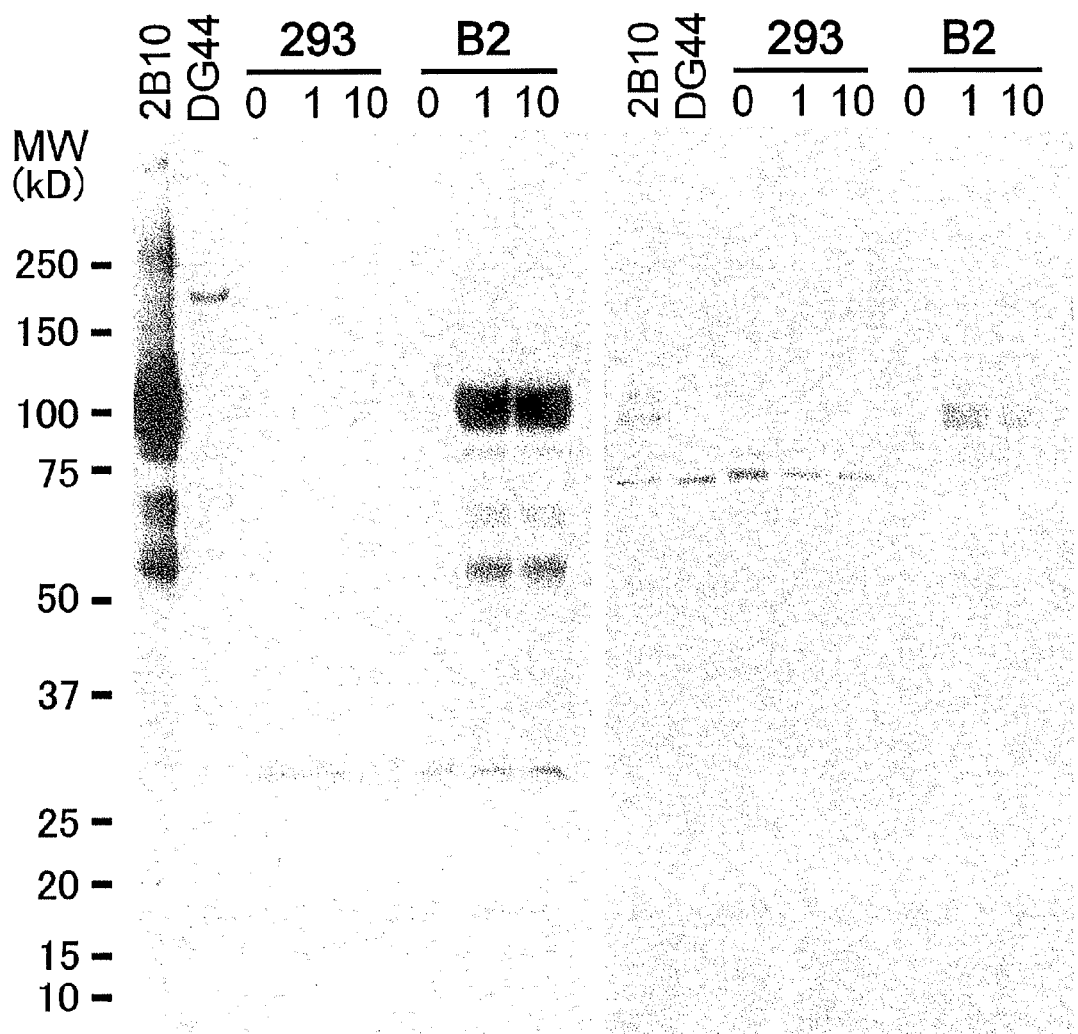
FIG. 5 shows a series of photographs depicting the detection of induced expression of GPR49 by monoclonal antibody 2U2E-2. They show that the antibodies specifically recognize GPR49 induced by adding 1 μL and 10 μL of doxycycline (Dox), and that the antibodies recognize the same bands as those obtained when the HA-tag attached to the N-terminus is detected using anti-HA-tag antibodies.

Antibodies that can be used for Western blotting were screened using the cell lysate of 2B10 expressing HA-GPR49 in DG 44 cell line, 2U1E-1, 2U2E-2, 2U4E-11, 2T15E-2, 2T65-3, and such were able to detect a band of 100-kDa molecular weight predicted as the GPR49 protein by Western blotting. To confirm that the detected 100-kDa band is derived from human GPR49, the reactivities with the cell lysates obtained from non-induced and induced HA-GPR49-expressing 293 cells B2, in which HA-GPR49 expression can be induced with doxocycline, were analyzed by Western blotting. The results are shown in FIG. 5. In 293 and B2, 0 refers to cell lysates without induction, and 1 and 10 refer to cell lysates with induction. Using monoclonal antibody 2U2E-2, 100-kDa bands were confirmed to be detectable specific to the inducibly expressed lanes. Since the size of this band was the same as the 100-kDa band for the HA-GPR49 band detected by the HA-tag, it was concluded that monoclonal antibody 2U2E-2 is an antibody that recognizes GPR49.

Example 9

Confirmation of Antibody-Recognized Antigen Using siRNA

To further confirm that the 100-kDa band is a GPR49-derived band, GPR49 expression was knocked down by transfecting siRNAs, and disappearance of a band recognized by the antibody was confirmed. siRNAs against GPR49 (Cat. No. 1299003) LGR5-HSS112507, LGR5-HSS112508, LGR5-HSS112509 (hereinafter abbreviated as siRNA 507, 508, and 509) purchased from Invitrogen were transfected into the 2B10 cell line or colon cancer cell line LoVo cells which highly express GPR49 according to the manual, and their cell lysates were analyzed by Western blotting. As a result, as shown in FIG. 6, a band corresponding to a 100-kDa protein having the molecular weight predicted for GPR49 was markedly eliminated for siRNAs 508 and 509 among the three siRNAs 507, 508, and 509 used, the 100-kDa band was considered to indicate recognition of GPR49.

Figure 6:
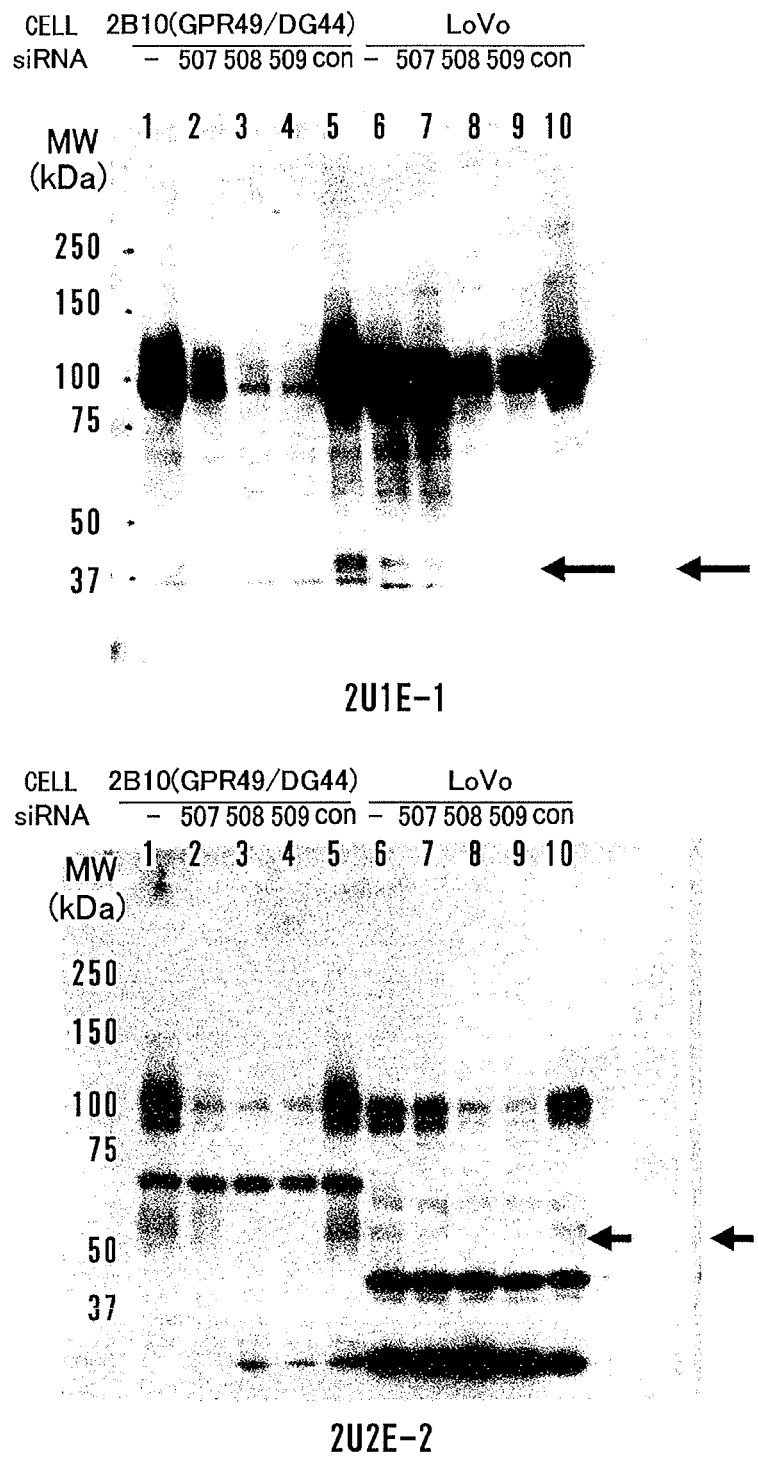
FIG. 6 depicts a series of photographs showing the detection of GPR49 protein in the cell lysate from DG44 cells forcedly expressing GPR49 and colon cancer cell line LoVo transfected with GPR49 siRNA, using monoclonal antibodies 2U1E-1 and 2U2E-2. In cells transfected with siRNA 507, 508, and 509, the expression of GPR49 was suppressed. (−) indicates cells not transfected with siRNA, and "con" indicates cells transfected with control siRNA. In addition to the 100-kDa band, the 40-kDa band indicated by an arrow disappeared with 2U1E-1 and the 60-kDa band indicated by an arrow disappeared with 2U2E-2; therefore, these bands are GPR49-derived bands.

Furthermore, as shown in FIG. 6, as a result of Western blotting using 2U1E-1 and 202E-2, a new band that is eliminated along with the 100-kDa protein band eliminated as a result of siRNA introduction was identified. In the detection using the 2U1E-1 antibody, an approximately 40-kDa protein band was eliminated in addition to the 100-kDa protein band due to siRNA. In the detection using the 2U2E-2 antibody, an approximately 60-kDa protein band was found to be eliminated in addition to the 100-kDa protein band due to siRNA. Since the total size of these two bands exactly yields 100 kDa corresponding to the full length, GPR49 protein may be cleaved somewhere to yield 60-kDa and 40-kDa proteins. The 60-kDa and 40-kDa bands were also detected in colon cancer cell line LoVo cells.

Example 10

Detection of the Cleaved Fragments by Immunoprecipitation

Figure 7:
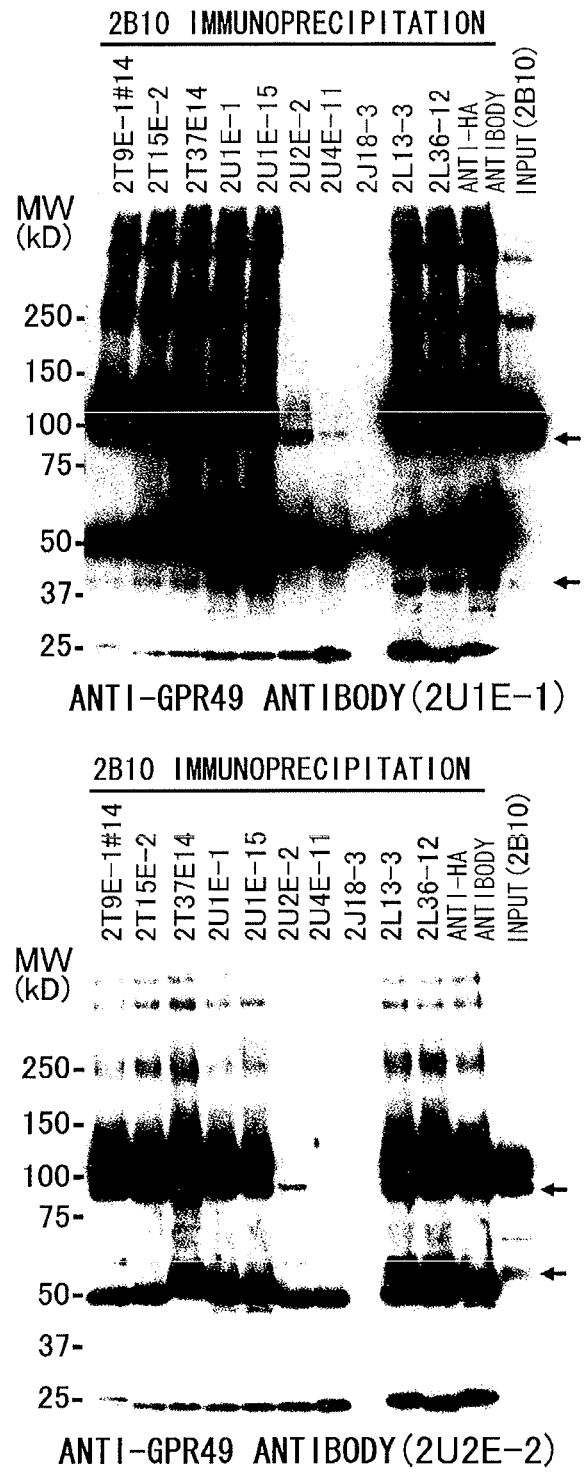
FIG. 7 shows a series of photographs depicting the detection of GPR49 by monoclonal antibodies through immunoprecipitation of the cell lysate of HA-GPR49-expressing DG44 cell line 2B10. 100-kDa and 40-kDa bands were detected with 2U1E-1 and 100-kDa and 60-kDa GPR49 bands were detected with 2U2E-2. HRP-labeled anti-mouse IgG(H+L) antibody (manufactured by Jackson ImmunoResearch Laboratories) was used as a secondary antibody.
Figure 8:
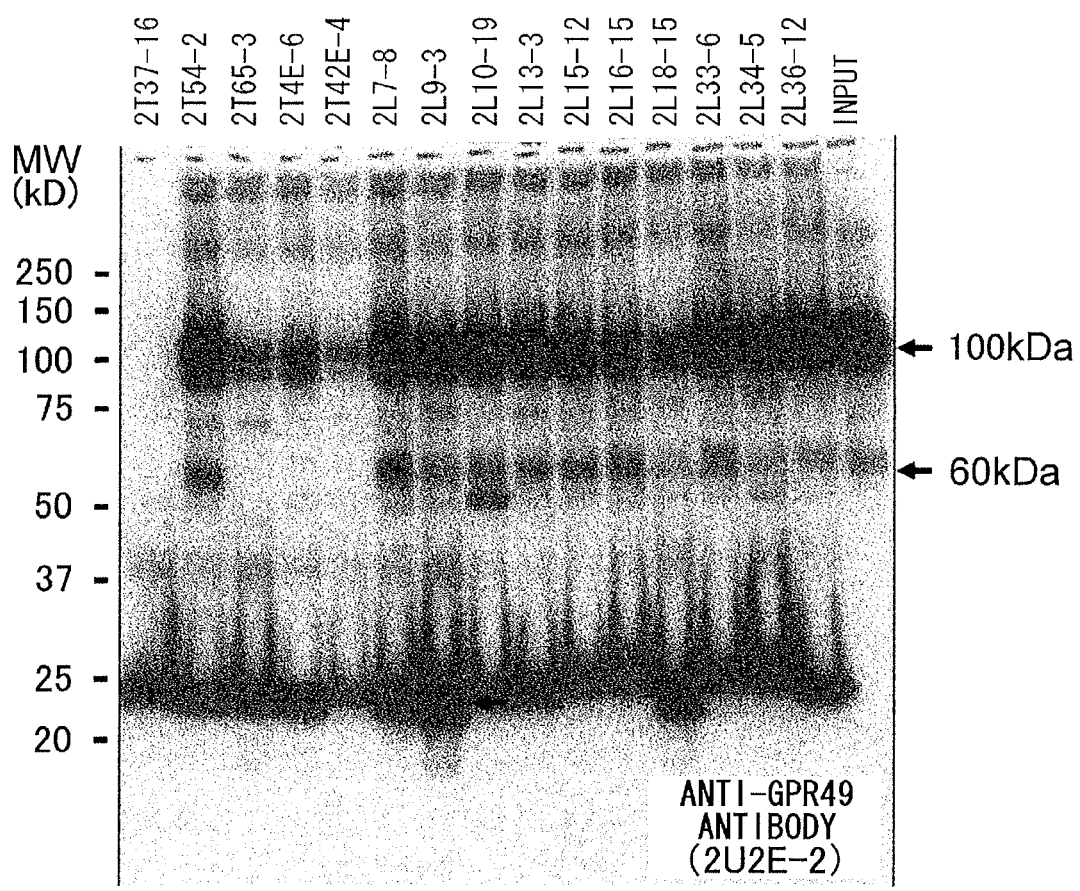
FIG. 8 is a photograph showing the detection of GPR49 by monoclonal antibodies through immunoprecipitation of the cell lysate of 2B10 (DG44 cell expressing HA-GPR49). The 60-kDa GPR49 band was detected by all antibodies of the 2L series. To distinguish the band derived from the H chain of the antibodies used for immunoprecipitation and the 60-kDa GPR49 band, HRP-labeled anti-mouse kappa antibody (manufactured by Southern Biotech) was used as a secondary antibody.

To confirm the presence of the 40-kDa and 60-kDa protein bands detected in Western blotting, immunoprecipitation experiments were carried out using GPR49 monoclonal antibodies. Cell lysate prepared by solubilizing HA-GPR49-expressing DG44 cell line 2B10 in NP40 lysis buffer (0.5% NP40, 50 mM Tris-HCl (pH7.5), 150 mM NaCl, protease inhibitor complete mini (Roche)) was used as the sample for immunoprecipitation. The amount of protein included in the cell lysate was quantified by DC Protein Assay using BSA as a standard. A solution containing 2 µg of antibody was added to 500 µL of cell lysate containing 100 µg of protein, and this was reacted at 4° C. for one hour. Additionally, 20 µL of Protein A/G Plus agarose (Santa Cruz) was added and this was reacted overnight. Agarose beads were centrifuged at 1,000×g for one minute, washed twice with 1 mL of PBS, and then antigens bound to the antibodies were eluted by adding 50 µL of 2×SDS-sample buffer and warming at 60° C. for 30 minutes. After centrifuging at 1,000×g for one minutes, 15 µL, of the supernatant obtained was subjected to SDS-PAGE. Samples were transferred to Immobilon-P (Millipore) by a submarine method, monoclonal antibodies 2U1E-1 and 2U2E-2 were used for detection. These results are shown in FIGS. 7 and 8. As is seen in the lanes for the samples immunoprecipitated using 2L13-3 and 2L36-12, a 40-kDa band and a 60-kDa band in addition to the 100-kDa band could surely be detected using 2U1E-1 and 2U2E-2, respectively. This showed that GPR49 exists as molecules having molecular weights indicated by sizes of approximately 60 kDa and 40 kDa in addition to 100 kDa. HRP-labeled anti-mouse IgG(H+L) antibody (manufactured by Jackson ImmunoResearch Laboratories) was used as the secondary antibody in FIG. 7, and HRP-labeled anti-mouse kappa antibody (manufactured by Southern Biotech) was used as the secondary antibody for distinguishing the band derived from the H chain of the antibody used for immunoprecipitation from the 60-kDa GPR49 band in FIG. 8.

Example 11

Western Blotting Using the Cell Lysates of Various Cancer Cell Lines

Figure 9:
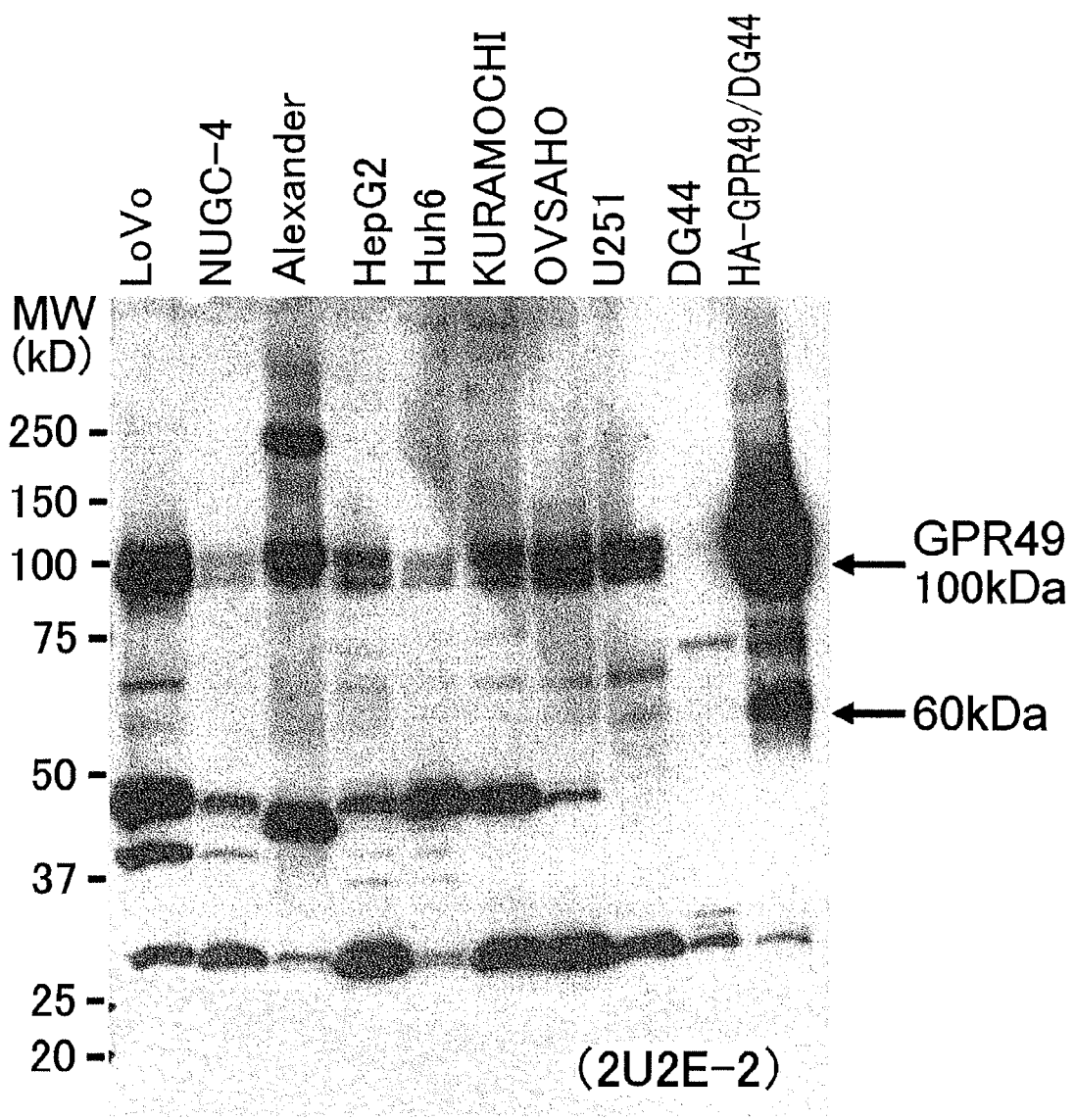
FIG. 9 is a photograph showing detection performed on cell lysates of various cancer cell lines by WB using monoclonal antibodies. The lanes in the photograph have their sample names indicated and are colon cancer cell line LoVo, gastric cancer cell line NUGC-4, hepatocellular carcinoma cell line Alexander, hepatocellular carcinoma cell line HepG2, hepatocellular carcinoma cell line Huh6, ovarian cancer cell line KURAMOCHI, ovarian cancer cell line OVSAHO, glioma U251, Chinese hamster ovary cell DG44, and HA-GPR49-expressing DG44 cell line 2B10, respectively.

Cell lysates from various cancer cell lines were subjected to detection using monoclonal antibody 2U2E-2. As shown in FIG. 9, GPR49 protein expression is remarkably upregulated particularly in colon cancer cell line LoVo, hepatocellular carcinoma cell lines Alexander and HepG2, ovarian cancer cell lines KURAMOCHI and OVSAHO, and glioma U251. The arrows indicate the 100-kDa and 60-kDa protein bands. The lanes in the photograph have their sample names indicated and are colon cancer cell line LoVo, gastric cancer cell line NUGC-4, hepatocellular carcinoma cell line Alexander, hepatocellular carcinoma cell line HepG2, hepatocellular carcinoma cell line Huh6, ovarian cancer cell line KURAMOCHI, ovarian cancer cell line OVSAHO, glioma U251, Chinese hamster ovary cell DG44, and HA-GPR49-expressing D044 cell line 2B10, respectively.

Example 12

Measurement of CDC Activity of the Anti-GPR49 Monoclonal Antibodies

CDC activity was measured using the degree of 7-AAD uptake into damaged cells as an indicator.

Figure 10:
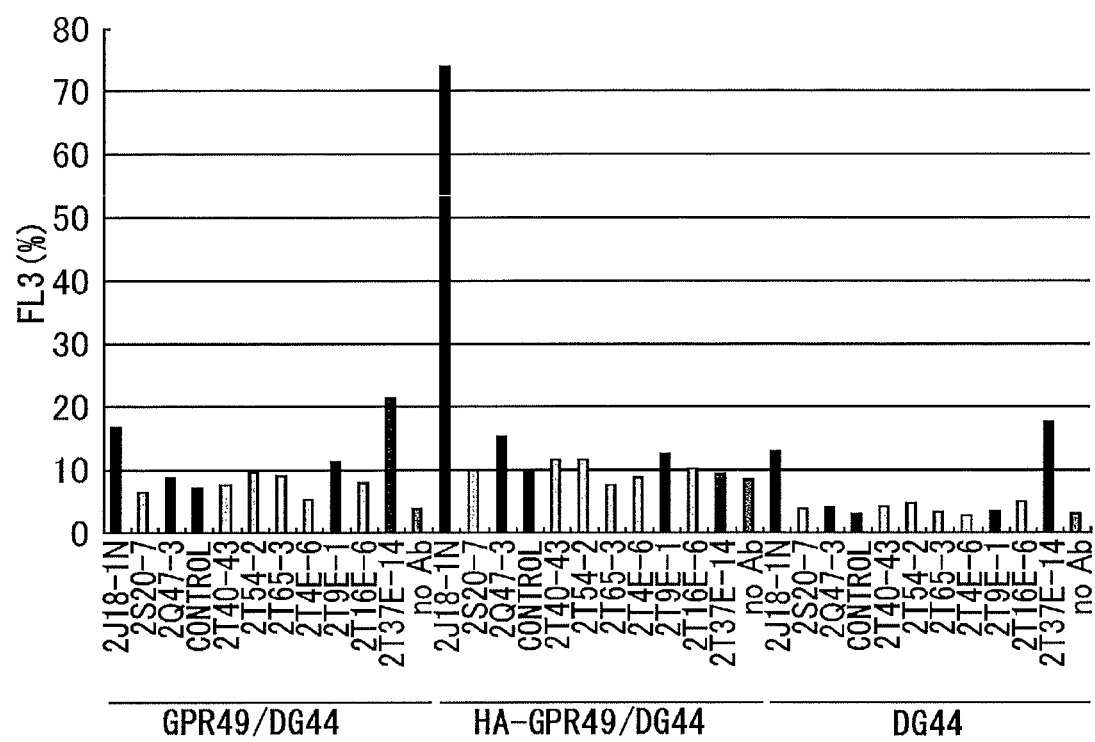
FIG. 10 is a graph showing CDC activity of GPR49 antibodies.

GPR49-expressing DG44 cells or DG44 cells were reacted at 4° C. for 30 minutes with a 10 µg/mL of monoclonal antibody. Next, Baby Rabbit Complement (CEDARLANE LABORATORIES) was added at a final concentration of 1% or 5%, and the reaction was continued at 37° C. for 90 minutes. After addition of 7-AAD (Beckman Coulter) at a final concentration of 1 µg/mL, this was left to stand at room temperature for ten minutes. Thereafter, the cells were washed with FACS buffer, and then the ratio of damaged cells was analyzed with a FACS Calibur. The value of % FL3 indicates the proportion of damaged cells stained with 7-AAD, and complement-dependent cytotoxicity (CDC) activity in HA-GPR49-expressing DG44 cells was observed specifically when using anti-GPR49 antibody 2J18-1N (FIG. 10).

Example 13

Construction of the 2J18 scFv-Fc Expression Vector

Since anti-human GPR49 monoclonal antibody 2J18 is an IgM, ADCC activity cannot be evaluated. Therefore the antibody gene was expressed as a form of scFv-Fc. As described in Example 7, H chain and L chain variable regions of the cloned 2J18 antibody gene were amplified by PCR, they were linked by a GGGGS amino acid as a linker, and then an antibody molecule expressed as the form of scFv-Fc was produced by ligating the hinge region, CH2 region, and CH3 region of the mouse IgG2a H chain. Specifically, PCR was carried out using the following primers:

```
KozakATG-2J18VH
                                        (SEQ ID NO: 74)
GCGAATTCCACCATGGGATG;

2J18VH-GS1
                                        (SEQ TD NO: 75)
TGAGCCACCGCCACCTGCAGAGACAGTGACCAGAG;

GSI-2J18VL
                                        (SEQ ID NO: 76)
GGTGGCGGTGGCTCACAGATTGTTCTCACCCAGTC;

2J18VH-GS2
                                        (SEQ ID NO: 77)
ACTCCCACCACCGCCTTTTATTTCCAATTTTGTCCCCG;
```

-continued

GS2-mIgG2a-hinge
(SEQ ID NO: 78)
GGCGGTGGTGGGAGTGAGCCCAGAGGGCCCAC;

and

NX-mG2a-3
(SEQ ID NO: 79)
CTCTAGAGCGGCCGCTTATC.

These were inserted into an expression vector to complete the 2J18scFv-Fc expression vector.

Example 14

Preparation of the 2J18 scFv-Fc Protein

The 2J18scFv-Fc expression vector was transiently expressed in 293T cells, and the protein was affinity purified from the culture supernatant using a Protein G column. 18 µg of plasmid DNA was mixed with 54 µL of Fugene HD (manufactured by Roche) in 900 µL of Opti-MEM (manufactured by Invitrogen), this was left to stand for 15 minutes, and then the mixture was poured onto 2,000,000 293T cells (purchased from ATCC) cultured in a T75 flask to transfer the gene into the cells. After culturing in a 5% $CO_2$ incubator at 37° C. for three days, the culture supernatant was collected, and 2J18scFV-Fc was purified using a Protein G column according to the manual.

Example 15

Preparation of the Human IgG1 Chimeric Antibody 2L13

The H chain and L chain variable regions of the antibody gene of anti-human GPR49 monoclonal antibody 2L13 cloned as in Example 7 were amplified by PCR, they were ligated with the H chain and L chain constant regions of human IgG1, and inserted into an expression vector so that they can be expressed as a human IgG1 chimeric molecule. The obtained vector was transfected into rat myeloma cell YB2/0 (purchased from ATCC) to establish a neomycin-resistant line. The cells were cultured in RPMI-1640/10% FBS/500 µg/mL Geneticin/penicillin-streptomycin, and human IgG1 chimeric antibody was purified from the culture supernatant using a Protein A column according to the manual. The purified antibody 2L13/YB was subjected to ADCC activity measurements.

Example 16

Measurement of ADCC Activity of the Anti-GPR49 Monoclonal Antibodies

The ADCC activity of an anti-human GPR49 monoclonal antibody against 2B10, which is a DG44 cell forcedly expressing GPR49, was investigated by the Chromium release assay. The target cell 2B10 was cultured for a few hours in Chromium-51-supplemented culture medium (CHO-S SFM H (manufactured by Invitrogen)), then the culture medium was removed, and after washing the cells with the culture medium, the cells suspended in a fresh culture medium were added to a 96-well round-bottom plate at $1\times10^4$ cells per well. Subsequently, the antibody was added to final concentrations of 1 µg/mL and 0.1 µg/mL, an effector cell (a recombinant cell (Japanese Patent Application No. 2007-20155) produced by forcedly expressing a chimeric protein comprising the extracellular regions of a mouse Fe-gamma receptor 3 (NM_010188) and the transmembrane regions and intracellular regions of a human gamma chain (NM_004106) in NK-92 (ATCC, CRL-2407)) was added to each well at approximately five-times the amount of the target cell, and the plate was left to stand in a 5% $CO_2$ incubator at 37° C. for four hours. Then, the plate was centrifuged, a fixed amount of the supernatant was collected from each well, and radioactivity was measured using a Wallac 1480 gamma counter, and the specific chromium release rate (%) was determined using the following equation:

Specific chromium release rate (%)=$(A-C)\times 100/(B-C)$

Here, A represents the radioactivity in each well, B represents the mean value of radioactivity released into the medium upon cell lysis by Nonidet P-40 at a final concentration of 1%, and C represents the mean value of radioactivity when only medium is added.

Figure 11:
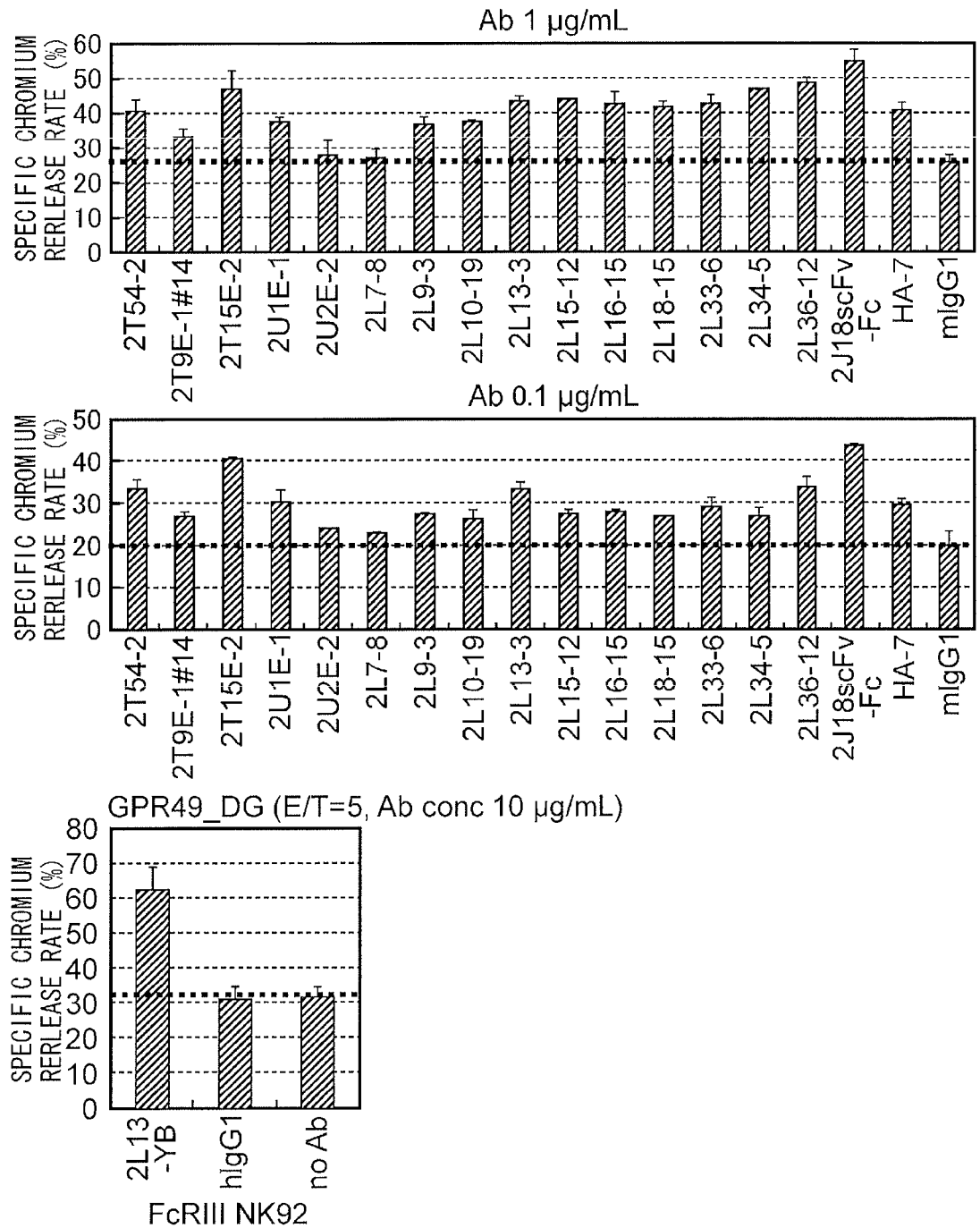
FIG. 11 depicts graphs showing ADCC activity of GPR49 antibodies against DG44 cells expressing HA-GPR49.

As a result, as shown in FIG. 11, among the anti-human GPR49 monoclonal antibodies used in the examination, 2T54-2, 2T15E-2, 2L13-3, 2L36-12, and 2J18scFv-Fc in particular showed very strong ADCC activity induction against human GPR49-expressing cell 2B10. The present result showed that antibody therapy against tumors targeting human GPR49 is very useful.

The ADCC activity of human IgG1 chimeric antibody 2L13/YB was measured by using a 2B10 cell for the target cell as described above, adding an effector cell (a recombinant cell (Japanese Patent Application No. 2007-20155) produced by forcedly expressing human Fe-gamma receptor 3 (NM_000569) in NK-92 (ATCC, CRL-2407)) at approximately five-times the amount of the target cell, and allowing the plate to stand in a 5% $CO_2$ incubator at 37° C. for four hours. Then, this plate was centrifuged, a fixed amount of the supernatant was collected from each well, radioactivity was measured with a Wallac 1480 gamma counter, and the specific chromium release rate (%) was determined using the equation. As a result, as shown in FIG. 11, very high ADCC activity was observed against human GPR49-expressing cells with 2L13/YB.

Example 17

Cytocidal (Cell-Killing) Effect by Internalization Using Mab-Zap

Figure 12:
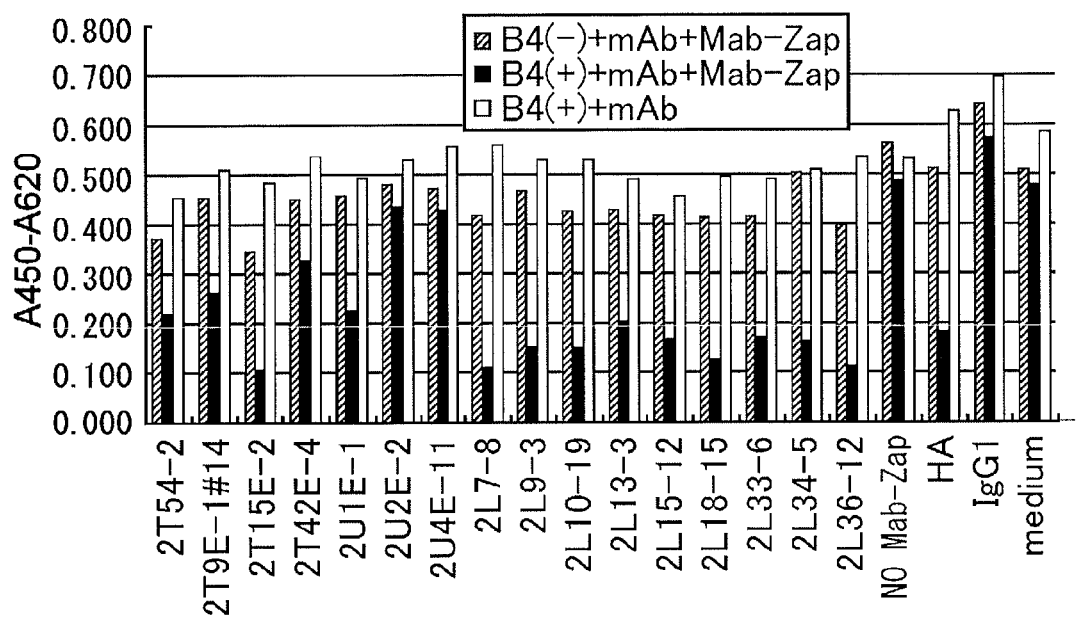
FIG. 12 is a graph showing the cytocidal (cell-killing) activity due to antibody internalization using Mab-Zap. Each of the three bar graphs shows the results of measuring by WST8 assay the proportion of viable cells in a sample prepared by adding antibodies and Mab-Zap to GPR49-inducible 293 cell line B4 without GPR49 induction (left), a sample prepared by adding antibodies and Mab-Zap to GPR49-inducible cells with GPR49 expression induction (middle), and a sample prepared by adding antibodies alone to GPR49-inducible cells with GPR49 expression induction (right).

As a model for development of an antibody pharmaceutical whose mode of action involves binding of antibody conjugated with a toxin or such to the target cell followed by internalization into the cell, and then killing the target cell by the function of the conjugated toxin, Mab-Zap (manufactured by Advanced Targeting Systems) to which a toxin called saporin is conjugated was used as a secondary antibody to evaluate the cell killing ability against GPR49-expressing cells. The antibody and Mab-Zap was added at 100 ng/well to B4 cells with induced and uninduced expression of HA-GPR49 incubated in a 5% $CO_2$ incubator at 37° C. for three days, the number of viable cells was analyzed by WST8 assay using a viable cell count reagent SF (Nacalai Tesque). The results are shown in FIG. 12. Cytotoxic activity was confirmed in all of the antibodies analyzed except for 2T42E-4, 2U2E-2, and 2U4E-11.

Example 18

Expression and Epitope Analysis of GST Fusion Protein

Figure 13:
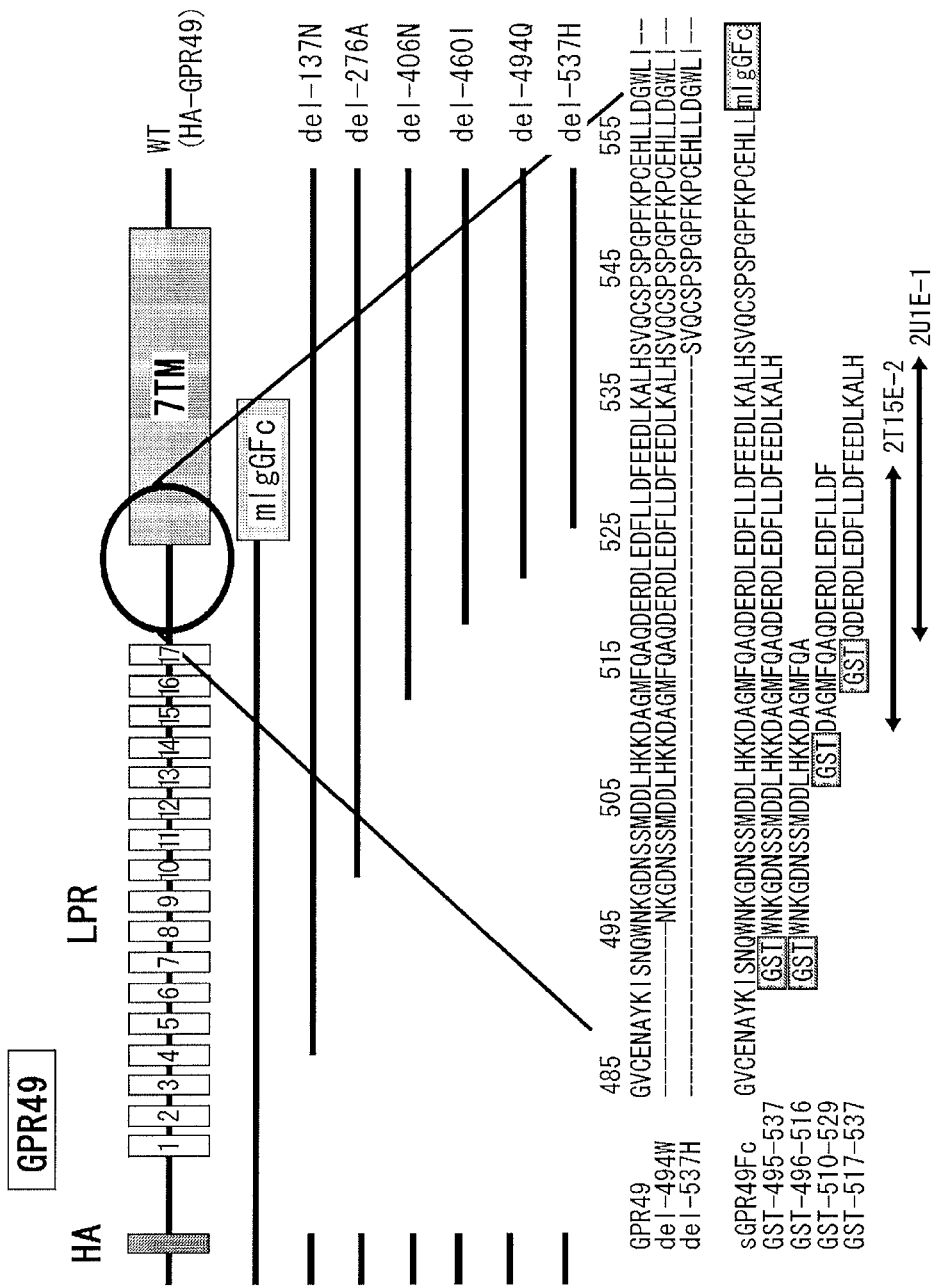
FIG. 13 depicts the structure of GPR49 and the regions included in the deletion mutants and GST-fusion proteins.
Figure 14:
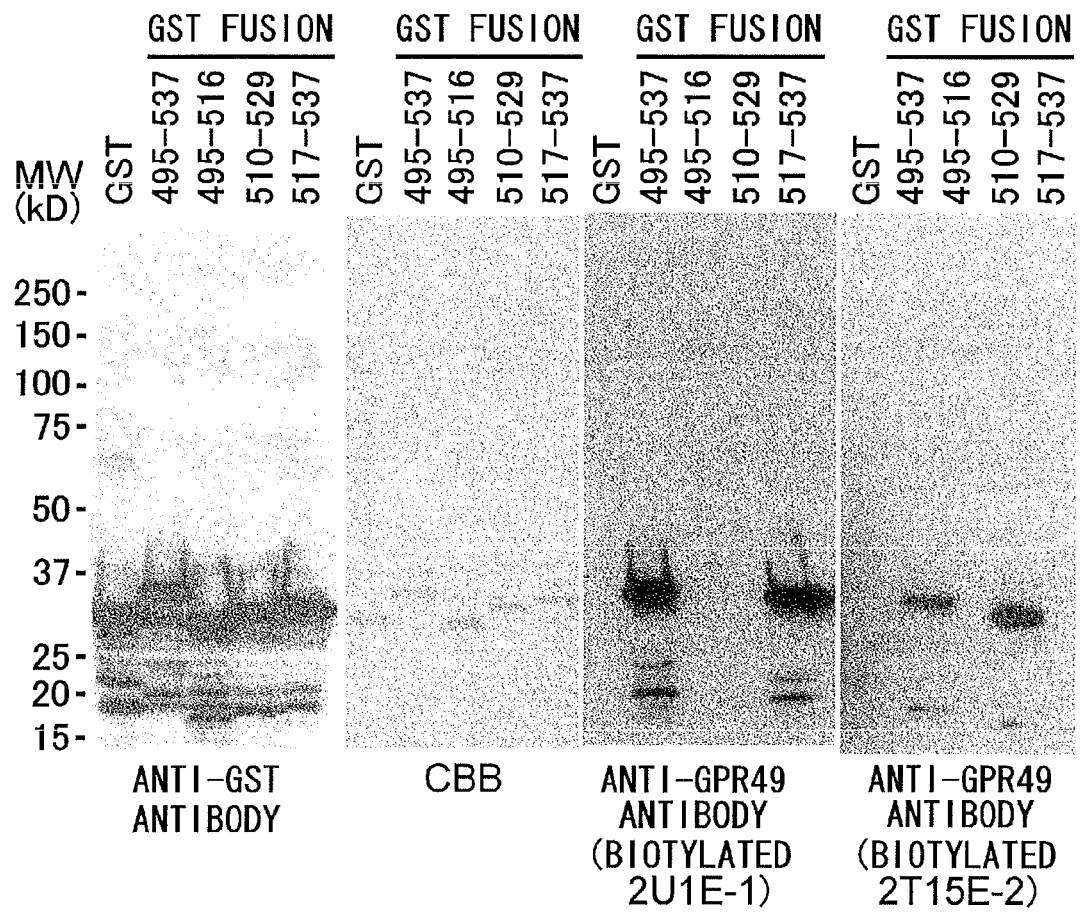
FIG. 14 depicts a series of photographs showing the reactivity of 2U1E-1 and 2T15E-2 with GST-fusion proteins by WB.

As a result of analyzing 2U1E-1 which recognizes the 40-kDa band through WB by constructing a deletion mutant GPR49 expression vector, an epitope was found to exist in the amino acids from positions 495 to 537. To narrow the region, the amino acids from positions 495 to 537, 495 to 516, 510 to 529, and 517 to 537 were fused and expressed as GST fusion proteins. The amino acid sequences of GPR49 included in each of the GST fusion proteins are shown in FIG. 13. As a result of analysis by Western blotting using the expression products, as shown in FIG. 14, the amino acid region from position 517 to 537 was found to be the epitope for 2U1E-1. Similarly, when an epitope of the 2T15E-2 antibody which also recognizes the 40-kDa fragment was analyzed, an epitope existed in the amino acid region from position 510 to 529. From these results, the 40-kDa protein resulting from cleavage can be said to be a molecule comprising the sequence at least up to amino acid position 510.

Example 19

Reactivity of an Anti-GPR49 Monoclonal Antibody with Mouse GPR49

Figure 15:
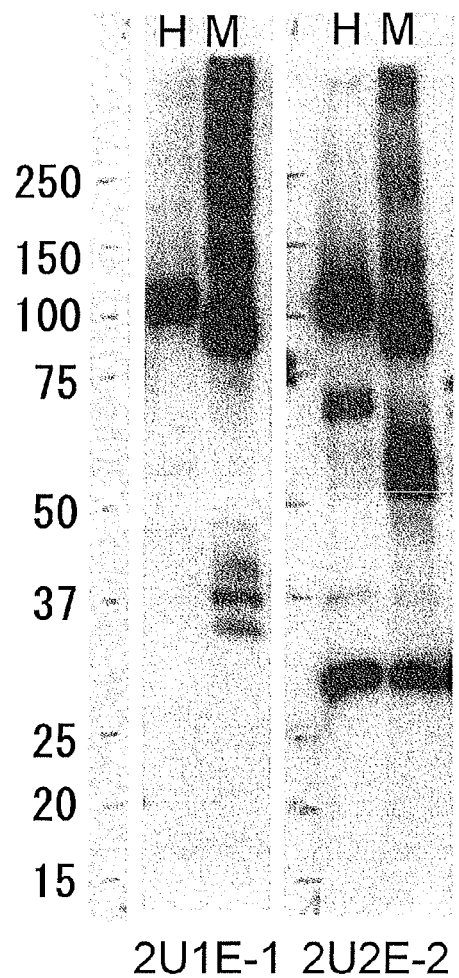
FIG. 15 depicts a photograph showing the reactivity of monoclonal antibodies 2U1E-1 and 2U2E-2 against mouse GPR49 by WB. Both antibodies react with human (H) and mouse (M) GPR49.

As shown in FIG. 15, when mouse GPR49 was incorporated into an expression vector, the protein was expressed transiently in 293T cells, and then the cell lysate was analyzed by WB, the antibody was found to also react against mouse GPR49.

Example 20

Evaluation of Binding Activity by Flow Cytometry (FACS)

The reactivity of 2T15E-2 antibody to human cancer cell lines were analyzed by flow cytometry. Human cancer cell lines suspended in a FACS buffer (2% FBS/PBS/0.05% NaN$_3$) were diluted to 1×10$^6$ cells/mL with the FACS buffer, and the solutions were then dispensed into a Falcon 353910 round-bottom 96-well plate at 50 μL/well. 2T15E-2 antibody diluted to a concentration of 10 μg/mL was added, and this was reacted for 60 minutes on ice. Next, the cells were washed once with the FACS buffer. After adding Goat F(ab')$_2$ fragment anti-mouse IgG (Fcγ)-FITC (Beckman Coulter) as a secondary antibody to the wells containing the cells, this was reacted for 30 minutes on ice. After the reaction, the supernatant was removed by centrifugation, and then the cells were suspended in 100 μL of FACS buffer containing propidium iodide (PI) and then subjected to flow cytometry. A FACS Calibur (Becton Dickinson) was used for the flow cytometry. The viable cell population was gated with a forward scatter-side scatter dot blot, an FL1 histogram was made of the cells contained in the population, and binding activity thereof was evaluated.

Figure 16:
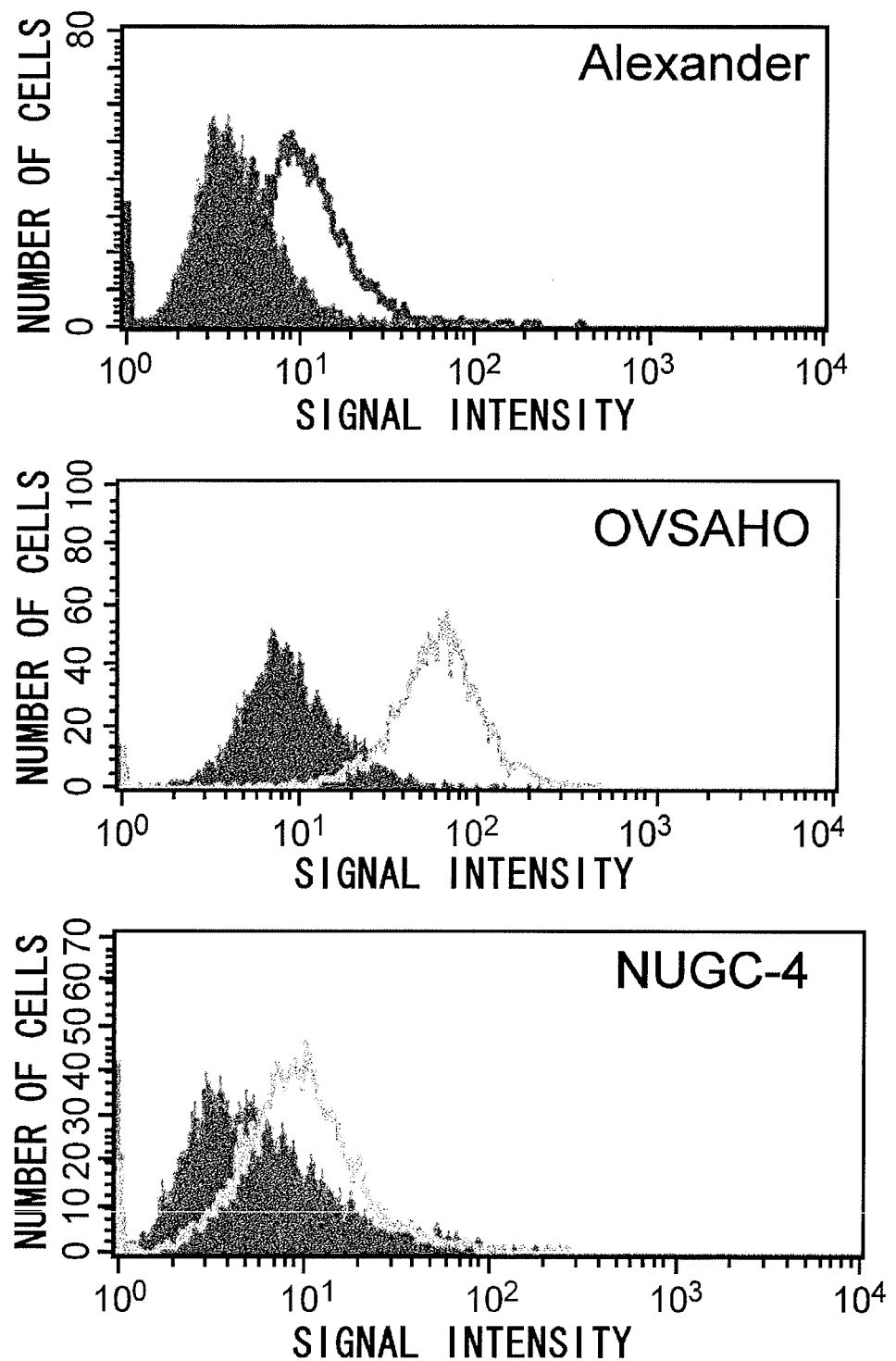
FIG. 16 shows the results of evaluating binding activity by flow cytometry (FACS). The peaks indicated with a solid line show the reactivity to cancer cell lines, and the shaded regions show the peaks obtained when the cells are treated without antibodies. The horizontal axis indicates signal intensity determined by the binding degree of FITC-conjugated antibodies, and the vertical axis indicates the number of cells.

In flow cytometry analyses using ovarian cancer cell line OVSAHO, hepatocellular carcinoma cell line Alexander, and gastric cancer cell line NUGC-4, the peaks clearly shifted compared with the peaks obtained without a primary antibody; therefore, this showed that the GPR49 molecule exists on the cell membranes of these cell lines (FIG. 16). The peaks indicated with a solid line indicate the reactivity with cancer cell lines, and the shaded regions represent the peaks obtained when the reactions are carried out without antibodies. The horizontal axis indicates intensity of signals according to the degree of bonding by the FITC-conjugated antibodies, and the vertical axis indicates the number of cells.

INDUSTRIAL APPLICABILITY

Antibodies specific to the GPR49 proteins in the present invention can be used as diagnostic agents for gastric cancer, colon cancer, hepatocellular carcinoma, lung cancer, prostate cancer, ovarian cancer, Ewing's sarcoma, glioma, and such. Diagnostic agents of the present invention are useful for diagnosis of primary or metastatic cancer. Specifically, detection of a GPR49 protein included in a biological sample collected from a patient determines possibility of cancer in the patient. Alternatively, detection of the localization of GPR49-expressing cells in vivo, allows detection of the presence of gastric cancer, colon cancer, hepatocellular carcinoma, lung cancer, prostate cancer, ovarian cancer, Ewing's sarcoma, and glioma in vivo.

Furthermore, anti-GPR49 antibodies having cytotoxic activity of the present invention are useful for treating or preventing cancers expressing GPR49 protein. Specifically, cytotoxic agents or cell growth inhibitors for cancer cells from various types of cancers such as gastric cancer, colon cancer, hepatocellular carcinoma, lung cancer, prostate cancer, ovarian cancer, Ewing's sarcoma, and glioma are provided based on the present invention. The cytotoxic agents or cell growth inhibitors for cancer cells according to the present invention can be applied to both primary and metastatic cancers.

Moreover, anti-GPR49 antibodies having cytotoxic activity according to the present invention can be used as therapeutic agents against various types of cancers such as gastric cancer, colon cancer, hepatocellular carcinoma, lung cancer, prostate cancer, ovarian cancer, Ewing's sarcoma, and glioma. In the present invention, anti-GPR49 antibodies are also useful as therapeutic agents against both primary and metastatic cancers.

In addition, antibody-encoding genes of the present invention, and recombinant cells transformed by these genes can be used to produce recombinant antibodies having the above-mentioned effects or having more preferable effects.

The invention claimed is:

1. An antibody that binds to a GPR49 protein comprising the amino acid sequence of SEQ ID NO: 1, wherein the antibody has cell proliferation inhibitory activity against cells expressing the GPR49 protein, and wherein the antibody binds to a 40 kDa C-terminal fragment of the GPR49 protein, and wherein said 40 kDa fragment comprises the amino acids 510 to 529 of SEQ ID NO: 1 and wherein said antibody comprises a human constant region, wherein the antibody is selected from any of (1) to (3) below;
   (1) an antibody comprising an H chain having the amino acid sequence of SEQ ID NO: 15 as CDR1, the amino acid sequence of SEQ ID NO: 16 as CDR2, and the amino acid sequence of SEQ ID NO: 17 as CDR3, and an L chain having the amino acid sequence of SEQ ID NO: 20 as CDR1, the amino acid sequence of SEQ ID NO: 21 as CDR2, and the amino acid sequence of SEQ ID NO: 22 as CDR3;
   (2) an antibody having one or more amino acid conservative substitutions in the antibody of (1), which has equivalent activity as the antibody of (1); and
   (3) an antibody that binds to the same epitope as the GPR49 protein epitope bound by the antibody (1), which has equivalent activity as the antibody of (1), wherein said epitope consisting SEQ ID NO: 86.

2. The antibody of claim 1, wherein the cell proliferation inhibitory activity is cytotoxic activity.

3. The antibody of claim 2, wherein the cytotoxic activity is antibody-dependent cytotoxic activity.

4. The antibody of claim 2, wherein the cytotoxic activity is complement-dependent cytotoxic activity.

5. The antibody of claim 1, wherein a cytotoxic substance is bound to the antibody.

6. The antibody of claim 5, wherein the antibody has an internalizing activity.

7. The antibody of claim 1, which suppresses cancer cell proliferation.

8. The antibody of claim 7, wherein the cancer cell is any one of gastric cancer cells, colon cancer cells, liver cancer cells, lung cancer cells, ovarian cancer cells, Ewing's sarcoma cells, or glioma cells.

9. The antibody of claim 1, wherein the antibody is a chimeric antibody, or a humanized antibody.

10. A pharmaceutical composition comprising the antibody of claim 1.

11. A cell proliferation-suppressing agent comprising the antibody of claim 1.

12. An anticancer agent comprising the antibody of claim 1.

13. The anticancer agent of claim 12, wherein the cancer is any cancer selected from the group consisting of gastric cancer, colon cancer, hepatocellular carcinoma, lung cancer, ovarian cancer, Ewing's sarcoma, and glioma.

* * * * *

SEQUENCE LISTING

```
<160> NUMBER OF SEQ ID NOS: 86

<210> SEQ ID NO 1
<211> LENGTH: 907
<212> TYPE: PRT
<213> ORGANISM: Homo sapiens

<400> SEQUENCE: 1

Met Asp Thr Ser Arg Leu Gly Val Leu Leu Ser Leu Pro Val Leu Leu
 1               5                  10                  15
```

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
        275                 280                 285

Tyr Asp Asn Pro Ile Gln Phe Val Gly Arg Ser Ala Phe Gln His Leu
    290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
            340                 345                 350

Asn Leu Gln Val Leu Asp Leu Ser Tyr Asn Leu Leu Glu Asp Leu Pro
        355                 360                 365

Ser Phe Ser Val Cys Gln Lys Leu Gln Lys Ile Asp Leu Arg His Asn
    370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile His Pro Asn
                405                 410                 415

Ala Phe Ser Thr Leu Pro Ser Leu Ile Lys Leu Asp Leu Ser Ser Asn
        420                 425                 430

Leu Leu Ser Ser Phe Pro Ile Thr Gly Leu His Gly Leu Thr His Leu

-continued

```
                435                 440                 445
Lys Leu Thr Gly Asn His Ala Leu Gln Ser Leu Ile Ser Ser Glu Asn
450                 455                 460

Phe Pro Glu Leu Lys Val Ile Glu Met Pro Tyr Ala Tyr Gln Cys Cys
465                 470                 475                 480

Ala Phe Gly Val Cys Glu Asn Ala Tyr Lys Ile Ser Asn Gln Trp Asn
                485                 490                 495

Lys Gly Asp Asn Ser Ser Met Asp Asp Leu His Lys Lys Asp Ala Gly
                500                 505                 510

Met Phe Gln Ala Gln Asp Glu Arg Asp Leu Glu Asp Phe Leu Leu Asp
                515                 520                 525

Phe Glu Glu Asp Leu Lys Ala Leu His Ser Val Gln Cys Ser Pro Ser
530                 535                 540

Pro Gly Pro Phe Lys Pro Cys Glu His Leu Leu Asp Gly Trp Leu Ile
545                 550                 555                 560

Arg Ile Gly Val Trp Thr Ile Ala Val Leu Ala Leu Thr Cys Asn Ala
                565                 570                 575

Leu Val Thr Ser Thr Val Phe Arg Ser Pro Leu Tyr Ile Ser Pro Ile
                580                 585                 590

Lys Leu Leu Ile Gly Val Ile Ala Ala Val Asn Met Leu Thr Gly Val
                595                 600                 605

Ser Ser Ala Val Leu Ala Gly Val Asp Ala Phe Thr Phe Gly Ser Phe
610                 615                 620

Ala Arg His Gly Ala Trp Trp Glu Asn Gly Val Gly Cys His Val Ile
625                 630                 635                 640

Gly Phe Leu Ser Ile Phe Ala Ser Glu Ser Ser Val Phe Leu Leu Thr
                645                 650                 655

Leu Ala Ala Leu Glu Arg Gly Phe Ser Val Lys Tyr Ser Ala Lys Phe
                660                 665                 670

Glu Thr Lys Ala Pro Phe Ser Ser Leu Lys Val Ile Ile Leu Leu Cys
                675                 680                 685

Ala Leu Leu Ala Leu Thr Met Ala Ala Val Pro Leu Leu Gly Gly Ser
690                 695                 700

Lys Tyr Gly Ala Ser Pro Leu Cys Leu Pro Leu Pro Phe Gly Glu Pro
705                 710                 715                 720

Ser Thr Met Gly Tyr Met Val Ala Leu Ile Leu Leu Asn Ser Leu Cys
                725                 730                 735

Phe Leu Met Met Thr Ile Ala Tyr Thr Lys Leu Tyr Cys Asn Leu Asp
                740                 745                 750

Lys Gly Asp Leu Glu Asn Ile Trp Asp Cys Ser Met Val Lys His Ile
                755                 760                 765

Ala Leu Leu Leu Phe Thr Asn Cys Ile Leu Asn Cys Pro Val Ala Phe
                770                 775                 780

Leu Ser Phe Ser Ser Leu Ile Asn Leu Thr Phe Ile Ser Pro Glu Val
785                 790                 795                 800

Ile Lys Phe Ile Leu Leu Val Val Pro Leu Pro Ala Cys Leu Asn
                805                 810                 815

Pro Leu Leu Tyr Ile Leu Phe Asn Pro His Phe Lys Glu Asp Leu Val
                820                 825                 830

Ser Leu Arg Lys Gln Thr Tyr Val Trp Thr Arg Ser Lys His Pro Ser
                835                 840                 845

Leu Met Ser Ile Asn Ser Asp Asp Val Glu Lys Gln Ser Cys Asp Ser
850                 855                 860
```

```
Thr Gln Ala Leu Val Thr Phe Thr Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu
            900                 905

<210> SEQ ID NO 2
<211> LENGTH: 2880
<212> TYPE: DNA
<213> ORGANISM: Homo sapiens

<400> SEQUENCE: 2
tgctgctctc cgcccgcgtc cggctcgtgg ccccctactt cgggcaccat ggacacctcc      60
cggctcggtg tgctcctgtc cttgcctgtg ctgctgcagc tggcgaccgg gggcagctct     120
cccaggtctg tgtgttgct gaggggctgc cccacacact gtcattgcga gcccgacggc     180
aggatgttgc tcagggtgga ctgctccgac ctggggctct cggagctgcc ttccaacctc     240
agcgtcttca cctcctacct agacctcagt atgaacaaca tcagtcagct gctcccgaat     300
cccctgccca gtctccgctt cctggaggag ttacgtcttg cgggaaacgc tctgacatac     360
attcccaagg gagcattcac tggcctttac agtcttaaag ttcttatgct gcagaataat     420
cagctaagac acgtacccac agaagctctg cagaatttgc gaagccttca atccctgcgt     480
ctggatgcta accacatcag ctatgtgccc caagctgttt cagtggcct gcattccctg     540 aggcacctgt ggctggatga caatgcgtta acagaaatcc ccgtccaggc ttttagaagt     600
ttatcggcat tgcaagccat gaccttggcc ctgaacaaaa tacaccacat accagactat     660
gcctttggaa acctctccag cttggtagtt ctacatctcc ataacaatag aatccactcc     720
ctgggaaaga aatgctttga tgggctccac agcctagaga ctttagattt aaattacaat     780
aaccttgatg aattccccac tgcaattagg acactctcca accttaaaga actaggattt     840
catagcaaca atatcaggtc gatacctgag aaagcatttg taggcaaccc ttctcttatt     900
acaatacatt tctatgacaa tcccatccaa tttgttggga gatctgcttt tcaacattta     960
cctgaactaa gaacactgac tctgaatggt gcctcacaaa taactgaatt tcctgattta    1020
actggaactg caaacctgga gagtctgact ttaactggag cacagatctc atctcttcct    1080
caaaccgtct gcaatcagtt acctaatctc caagtgctag atctgtctta caactctatta    1140 gaagatttac ccagtttttc agtctgccaa aagcttcaga aaattgacct aagacataat    1200
gaaatctacg aaattaaagt tgacactttc agcagttgc ttagcctccg atcgctgaat    1260
ttggcttgga acaaaattgc tattattcac cccaatgcat tttccacttt gccatcccta    1320
ataaagctgg acctatcgtc caacctcctg tcgtcttttc ctataactgg gttacatggt    1380
ttaactcact taaaattaac aggaaatcat gccttacaga gcttgatatc atctgaaaac    1440
tttccagaac tcaaggttat agaaatgcct tatgcttacc agtgctgtgc atttggagtg    1500
tgtgagaatg cctataagat ttctaatcaa tggaataaag gtgacaacag cagtatggac    1560
gaccttcata agaagatgc tggaatgttt caggctcaag atgaacgtga ccttgaagat    1620
ttcctgcttg actttgagga gacctgaaa gcccttcatt cagtgcagtg ttcaccttcc    1680 ccaggccct tcaaaccctg tgaacacctg cttgatggct ggctgatcag aattggagtg    1740
tggaccatag cagttctggc acttacttgt aatgctttgg tgacttcaac agttttcaga    1800
tcccctctgt acatttcccc cattaaactg ttaattgggg tcatcgcagc agtgaacatg    1860
```

```
ctcacgggag tctccagtgc cgtgctggct ggtgtggatg cgttcacttt tggcagcttt    1920
gcacgacatg gtgcctggtg ggagaatggg gttggttgcc atgtcattgg ttttttgtcc    1980
atttttgctt cagaatcatc tgttttcctg cttactctgg cagccctgga gcgtgggttc    2040
tctgtgaaat attctgcaaa atttgaaacg aaagctccat tttctagcct gaaagtaatc    2100
attttgctct gtgccctgct ggccttgacc atggccgcag ttcccctgct gggtggcagc    2160
aagtatggcg cctcccctct ctgcctgcct ttgccttttg gggagcccag caccatgggc    2220
tacatggtcg ctctcatctt gctcaattcc ctttgcttcc tcatgatgac cattgcctac    2280
accaagctct actgcaattt ggacaaggga gacctggaga tatttggga ctgctctatg     2340 gtaaaacaca ttgccctgtt gctcttcacc aactgcatcc taaactgccc tgtggctttc    2400
ttgtccttct cctctttaat aaaccttaca tttatcagtc ctgaagtaat taagtttatc    2460
cttctggtgg tagtcccact tcctgcatgt ctcaatcccc ttctctacat cttgttcaat    2520
cctcacttta aggaggatct ggtgagcctg agaaagcaaa cctacgtctg gacaagatca    2580
aaacacccaa gcttgatgtc aattaactct gatgatgtcg aaaaacagtc ctgtgactca    2640
actcaagcct tggtaacctt taccagctcc agcatcactt atgacctgcc tcccagttcc    2700
gtgccatcac cagcttatcc agtgactgag agctgccatc tttcctctgt ggcatttgtc    2760
ccatgtctct aattaatatg tgaaggaaaa tgttttcaaa ggttgagaac ctgaaaatgt    2820
gagattgagt atatcagagc agtaattaat aagaagagct gaggtgaaac tcggtttaaa    2880

<210> SEQ ID NO 3
<211> LENGTH: 354
<212> TYPE: DNA
<213> ORGANISM: Mus musculus

<400> SEQUENCE: 3
gaggtccagc tgcaacagtc tggacctgag ctggtgaagc ctggggattc agtgaagatg      60
tcctgcaagg cttctggcta cacattcact gactactaca tggactgggt gaagcagagc     120
catggaaaga gccttgagtg gattggatat atttatccta acaatggtgg tactagctac     180
aatcagaagt tcaagggcaa ggccacattg actgtagaca agtcctccag cacagcctac     240
atggagctcc acagcctgac atctgaggac tctgcagtct attactgtgc aagaccatac     300
tatagtaact cgtttgctta ctggggccaa gggactctgg tcactgtctc tgca           354

<210> SEQ ID NO 4
<211> LENGTH: 118
<212> TYPE: PRT
<213> ORGANISM: Mus musculus

<400> SEQUENCE: 4

Glu Val Gln Leu Gln Gln Ser Gly Pro Glu Leu Val Lys Pro Gly Asp
1               5                   10                  15

Ser Val Lys Met Ser Cys Lys Ala Ser Gly Tyr Thr Phe Thr Asp Tyr
            20                  25                  30

Tyr Met Asp Trp Val Lys Gln Ser His Gly Lys Ser Leu Glu Trp Ile
        35                  40                  45

Gly Tyr Ile Tyr Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
```

85                  90                  95
Ala Arg Pro Tyr Tyr Ser Asn Ser Phe Ala Tyr Trp Gly Gln Gly Thr
            100                 105                 110

Leu Val Thr Val Ser Ala
        115

<210> SEQ ID NO 5
<211> LENGTH: 5
<212> TYPE: PRT
<213> ORGANISM: Mus musculus

<400> SEQUENCE: 5

Asp Tyr Tyr Met Asp
1               5

<210> SEQ ID NO 6
<211> LENGTH: 17
<212> TYPE: PRT
<213> ORGANISM: Mus musculus

<400> SEQUENCE: 6

Tyr Ile Tyr Pro Asn Asn Gly Gly Thr Ser Tyr Asn Gln Lys Phe Lys
1               5                   10                  15

Gly

<210> SEQ ID NO 7
<211> LENGTH: 9
<212> TYPE: PRT
<213> ORGANISM: Mus musculus

<400> SEQUENCE: 7

Pro Tyr Tyr Ser Asn Ser Phe Ala Tyr
1               5

<210> SEQ ID NO 8
<211> LENGTH: 324
<212> TYPE: DNA
<213> ORGANISM: Mus musculus

<400> SEQUENCE: 8
cagattgttc tcacccagtc tccagcaatc atgtctgcat ctccagggga gaaggtcacc      60
atgacctgca gggccagctc aagtgtaagt tccagttact tgcactggta ccagcagaag     120
ccaggatctt cccccaaact ctggatttat agcacatcca acctggcttc aggagtccca     180
gctcgcttca gtggcagtgg gtctgggacc tcttactctc tcacaatcag cagtgtggag     240
gctgaggatg ctgccactta ttactgccag cagtatgata gttccccatt cacgttcggc     300
acggggacaa aattggaaat aaaa                                            324

<210> SEQ ID NO 9
<211> LENGTH: 108
<212> TYPE: PRT
<213> ORGANISM: Mus musculus

<400> SEQUENCE: 9

Gln Ile Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Asp Ser Ser Pro
                85                  90                  95

Phe Thr Phe Gly Thr Gly Thr Lys Leu Glu Ile Lys
            100                 105

<210> SEQ ID NO 10
<211> LENGTH: 12
<212> TYPE: PRT
<213> ORGANISM: Mus musculus

<400> SEQUENCE: 10

Arg Ala Ser Ser Ser Val Ser Ser Ser Tyr Leu His
1               5                   10

<210> SEQ ID NO 11
<211> LENGTH: 7
<212> TYPE: PRT
<213> ORGANISM: Mus musculus

<400> SEQUENCE: 11

Ser Thr Ser Asn Leu Ala Ser
1               5

<210> SEQ ID NO 12
<211> LENGTH: 9
<212> TYPE: PRT
<213> ORGANISM: Mus musculus

<400> SEQUENCE: 12

Gln Gln Tyr Asp Ser Ser Pro Phe Thr
1               5

<210> SEQ ID NO 13
<211> LENGTH: 360
<212> TYPE: DNA
<213> ORGANISM: Mus musculus

<400> SEQUENCE: 13
caggtccagc tgcagcagcc tggggctgaa ctggtggagc ctggggcttc agtgaagttg    60
tcctgcaagg cttctggcta caccttcacc aactactata tgtactgggt gaagcagagg   120
cctggacaag gccttgagtg gattgggggg attaatccta caatggtgg tactaacttc    180 aatgagaagt tcaagagcaa ggccacactg actgtagaca atcctccag cacagcctac    240 atgcaactca gcagcctgac atctgaggac tctgcggtct attactgtac aggaatctac    300
tataggtaca ctggcacttt cggtgtctgg ggcgcaggga ccacggtcac cgtctcctca    360

<210> SEQ ID NO 14
<211> LENGTH: 120
<212> TYPE: PRT
<213> ORGANISM: Mus musculus

<400> SEQUENCE: 14

Gln Val Gln Leu Gln Gln Pro Gly Ala Glu Leu Val Glu Pro Gly Ala
1               5                   10                  15

Ser Val Lys Leu Ser Cys Lys Ala Ser Gly Tyr Thr Phe Thr Asn Tyr
                20                  25                  30

```
Tyr Met Tyr Trp Val Lys Gln Arg Pro Gly Gln Gly Leu Glu Trp Ile
        35                  40                  45

Gly Gly Ile Asn Pro Asn Asn Gly Gly Thr Asn Phe Asn Glu Lys Phe
 50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Gly Ile Tyr Tyr Arg Tyr Asn Trp His Phe Gly Val Trp Gly Ala
                100                 105                 110

Gly Thr Thr Val Thr Val Ser Ser
        115                 120

<210> SEQ ID NO 15
<211> LENGTH: 5
<212> TYPE: PRT
<213> ORGANISM: Mus musculus

<400> SEQUENCE: 15

Asn Tyr Tyr Met Tyr
1               5

<210> SEQ ID NO 16
<211> LENGTH: 17
<212> TYPE: PRT
<213> ORGANISM: Mus musculus

<400> SEQUENCE: 16

Gly Ile Asn Pro Asn Asn Gly Gly Thr Asn Phe Asn Glu Lys Phe Lys
1               5                   10                  15

Ser

<210> SEQ ID NO 17
<211> LENGTH: 11
<212> TYPE: PRT
<213> ORGANISM: Mus musculus

<400> SEQUENCE: 17

Ile Tyr Tyr Arg Tyr Asn Trp His Phe Gly Val
1               5                   10

<210> SEQ ID NO 18
<211> LENGTH: 336
<212> TYPE: DNA
<213> ORGANISM: Mus musculus

<400> SEQUENCE: 18
gatgttttga tgacccaaac tccactctcc ctgcctgtca gtcttggaga tcaggcctcc      60
atctcttgca gatctagtca gaccattgta catagtaatg aaacacccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
tacagagtgg aggctgagga tctgggaatt tattactgct ttcaaggttc acatgttccg     300
tggacattcg gtggaggcac caagctggaa atcaaa                               336

<210> SEQ ID NO 19
<211> LENGTH: 112
<212> TYPE: PRT
<213> ORGANISM: Mus musculus
```

<400> SEQUENCE: 19

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Tyr Arg Val Glu Ala Glu Asp Leu Gly Ile Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 20
<211> LENGTH: 16
<212> TYPE: PRT
<213> ORGANISM: Mus musculus

<400> SEQUENCE: 20

Arg Ser Ser Gln Thr Ile Val His Ser Asn Gly Asn Thr Tyr Leu Glu
1               5                   10                  15

<210> SEQ ID NO 21
<211> LENGTH: 7
<212> TYPE: PRT
<213> ORGANISM: Mus musculus

<400> SEQUENCE: 21

Lys Val Ser Asn Arg Phe Ser
1               5

<210> SEQ ID NO 22
<211> LENGTH: 9
<212> TYPE: PRT
<213> ORGANISM: Mus musculus

<400> SEQUENCE: 22

Phe Gln Gly Ser His Val Pro Trp Thr
1               5

<210> SEQ ID NO 23
<211> LENGTH: 342
<212> TYPE: DNA
<213> ORGANISM: Mus musculus

<400> SEQUENCE: 23
gaagtgaagc tggtggagtc tgggggagac ttagtgaagc tggagggtc cctgaaactc      60 tcctgtgcag cctctggatt catttcagt acctatgcca tgtcttgggt tcgccagatt     120
ccagagaaga ggctggagtg ggtcgcatcc attagtcctg atggtaacac cttctatcca    180
gacagtctga agggccgatt caccatctcc agagataatg tcaggaacat cctgtacctg    240
cagatgagca gtctcaggtc tgaggacacg gccatgtatt actgtgcagt tactgggacg    300
tttgcttact ggggccaagg gactctggtc actgtatctg ga                       342

<210> SEQ ID NO 24

```
<211> LENGTH: 114
<212> TYPE: PRT
<213> ORGANISM: Mus musculus

<400> SEQUENCE: 24

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Ile Phe Ser Thr Tyr
            20                  25                  30

Ala Met Ser Trp Val Arg Gln Ile Pro Glu Lys Arg Leu Glu Trp Val
        35                  40                  45

Ala Ser Ile Ser Pro Asp Gly Asn Thr Phe Tyr Pro Asp Ser Leu Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Val Thr Gly Thr Phe Ala Tyr Trp Gly Gln Gly Thr Leu Val Thr Val
            100                 105                 110

Ser Gly

<210> SEQ ID NO 25
<211> LENGTH: 5
<212> TYPE: PRT
<213> ORGANISM: Mus musculus

<400> SEQUENCE: 25

Thr Tyr Ala Met Ser
1               5

<210> SEQ ID NO 26
<211> LENGTH: 16
<212> TYPE: PRT
<213> ORGANISM: Mus musculus

<400> SEQUENCE: 26

Ser Ile Ser Pro Asp Gly Asn Thr Phe Tyr Pro Asp Ser Leu Lys Gly
1               5                   10                  15

<210> SEQ ID NO 27
<211> LENGTH: 6
<212> TYPE: PRT
<213> ORGANISM: Mus musculus

<400> SEQUENCE: 27

Thr Gly Thr Phe Ala Tyr
1               5

<210> SEQ ID NO 28
<211> LENGTH: 336
<212> TYPE: DNA
<213> ORGANISM: Mus musculus

<400> SEQUENCE: 28
gatgttttga tgacccaaac tccactctcc ctacctgtca gtcttggaga tcaagcctcc      60
atctcttgca gatctagtca gaacattcta catagtgatg aaacacctta tttagagtgg     120
tttctgcaga aaccaggcca gtctccaaag ctcctgatct tcaaaatttc caaccgattt     180
cctggggtcc cagacaggtt cagtggcagt ggatcaggga cagatttcac actcaagatc     240
agcagagtgg aggctgagga tctgggagtt tactactgct ttcaaagttc acatgttccg     300
```
tacacgttcg gagggggggac caagctggaa ataaaa                                    336

<210> SEQ ID NO 29
<211> LENGTH: 112
<212> TYPE: PRT
<213> ORGANISM: Mus musculus

<400> SEQUENCE: 29

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Leu His Ser
            20                  25                  30

Asp Gly Asn Thr Tyr Leu Glu Trp Phe Leu Gln Lys Pro Gly Gln Ser
        35                  40                  45

Pro Lys Leu Leu Ile Phe Lys Ile Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Ser His Val Pro Tyr Thr Phe Gly Gly Gly Thr Lys Leu Glu Ile Lys
            100                 105                 110

<210> SEQ ID NO 30
<211> LENGTH: 16
<212> TYPE: PRT
<213> ORGANISM: Mus musculus

<400> SEQUENCE: 30

Arg Ser Ser Gln Asn Ile Leu His Ser Asp Gly Asn Thr Tyr Leu Glu
1               5                   10                  15

<210> SEQ ID NO 31
<211> LENGTH: 7
<212> TYPE: PRT
<213> ORGANISM: Mus musculus

<400> SEQUENCE: 31

Lys Ile Ser Asn Arg Phe Pro
1               5

<210> SEQ ID NO 32
<211> LENGTH: 9
<212> TYPE: PRT
<213> ORGANISM: Mus musculus

<400> SEQUENCE: 32

Phe Gln Ser Ser His Val Pro Tyr Thr
1               5

<210> SEQ ID NO 33
<211> LENGTH: 348
<212> TYPE: DNA
<213> ORGANISM: Mus musculus

<400> SEQUENCE: 33
caggtccagc tgcagcagtc tggagctgag ctggtaaggc ctgggacttc agtgaagatg      60
tcctgcaagg ctgctggata caccttcact aactcctgga taggttgggt aaagcagagg     120
cctggacatg gccttgagtg gattggagat atttaccctg aggtgattta ctactaactac     180

```
aatgagaaat tcaagggcaa ggccacactg actgcagaca catcctccag cacagcctac    240
atgcagctca gcagcctgac atctgaggac gctgccatct attactgtac aagaggtgat    300
ggttactttg actactgggg ccaaggcacc actctcacag tctcctca                 348
```

<210> SEQ ID NO 34
<211> LENGTH: 116
<212> TYPE: PRT
<213> ORGANISM: Mus musculus

<400> SEQUENCE: 34

```
Gln Val Gln Leu Gln Gln Ser Gly Ala Glu Leu Val Arg Pro Gly Thr
1               5                   10                  15
Ser Val Lys Met Ser Cys Lys Ala Ala Gly Tyr Thr Phe Thr Asn Ser
            20                  25                  30
Trp Ile Gly Trp Val Lys Gln Arg Pro Gly His Gly Leu Glu Trp Ile
        35                  40                  45
Gly Asp Ile Tyr Pro Gly Gly Asp Tyr Thr Asn Tyr Asn Glu Lys Phe
    50                  55                  60
Lys Gly Lys Ala Thr Leu Thr Ala Asp Thr Ser Ser Ser Thr Ala Tyr
65                  70                  75                  80
Met Gln Leu Ser Ser Leu Thr Ser Glu Asp Ala Ala Ile Tyr Tyr Cys
                85                  90                  95
Thr Arg Gly Asp Gly Tyr Phe Asp Tyr Trp Gly Gln Gly Thr Thr Leu
            100                 105                 110
Thr Val Ser Ser
        115
```

<210> SEQ ID NO 35
<211> LENGTH: 5
<212> TYPE: PRT
<213> ORGANISM: Mus musculus

<400> SEQUENCE: 35

```
Asn Ser Trp Ile Gly
1               5
```

<210> SEQ ID NO 36
<211> LENGTH: 17
<212> TYPE: PRT
<213> ORGANISM: Mus musculus

<400> SEQUENCE: 36

```
Asp Ile Tyr Pro Gly Gly Asp Tyr Thr Asn Tyr Asn Glu Lys Phe Lys
1               5                   10                  15
Gly
```

<210> SEQ ID NO 37
<211> LENGTH: 7
<212> TYPE: PRT
<213> ORGANISM: Mus musculus

<400> SEQUENCE: 37

```
Gly Asp Gly Tyr Phe Asp Tyr
1               5
```

<210> SEQ ID NO 38
<211> LENGTH: 321
<212> TYPE: DNA
<213> ORGANISM: Mus musculus -continued

```
<400> SEQUENCE: 38
gacattgtga tgacccagtc tcacaaattc atgtccacat cagtaggaga cagggtcagc    60
atcacctgca aggccagtca ggatgtgagt attgatgtag cctggtatca acagagacca   120
ggacaatctc ctaaactact gatttactcg gcatcctacc ggtatactgg agtccctgat   180
cgcttcactg gcagtggatc tgggacggat ttcactttca ccgtcagcag tgtgcaggct   240
gaagacctgg cagtttatta ctgtcagcaa cattatagta ctcctccgac gttcggtgga   300
ggcaccaagc tggaaatcaa a                                             321

<210> SEQ ID NO 39
<211> LENGTH: 107
<212> TYPE: PRT
<213> ORGANISM: Mus musculus

<400> SEQUENCE: 39

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Ile Asp
            20                  25                  30

Val Ala Trp Tyr Gln Gln Arg Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Val Ser Ser Val Gln Ala
65                  70                  75                  80

Glu Asp Leu Ala Val Tyr Tyr Cys Gln Gln His Tyr Ser Thr Pro Pro
                85                  90                  95

Thr Phe Gly Gly Gly Thr Lys Leu Glu Ile Lys
            100                 105

<210> SEQ ID NO 40
<211> LENGTH: 11
<212> TYPE: PRT
<213> ORGANISM: Mus musculus

<400> SEQUENCE: 40

Lys Ala Ser Gln Asp Val Ser Ile Asp Val Ala
1               5                   10

<210> SEQ ID NO 41
<211> LENGTH: 7
<212> TYPE: PRT
<213> ORGANISM: Mus musculus

<400> SEQUENCE: 41

Ser Ala Ser Tyr Arg Tyr Thr
1               5

<210> SEQ ID NO 42
<211> LENGTH: 9
<212> TYPE: PRT
<213> ORGANISM: Mus musculus

<400> SEQUENCE: 42

Gln Gln His Tyr Ser Thr Pro Pro Thr
1               5

<210> SEQ ID NO 43
<211> LENGTH: 357
```

```
<212> TYPE: DNA
<213> ORGANISM: Mus musculus

<400> SEQUENCE: 43
caggtccagc tgcagcagtc tggagctgag ctggtaaggc ctgggacttc agtgaaggtg      60
tcctgcaagg cttctggata cgacttcact aattacttga tagagtgggt aaatcagagg     120
cctggacagg gccttgagtg gattggagtg attaatcctg gaagtggtgg tactaactac     180
aatgagaagt tcaagggcaa ggcaacactg actgcagaca atcctccag cactgcctac      240 atgcagctca gcagcctgac atctgatgac tctgcggtct atctctgtgc aagatattcc     300
ccgtatggta actactttga ctactggggc caaggcacca ctctcacagt ctcctca       357

<210> SEQ ID NO 44
<211> LENGTH: 119
<212> TYPE: PRT
<213> ORGANISM: Mus musculus

<400> SEQUENCE: 44

Gln Val Gln Leu Gln Gln Ser Gly Ala Glu Leu Val Arg Pro Gly Thr
1               5                  10                  15

Ser Val Lys Val Ser Cys Lys Ala Ser Gly Tyr Asp Phe Thr Asn Tyr
            20                  25                  30

Leu Ile Glu Trp Val Asn Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Asp Asp Ser Ala Val Tyr Leu Cys
                85                  90                  95

Ala Arg Tyr Ser Pro Tyr Gly Asn Tyr Phe Asp Tyr Trp Gly Gln Gly
            100                 105                 110

Thr Thr Leu Thr Val Ser Ser
        115

<210> SEQ ID NO 45
<211> LENGTH: 5
<212> TYPE: PRT
<213> ORGANISM: Mus musculus

<400> SEQUENCE: 45

Asn Tyr Leu Ile Glu
1               5

<210> SEQ ID NO 46
<211> LENGTH: 17
<212> TYPE: PRT
<213> ORGANISM: Mus musculus

<400> SEQUENCE: 46

Val Ile Asn Pro Gly Ser Gly Gly Thr Asn Tyr Asn Glu Lys Phe Lys
1               5                   10                  15

Gly

<210> SEQ ID NO 47
<211> LENGTH: 10
<212> TYPE: PRT
<213> ORGANISM: Mus musculus
```

<400> SEQUENCE: 47

Tyr Ser Pro Tyr Gly Asn Tyr Phe Asp Tyr
1               5                   10

<210> SEQ ID NO 48
<211> LENGTH: 321
<212> TYPE: DNA
<213> ORGANISM: Mus musculus

<400> SEQUENCE: 48

```
gacattgtga tgacccagtc tcacaaattc atgtccacat cagtaggaga cagggtcagc    60
atcacctgca gggccagtca ggatgtgggt actgctgtgg cctggtatca acagaaacca   120
gggcaatctc ctaaacttct gatttactgg gcatccaccc ggcacactgg agtccctgat   180
cgcttcacag gcagtggatc tgggacagat ttcactctca ccattaacaa tgtgcagtct   240
gaagacttgg cagattattt ctgtcagcaa tatagcagct atcctccgac gttcggtgga   300
ggcaccaagc tggaaatcaa a                                             321
```

<210> SEQ ID NO 49
<211> LENGTH: 107
<212> TYPE: PRT
<213> ORGANISM: Mus musculus

<400> SEQUENCE: 49

Asp Ile Val Met Thr Gln Ser His Lys Phe Met Ser Thr Ser Val Gly
1               5                   10                  15

Asp Arg Val Ser Ile Thr Cys Arg Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Asp Tyr Phe Cys Gln Gln Tyr Ser Ser Tyr Pro Pro
                85                  90                  95

Thr Phe Gly Gly Gly Thr Lys Leu Glu Ile Lys
            100                 105

<210> SEQ ID NO 50
<211> LENGTH: 11
<212> TYPE: PRT
<213> ORGANISM: Mus musculus

<400> SEQUENCE: 50

Arg Ala Ser Gln Asp Val Gly Thr Ala Val Ala
1               5                   10

<210> SEQ ID NO 51
<211> LENGTH: 7
<212> TYPE: PRT
<213> ORGANISM: Mus musculus

<400> SEQUENCE: 51

Trp Ala Ser Thr Arg His Thr
1               5

<210> SEQ ID NO 52
<211> LENGTH: 9

```
<212> TYPE: PRT
<213> ORGANISM: Mus musculus

<400> SEQUENCE: 52

Gln Gln Tyr Ser Ser Tyr Pro Pro Thr
1               5

<210> SEQ ID NO 53
<211> LENGTH: 4
<212> TYPE: PRT
<213> ORGANISM: Artificial Sequence
<220> FEATURE:
<223> OTHER INFORMATION: an artificially synthesized peptide sequence

<400> SEQUENCE: 53

Gly Gly Gly Ser
1

<210> SEQ ID NO 54
<211> LENGTH: 4
<212> TYPE: PRT
<213> ORGANISM: Artificial Sequence
<220> FEATURE:
<223> OTHER INFORMATION: an artificially synthesized peptide sequence

<400> SEQUENCE: 54

Ser Gly Gly Gly
1

<210> SEQ ID NO 55
<211> LENGTH: 5
<212> TYPE: PRT
<213> ORGANISM: Artificial Sequence
<220> FEATURE:
<223> OTHER INFORMATION: an artificially synthesized peptide sequence

<400> SEQUENCE: 55

Gly Gly Gly Gly Ser
1               5

<210> SEQ ID NO 56
<211> LENGTH: 5
<212> TYPE: PRT
<213> ORGANISM: Artificial Sequence
<220> FEATURE:
<223> OTHER INFORMATION: an artificially synthesized peptide sequence

<400> SEQUENCE: 56

Ser Gly Gly Gly Gly
1               5

<210> SEQ ID NO 57
<211> LENGTH: 6
<212> TYPE: PRT
<213> ORGANISM: Artificial Sequence
<220> FEATURE:
<223> OTHER INFORMATION: an artificially synthesized peptide sequence

<400> SEQUENCE: 57

Gly Gly Gly Gly Gly Ser
1               5

<210> SEQ ID NO 58
<211> LENGTH: 6
<212> TYPE: PRT
<213> ORGANISM: Artificial Sequence
<220> FEATURE:
```

<223> OTHER INFORMATION: an artificially synthesized peptide sequence

<400> SEQUENCE: 58

Ser Gly Gly Gly Gly Gly
1               5

<210> SEQ ID NO 59
<211> LENGTH: 7
<212> TYPE: PRT
<213> ORGANISM: Artificial Sequence
<220> FEATURE:
<223> OTHER INFORMATION: an artificially synthesized peptide sequence

<400> SEQUENCE: 59

Gly Gly Gly Gly Gly Gly Ser
1               5

<210> SEQ ID NO 60
<211> LENGTH: 7
<212> TYPE: PRT
<213> ORGANISM: Artificial Sequence
<220> FEATURE:
<223> OTHER INFORMATION: an artificially synthesized peptide sequence

<400> SEQUENCE: 60

Ser Gly Gly Gly Gly Gly Gly
1               5

<210> SEQ ID NO 61
<211> LENGTH: 23
<212> TYPE: DNA
<213> ORGANISM: Artificial Sequence
<220> FEATURE:
<223> OTHER INFORMATION: an artificially synthesized oligonucleotide
      sequence

<400> SEQUENCE: 61
ccaccagatt cttatcagac agg                                        23

<210> SEQ ID NO 62
<211> LENGTH: 21
<212> TYPE: DNA
<213> ORGANISM: Artificial Sequence
<220> FEATURE:
<223> OTHER INFORMATION: an artificially synthesized oligonucleotide
      sequence

<400> SEQUENCE: 62
gggccagtgg atagacagat g                                          21

<210> SEQ ID NO 63
<211> LENGTH: 23
<212> TYPE: DNA
<213> ORGANISM: Artificial Sequence
<220> FEATURE:
<223> OTHER INFORMATION: an artificially synthesized oligonucleotide
      sequence

<400> SEQUENCE: 63
gctcactgga tggtgggaag atg                                        23

<210> SEQ ID NO 64
<211> LENGTH: 366
<212> TYPE: DNA
<213> ORGANISM: Mus musculus

<400> SEQUENCE: 64

```
gaagtgcagc tggtggagtc tgggggaggc ttagtgaagc ctggagggtc cctgaaaatc    60
tcctgtgcag cctctggatt cacctccagt aactatgcca tgtcttgggt tcgtcagact   120
ccggagaaga ggctggagtg ggtcgcaacc attagtagtg gtggtggtta cacctactat   180
ccagacagtg agaaggggcg attcgccatt tccagagaca tgccaagaa caccctgtac   240 ctgcagatga gcggtctgag gtctgaggac acggccatgt attactgtgc aacacagctc   300
tactataggt cccattacta ttctatggac tactggggtc aaggatcctc agtcaccgtc   360
tcctca                                                               366
```

<210> SEQ ID NO 65
<211> LENGTH: 122
<212> TYPE: PRT
<213> ORGANISM: Mus musculus

<400> SEQUENCE: 65

```
Glu Val Gln Leu Val Glu Ser Gly Gly Gly Leu Val Lys Pro Gly Gly
1               5                   10                  15

Ser Leu Lys Ile Ser Cys Ala Ala Ser Gly Phe Thr Ser Ser Asn Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Gly Tyr Thr Tyr Tyr Pro Asp Ser Glu
    50                  55                  60

Lys Gly Arg Phe Ala Ile Ser Arg Asp Asn Ala Lys Asn Thr Leu Tyr
65                  70                  75                  80

Leu Gln Met Ser Gly Leu Arg Ser Glu Asp Thr Ala Met Tyr Tyr Cys
                85                  90                  95

Ala Thr Gln Leu Tyr Tyr Arg Ser His Tyr Tyr Ser Met Asp Tyr Trp
            100                 105                 110

Gly Gln Gly Ser Ser Val Thr Val Ser Ser
        115                 120
```

<210> SEQ ID NO 66
<211> LENGTH: 5
<212> TYPE: PRT
<213> ORGANISM: Mus musculus

<400> SEQUENCE: 66

```
Asn Tyr Ala Met Ser
1               5
```

<210> SEQ ID NO 67
<211> LENGTH: 17
<212> TYPE: PRT
<213> ORGANISM: Mus musculus

<400> SEQUENCE: 67

```
Thr Ile Ser Ser Gly Gly Gly Tyr Thr Tyr Tyr Pro Asp Ser Glu Lys
1               5                   10                  15

Gly
```

<210> SEQ ID NO 68
<211> LENGTH: 13
<212> TYPE: PRT
<213> ORGANISM: Mus musculus

<400> SEQUENCE: 68

Gln Leu Tyr Tyr Arg Ser His Tyr Tyr Ser Met Asp Tyr
1               5                   10

<210> SEQ ID NO 69
<211> LENGTH: 318
<212> TYPE: DNA
<213> ORGANISM: Mus musculus

<400> SEQUENCE: 69

```
caaattgttc tcacccagtc tccagcaatc atgtctgcat ctccagggga gaaggtcacc      60
atgacctgca gtgccagctc aagtataagt tatatgcact ggtaccagca gaagtcaggc     120
acctccccca aaagatggat ttatgacaca tccaaactgg cttctggagt ccctgctcgc     180
ttcagtggca gtgggtctgg gacctcttac tctctcacaa tcagcagcat ggaggctgag     240
gatgctgcca cttattactg ccagcagtgg catagtaaac cagccacgtt cggtgctggg     300
accaagctgg agctgaaa                                                   318
```

<210> SEQ ID NO 70
<211> LENGTH: 106
<212> TYPE: PRT
<213> ORGANISM: Mus musculus

<400> SEQUENCE: 70

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp His Ser Lys Pro Ala Thr
                85                  90                  95

Phe Gly Ala Gly Thr Lys Leu Glu Leu Lys
            100                 105

<210> SEQ ID NO 71
<211> LENGTH: 10
<212> TYPE: PRT
<213> ORGANISM: Mus musculus

<400> SEQUENCE: 71

Ser Ala Ser Ser Ser Ile Ser Tyr Met His
1               5                   10

<210> SEQ ID NO 72
<211> LENGTH: 7
<212> TYPE: PRT
<213> ORGANISM: Mus musculus

<400> SEQUENCE: 72

Asp Thr Ser Lys Leu Ala Ser
1               5

<210> SEQ ID NO 73
<211> LENGTH: 9
<212> TYPE: PRT
<213> ORGANISM: Mus musculus

```
<400> SEQUENCE: 73

Gln Gln Trp His Ser Lys Pro Ala Thr
1               5

<210> SEQ ID NO 74
<211> LENGTH: 20
<212> TYPE: DNA
<213> ORGANISM: Artificial Sequence
<220> FEATURE:
<223> OTHER INFORMATION: an artificially synthesized primer sequence

<400> SEQUENCE: 74
gcgaattcca ccatgggatg                                              20

<210> SEQ ID NO 75
<211> LENGTH: 35
<212> TYPE: DNA
<213> ORGANISM: Artificial Sequence
<220> FEATURE:
<223> OTHER INFORMATION: an artificially synthesized primer sequence

<400> SEQUENCE: 75
tgagccaccg ccacctgcag agacagtgac cagag                             35

<210> SEQ ID NO 76
<211> LENGTH: 35
<212> TYPE: DNA
<213> ORGANISM: Artificial Sequence
<220> FEATURE:
<223> OTHER INFORMATION: an artificially synthesized primer sequence

<400> SEQUENCE: 76
ggtggcggtg gctcacagat tgttctcacc cagtc                             35

<210> SEQ ID NO 77
<211> LENGTH: 38
<212> TYPE: DNA
<213> ORGANISM: Artificial Sequence
<220> FEATURE:
<223> OTHER INFORMATION: an artificially synthesized primer sequence

<400> SEQUENCE: 77
actcccacca ccgccttttta tttccaattt tgtccccg                         38

<210> SEQ ID NO 78
<211> LENGTH: 32
<212> TYPE: DNA
<213> ORGANISM: Artificial Sequence
<220> FEATURE:
<223> OTHER INFORMATION: an artificially synthesized primer sequence

<400> SEQUENCE: 78
ggcggtggtg ggagtgagcc cagagggccc ac                                32

<210> SEQ ID NO 79
<211> LENGTH: 20
<212> TYPE: DNA
<213> ORGANISM: Artificial Sequence
<220> FEATURE:
<223> OTHER INFORMATION: an artificially synthesized primer sequence

<400> SEQUENCE: 79
ctctagagcg gccgcttatc                                              20
```

```
<210> SEQ ID NO 80
<211> LENGTH: 65
<212> TYPE: PRT
<213> ORGANISM: Artificial Sequence
<220> FEATURE:
<223> OTHER INFORMATION: del-494W GPR49 epitope

<400> SEQUENCE: 80

Asn Lys Gly Asp Asn Ser Ser Met Asp Asp Leu His Lys Lys Asp Ala
1               5                   10                  15

Gly Met Phe Gln Ala Gln Asp Glu Arg Asp Leu Glu Asp Phe Leu Leu
            20                  25                  30

Asp Phe Glu Glu Asp Leu Lys Ala Leu His Ser Val Gln Cys Ser Pro
        35                  40                  45

Ser Pro Gly Pro Phe Lys Pro Cys Glu His Leu Leu Asp Gly Trp Leu
    50                  55                  60

Ile
65

<210> SEQ ID NO 81
<211> LENGTH: 23
<212> TYPE: PRT
<213> ORGANISM: Artificial Sequence
<220> FEATURE:
<223> OTHER INFORMATION: del-537H GPR49 epitope

<400> SEQUENCE: 81

Ser Val Gln Cys Ser Pro Ser Pro Gly Pro Phe Lys Pro Cys Glu His
1               5                   10                  15

Leu Leu Asp Gly Trp Leu Ile
            20

<210> SEQ ID NO 82
<211> LENGTH: 73
<212> TYPE: PRT
<213> ORGANISM: Artificial Sequence
<220> FEATURE:
<223> OTHER INFORMATION: sGPR49Fc GPR49 epitope
<220> FEATURE:
<221> NAME/KEY: MISC_FEATURE
<222> LOCATION: (73)..(73)
<223> OTHER INFORMATION: May be modified at the C-terminus with a
      mIgGFc polypeptide tag

<400> SEQUENCE: 82

Gly Val Cys Glu Asn Ala Tyr Lys Ile Ser Asn Gln Trp Asn Lys Gly
1               5                   10                  15

Asp Asn Ser Ser Met Asp Asp Leu His Lys Lys Asp Ala Gly Met Phe
            20                  25                  30

Gln Ala Gln Asp Glu Arg Asp Leu Glu Asp Phe Leu Leu Asp Phe Glu
        35                  40                  45

Glu Asp Leu Lys Ala Leu His Ser Val Gln Cys Ser Pro Ser Pro Gly
    50                  55                  60

Pro Phe Lys Pro Cys Glu His Leu Leu
65                  70

<210> SEQ ID NO 83
<211> LENGTH: 43
<212> TYPE: PRT
<213> ORGANISM: Artificial Sequence
<220> FEATURE:
<223> OTHER INFORMATION: GST-495-537 GPR49 epitope
<220> FEATURE:
<221> NAME/KEY: MISC_FEATURE
```

```
<222> LOCATION: (1)..(1)
<223> OTHER INFORMATION: May have an N-terminal GST tag

<400> SEQUENCE: 83

Trp Asn Lys Gly Asp Asn Ser Ser Met Asp Asp Leu His Lys Lys Asp
1               5                   10                  15

Ala Gly Met Phe Gln Ala Gln Asp Glu Arg Asp Leu Glu Asp Phe Leu
            20                  25                  30

Leu Asp Phe Glu Glu Asp Leu Lys Ala Leu His
            35                  40

<210> SEQ ID NO 84
<211> LENGTH: 22
<212> TYPE: PRT
<213> ORGANISM: Artificial Sequence
<220> FEATURE:
<223> OTHER INFORMATION: GST-496-516 GPR49 epitope
<220> FEATURE:
<221> NAME/KEY: MISC_FEATURE
<222> LOCATION: (1)..(1)
<223> OTHER INFORMATION: May have an N-terminal GST tag

<400> SEQUENCE: 84

Trp Asn Lys Gly Asp Asn Ser Ser Met Asp Asp Leu His Lys Lys Asp
1               5                   10                  15

Ala Gly Met Phe Gln Ala
            20

<210> SEQ ID NO 85
<211> LENGTH: 20
<212> TYPE: PRT
<213> ORGANISM: Artificial Sequence
<220> FEATURE:
<223> OTHER INFORMATION: GST-510-529 GPR49 epitope
<220> FEATURE:
<221> NAME/KEY: MISC_FEATURE
<222> LOCATION: (1)..(1)
<223> OTHER INFORMATION: May have an N-terminal GST tag

<400> SEQUENCE: 85

Asp Ala Gly Met Phe Gln Ala Gln Asp Glu Arg Asp Leu Glu Asp Phe
1               5                   10                  15

Leu Leu Asp Phe
            20

<210> SEQ ID NO 86
<211> LENGTH: 21
<212> TYPE: PRT
<213> ORGANISM: Artificial Sequence
<220> FEATURE:
<223> OTHER INFORMATION: GST-517-537 GPR49 epitope
<220> FEATURE:
<221> NAME/KEY: MISC_FEATURE
<222> LOCATION: (1)..(1)
<223> OTHER INFORMATION: May have an N-terminal GST tag

<400> SEQUENCE: 86

Gln Asp Glu Arg Asp Leu Glu Asp Phe Leu Leu Asp Phe Glu Glu Asp
1               5                   10                  15

Leu Lys Ala Leu His
            20
```